(12) United States Patent
Martin et al.

(10) Patent No.: US 11,099,190 B2
(45) Date of Patent: Aug. 24, 2021

(54) POLYMERIC DYE RATIOMETRIC SENSOR FOR ANALYTE DETECTION AND METHODS OF USING THE SAME

(71) Applicant: Becton, Dickinson and Company, Franklin Lakes, NJ (US)

(72) Inventors: Jody Martin, Encinitas, CA (US); Robert J. Radford, Skokie, IL (US); James Ghadiali, San Diego, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 23 days.

(21) Appl. No.: 15/780,219

(22) PCT Filed: Dec. 6, 2016

(86) PCT No.: PCT/US2016/065192
§ 371 (c)(1),
(2) Date: May 30, 2018

(87) PCT Pub. No.: WO2017/105927
PCT Pub. Date: Jun. 22, 2017

(65) Prior Publication Data
US 2018/0364245 A1 Dec. 20, 2018

Related U.S. Application Data

(60) Provisional application No. 62/268,268, filed on Dec. 16, 2015.

(51) Int. Cl.
*G01N 33/58* (2006.01)
*G01N 33/542* (2006.01)
(Continued)

(52) U.S. Cl.
CPC ........... *G01N 33/582* (2013.01); *C07K 16/44* (2013.01); *G01N 33/53* (2013.01); *G01N 33/542* (2013.01);
(Continued)

(58) Field of Classification Search
CPC .... G01N 33/582; G01N 33/542; G01N 33/53; C07K 16/44; C07K 2317/56; C07K 2317/55; C09K 11/06
See application file for complete search history.

(56) References Cited

U.S. PATENT DOCUMENTS

2017/0174892 A1* 6/2017 Radford ................ C09B 69/109

FOREIGN PATENT DOCUMENTS

WO    WO-2011091086 A1 *  7/2011  ............. C08G 61/02

OTHER PUBLICATIONS

Dinakaran et al. Synthesis and characterization of fluorescent poly[(fluorene-co-phenylene-1(dipyridylamine)] copolymer and is Ru(II) complex. J. Polymer Sci 2004, vol. 42, pp. 557-563. (Year: 2004).*
(Continued)

*Primary Examiner* — Shafiqul Haq
(74) *Attorney, Agent, or Firm* — Bret E. Field; Bozicevic, Field & Francis LLP

(57) ABSTRACT

Fluorogenic sensors for a target analyte are provided. The fluorogenic sensors can include a water soluble light harvesting multichromophore and a fluorogenic dye covalently linked to the multichromophore and in energy-receiving proximity therewith. Aspects of the fluorogenic sensors include selective recognition of the target analyte by chemical reaction or by specific binding. In some cases, the linked fluorogenic dye includes a lactone or spiro-lactone group that is configured to chemically react with a target analyte via lactone ring-opening to produce a fluorescent dye con-
(Continued)

figured for excitation by the multichromophore. Also provided are labelled specific binding members that include the subject dyes. Methods of evaluating a sample for the presence of a target analyte and methods of labelling a target molecule in which the subject fluorogenic sensors find use are provided. Systems, devices and kits for practicing the subject methods are provided.

12 Claims, 5 Drawing Sheets

(51) Int. Cl.
 *C07K 16/44* (2006.01)
 *G01N 33/53* (2006.01)
 *C09K 11/06* (2006.01)

(52) U.S. Cl.
 CPC ...... *C07K 2317/55* (2013.01); *C07K 2317/56* (2013.01); *C09K 11/06* (2013.01)

(56) References Cited

OTHER PUBLICATIONS

He et al. Fluorescence ratiometric assays of hydrogen peroxide and glucose in serum using conjugated polyelectrolytes. J. Mater. Chem. 2007, vol. 17, pp. 3702-3707. (Year: 2007).*
Thivierge et al. Brilliant BODIPY—fluorene coplymers with dispersed absorption and emission maxima. Macromolecules 2011, vol. 44, pp. 4012-4015. (Year: 2011).*
Marfin et al. Interaction of BODIPY dyes with the blood plasma proteins. J. Fluoresc 2016, vol. 26, pp. 255-261. (Year: 2016).*
Traina et al. Design and synthesis of monofunctionalized, water-soluble conjugated polymers for biosensing and imaging applications. J. Am. Chem. Soc. 2011, vol. 133, p. 12600-12607. (Year: 2011).*
Bura et al. Design, synthesis and redox properties of a fluorene platform linking two different bodipy dyes. Tetrahedron letters 2010, vol. 51, pp. 2875-2879. (Year: 2010).*
Carter et al. Fluorescent sensors for measuring metal ions in living systems. Chem. Rev. 2014, vol. 114, pp. 4564-4601. (Year: 2014).*
Zheng et al. Fluorogenic and chromogenic rhodamine spirolactam based probe for nitric oxide by spiro ring opening reaction. Organic Letters 2008, vol. 10, No. 10, pp. 2357-2360. (Year: 2008).*

* cited by examiner ically*US 11,099,190 B2*

POLYMERIC DYE RATIOMETRIC SENSOR FOR ANALYTE DETECTION AND METHODS OF USING THE SAME

CROSS-REFERENCE TO RELATED APPLICATION

Pursuant to 35 U.S.C. § 119(e), this application claims priority to the filing date of U.S. Provisional Patent Application No. 62/268,268, filed Dec. 16, 2015; the disclosure of which application is herein incorporated by reference.

INTRODUCTION

Fluorescent dyes are compounds which, when irradiated with light of a wavelength which they absorb, emit light of a (usually) different wavelength. Fluorescent dyes find use in a variety of applications in biochemistry, biology and medicine, e.g., in diagnostic kits, in microscopy, in drug screening and in sensors. Fluorescent dyes are characterized by a number of chemical or physical properties and spectral parameters allowing a user to select a suitable dye depending on the desired purpose. Spectral parameters of interest include the excitation wavelength maximum, the emission wavelength maximum, the Stokes shift, the extinction coefficient, the fluorescence quantum yield and the fluorescence lifetime. Dyes may be selected according to the application of interest in order to, e.g., allow penetration of exciting radiation into biological samples, to minimize background fluorescence, to achieve a high signal-to-noise ratio and/or to sense the presence of an analyte. Fluorescent sensors or probes can be used to detect the temporal and spatial distribution of analytes of interest in a sample.

SUMMARY

Fluorogenic sensors for a target analyte are provided. The fluorogenic sensors can include a water soluble light harvesting multichromophore and a fluorogenic dye covalently linked to the multichromophore and in energy-receiving proximity therewith. Aspects of the fluorogenic sensors include selective recognition of the target analyte by chemical reaction or by specific binding. In some cases, the linked fluorogenic dye includes a lactone or spiro-lactone group that is configured to chemically react with a target analyte via lactone ring-opening to produce a fluorescent dye configured for excitation by the multichromophore. Also provided are labelled specific binding members that include the subject dyes. Methods of evaluating a sample for the presence of a target analyte and methods of labelling a target molecule in which the subject fluorogenic sensors find use are also provided. Systems, devices and kits for practicing the subject methods are also provided.

BRIEF DESCRIPTION OF THE FIGURES

It is understood that the drawings, described below, are for illustration purposes only. The drawings are not intended to limit the scope of the present teachings in any way.

DEFINITIONS

Figure 1:
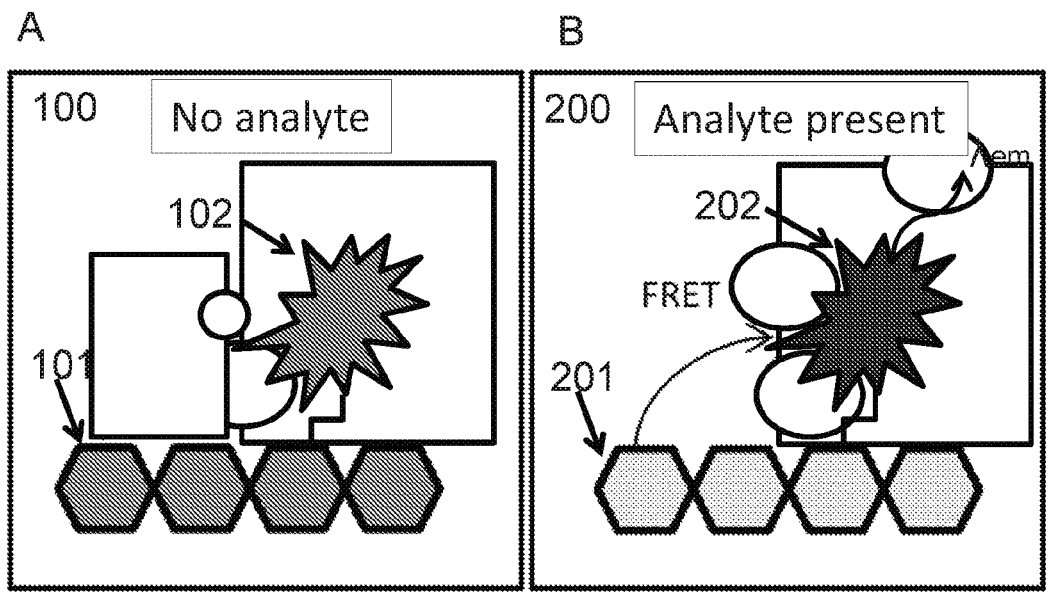
FIG. 1 illustrates a schematic of a fluorogenic sensor (100) (Panel A) that includes a water soluble light harvesting multichromophore as a donor (101) and a fluorogenic dye as an acceptor (102). The fluorogenic dye senses the target analyte (Panel B) to produce a fluorescent sensor molecule (200) where FRET occurs from the donor water soluble light harvesting multichromophore (201) to the acceptor fluorescent dye (202) to release a ratiometric fluorescent signal ($\lambda_{em}$).

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the term "sample" relates to a material or mixture of materials, in some cases in liquid form, containing one or more analytes of interest. In some embodiments, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents, as well as samples from the environment. The term "sample" may also refer to a "biological sample". As used herein, the term "a biological sample" refers to a whole organism or a subset of its tissues, cells or component parts (e.g. body fluids, including, but not limited to, blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, plasma, serum, spinal fluid, lymph fluid, the external sections of the skin, respiratory, intestinal, and genitourinary tracts, tears, saliva, milk, blood cells, tumors and organs. In certain embodiments, the sample has been removed from an animal or plant. Biological samples may include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

As used herein, the terms "support bound" and "linked to a support" are used interchangeably and refer to a moiety (e.g., a specific binding member) that is linked covalently or non-covalently to a support of interest. Covalent linking may involve the chemical reaction of two compatible functional groups (e.g., two chemoselective functional groups, an electrophile and a nucleophile, etc.) to form a covalent bond between the two moieties of interest (e.g. a support and a specific binding member). In some cases, non-covalent linking may involve specific binding between two moieties of interest (e.g., two affinity moieties such as a hapten and an antibody or a biotin moiety and a streptavidin, etc.). In certain cases, non-covalent linking may involve absorption to a substrate.

As used herein, the term "polypeptide" refers to a polymeric form of amino acids of any length, including peptides that range from 2-50 amino acids in length and polypeptides that are greater than 50 amino acids in length. The terms "polypeptide" and "protein" are used interchangeably herein. The term "polypeptide" includes polymers of coded and non-coded amino acids, chemically or biochemically modified or derivatized amino acids, and polypeptides having modified peptide backbones in which the conventional backbone has been replaced with non-naturally occurring or synthetic backbones. A polypeptide may be of any convenient length, e.g., 2 or more amino acids, such as 4 or more amino acids, 10 or more amino acids, 20 or more amino acids, 50 or more amino acids, 100 or more amino acids, 300 or more amino acids, such as up to 500 or 1000 or more amino acids. "Peptides" may be 2 or more amino acids, such as 4 or more amino acids, 10 or more amino acids, 20 or more amino acids, such as up to 50 amino acids. In some embodiments, peptides are between 5 and 30 amino acids in length.

As used herein the term "isolated," refers to an moiety of interest that is at least 60% free, at least 75% free, at least 90% free, at least 95% free, at least 98% free, and even at least 99% free from other components with which the moiety is associated with prior to purification.

A "plurality" contains at least 2 members. In certain cases, a plurality may have 10 or more, such as 100 or more, 1000 or more, 10,000 or more, 100,000 or more, $10^6$ or more, $10^7$ or more, $10^8$ or more or $10^9$ or more members.

Numeric ranges are inclusive of the numbers defining the range.

As used herein, the term "specific binding" refers to the ability of a capture agent (or a first member of a specific binding pair) to preferentially bind to a particular analyte (or a second member of a specific binding pair) that is present, e.g., in a homogeneous mixture of different analytes. In some instances, a specific binding interaction will discriminate between desirable and undesirable analytes in a sample with a specificity of 10-fold or more for a desirable analyte over an undesirable analytes, such as 100-fold or more, or 1000-fold or more. In some cases, the affinity between a capture agent and analyte when they are specifically bound in a capture agent/analyte complex is at least $10^{-8}$M, at least $10^{-9}$M, such as up to $10^{-10}$M.

As used herein, the terms "affinity" and "avidity" have the same meaning and may be used interchangeably herein. "Affinity" refers to the strength of binding, increased binding affinity being correlated with a lower Kd.

The methods described herein include multiple steps. Each step may be performed after a predetermined amount of time has elapsed between steps, as desired. As such, the time between performing each step may be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step may be performed after an incubation or waiting time after completion of the previous step, e.g., a few minutes to an overnight waiting time.

As used herein, the terms "evaluating", "determining," "measuring," and "assessing," and "assaying" are used interchangeably and include both quantitative and qualitative determinations.

The term "separating", as used herein, refers to physical separation of two elements (e.g., by size or affinity, etc.) as well as degradation of one element, leaving the other intact.

As used herein, the term "linker" or "linkage" refers to a linking moiety that connects two groups and has a backbone of 100 atoms or less in length. A linker or linkage may be a covalent bond that connects two groups or a chain of between 1 and 100 atoms in length, for example a chain of 1, 2, 3, 4, 5, 6, 8, 10, 12, 14, 16, 18, 20 or more carbon atoms in length, where the linker may be linear, branched, cyclic or a single atom. In some cases, the linker is a branching linker that refers to a linking moiety that connects three or more groups. In certain cases, one, two, three, four or five or more carbon atoms of a linker backbone may be optionally substituted with a sulfur, nitrogen or oxygen heteroatom. The bonds between backbone atoms may be saturated or unsaturated, and in some cases not more than one, two, or three unsaturated bonds are present in a linker backbone. The linker may include one or more substituent groups, for example with an alkyl, aryl or alkenyl group. A linker may include, without limitations, polyethylene glycol; ethers, thioethers, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

As used herein, the terms "polyethylene oxide", "PEO", "polyethylene glycol" and "PEG" are used interchangeably and refer to a polymeric group including a chain described by the formula —($CH_2$—$CH_2$—O—)$_n$— or a derivative thereof. In some embodiments, "n" is 5000 or less, such as 1000 or less, 500 or less, 200 or less, 100 or less, 50 or less, 40 or less, 30 or less, 20 or less, 15 or less, such as 3 to 15, or 10 to 15. It is understood that the PEG polymeric group may be of any convenient length and may include a variety of terminal groups and/or further substituent groups, including but not limited to, alkyl, aryl, hydroxyl, amino, acyl, acyloxy, and amido terminal and/or substituent groups. PEG groups that may be adapted for use in the subject multichromophores include those PEGs described by S. Zalipsky in "Functionalized poly(ethylene glycol) for preparation of biologically relevant conjugates", Bioconjugate Chemistry 1995, 6 (2), 150-165; and by Zhu et al in "Water-Soluble Conjugated Polymers for Imaging, Diagnosis, and Therapy", Chem. Rev., 2012, 112 (8), pp 4687-4735.

As used herein, the term "alkyl" by itself or as part of another substituent refers to a saturated branched or straight-chain monovalent hydrocarbon radical derived by the removal of one hydrogen atom from a single carbon atom of a parent alkane. Alkyl groups of interest include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group includes from 1 to 20 carbon atoms. In some embodiments, an alkyl group includes from 1 to 10 carbon atoms. In certain embodiments, an alkyl group includes from 1 to 6 carbon atoms, such as from 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$— heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$—

"Aryl" by itself or as part of another substituent refers to a monovalent aromatic hydrocarbon radical derived by the removal of one hydrogen atom from a single carbon atom of an aromatic ring system. Aryl groups of interest include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group includes from 6 to 20 carbon atoms. In certain embodiments, an aryl group includes from 6 to 12 carbon atoms. Examples of an aryl group are phenyl and naphthyl.

"Heteroaryl" by itself or as part of another substituent, refers to a monovalent heteroaromatic radical derived by the removal of one hydrogen atom from a single atom of a heteroaromatic ring system. Heteroaryl groups of interest include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, triazole, benzotriazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$- moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

The term "alkaryl" or "aralkyl" refers to the groups -alkylene-aryl and substituted alkylene-aryl where alkylene, substituted alkylene and aryl are defined herein.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like. "Substituted alkylene" refers to an alkylene group having from 1 to 3 hydrogens replaced with substituents as described for carbons in the definition of "substituted" below.

"Substituted" refers to a group in which one or more hydrogen atoms are independently replaced with the same or different substituent(s). Substituents of interest include, but are not limited to, alkylenedioxy (such as methylenedioxy), -M, —R$^{60}$, —O$^-$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{60}$, —OS(O)$_2$O$^-$, —OS(O)$_2$R$^{60}$, —P(O)(O$^-$)$_2$, —P(O)(OR$^{60}$) (O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$ and —C(NR$^{62}$)NR$^{60}$R$^{61}$ where M is halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally R$^{60}$ and R$^{61}$ together with the nitrogen atom to which they are bonded form a cycloheteroalkyl or substituted cycloheteroalkyl ring; and R$^{64}$ and R$^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally R$^{64}$ and R$^{65}$ together with the nitrogen atom to which they are bonded form a cycloheteroalkyl or substituted cycloheteroalkyl ring. In certain embodiments, substituents include -M, —R$^{60}$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —NR$^{62}$C(O)NR$^{60}$R$^{61}$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —P(O)(OR$^{60}$)(O$^-$), —OP(O)(OR$^{60}$)(OR$^{61}$), —C(O)R$^{60}$, —C(O)OR$^{60}$, —C(O)NR$^{60}$R$^{61}$, —C(O)O$^-$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —OP(O)(OR$^{60}$)(OR$^{61}$), —C(O)R$^{60}$, —C(O)OR$^{60}$, —C(O)O$^-$, where R$^{60}$, R$^{61}$ and R$^{62}$ are as defined above. For example, a substituted group may bear a methylenedioxy substituent or one, two, or three substituents selected from a halogen atom, a (1-4C)alkyl group and a (1-4C)alkoxy group. When the group being substituted is an aryl or heteroaryl group, the substituent(s) (e.g., as described herein) may be referred to as "aryl substituent(s)".

Other definitions of terms may appear throughout the specification.

DETAILED DESCRIPTION

As summarized above, fluorogenic sensors for a target analyte are provided. The fluorogenic sensors can include a water soluble light harvesting multichromophore and a fluorogenic dye covalently linked to the multichromophore and in energy-receiving proximity therewith. Aspects of the fluorogenic sensors include selective recognition of the target analyte by chemical reaction or by specific binding. In some cases, the linked fluorogenic dye includes a lactone or spiro-lactone group that is configured to chemically react with a target analyte via lactone ring-opening to produce a fluorescent dye configured for excitation by the multichromophore. Also provided are labelled specific binding members that include the subject dyes. Methods of evaluating a sample for the presence of a target analyte and methods of labelling a target molecule in which the subject fluorogenic sensors find use are provided. Systems, devices and kits for practicing the subject methods are provided.

Before the various embodiments are described in greater detail, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

In further describing the subject invention, fluorogenic sensors including donor light harvesting multichromophores and acceptor fluorogenic dyes are described first in greater detail. Next, labelled specific binding members which include the subject fluorogenic sensors are described. Then, methods of interest in which fluorogenic sensors find use are reviewed. Systems, devices and kits that may be used in practicing methods of the invention are also described.

Fluorogenic Sensors

As summarized above, the present disclosure provides fluorogenic sensors. The subject fluorogenic sensors include a donor water soluble light harvesting multichromophore and a covalently linked fluorogenic dye acceptor in energy-receiving proximity to the multichromophore. The fluorogenic dye is configured to sense the target analyte to produce a fluorescent dye product configured for excitation by the multichromophore. As used herein, the term "fluorogenic" refers to an acceptor dye moiety that is capable of demonstrating a change in fluorescence upon interaction with a target analyte of interest. The fluorogenic dye can have a non-fluorescent form or "off-state" in the absence of target analyte and is capable of being converted to a fluorescent form or "on-state" in the presence of target analyte. The conversion of the linked fluorogenic dye to a linked fluorescent dye product (i.e., conversion of the dye from an off-state to an on-state) can be achieved in a variety of methods via the direct or indirect action of the target analyte on the fluorogenic dye (e.g., as described herein). As used herein, the term "off-state" refers to a first chemical or physical form of the fluorogenic sensor and/or linked fluorogenic dye component of the subject sensor that exists in the absence of target analyte. As used herein, the term "on-state" refers to a second chemical or physical form of the fluorogenic sensor and/or linked fluorescent dye product that exists after the direct or indirect action of target analyte on linked fluorogenic dye component.

As used herein, the term "chemical form" refers to the chemical structure of a molecule, where the first and second forms of a fluorogenic dye involve distinct chemical structures which can have different spectral properties. As used herein, the term "physical form" is meant to encompass a variety of different physical forms of a molecule having identical chemical structure, but having different spectral properties due to the molecule being in e.g., a different electronic state, a different steric state, or a different physical environment. In some cases, first and second physical forms of a molecule include analyte bound (e.g., non-covalently bound) and unbound forms.

The subject fluorogenic sensors provide for a measurable fluorescence emission difference between the off-state and on-state of the sensor. As such, the target analyte can be detected in a sample by observing an increase in fluorescence from the sensor. It is understood that, in some cases, the "off-state" or "non-fluorescent form" of the fluorogenic sensor or of the fluorogenic dye itself may have some inherent fluorescence that is relatively small as compared to the fluorescence of the "on-state" or "fluorescent form" of the sensor.

In some cases, the fluorogenic sensor is ratiometric. As used herein, the term "ratiometric" refers to a composition containing a sensor for a target analyte where the intensity of the fluorescence emission signal obtained from the composition is proportional to the amount of target analyte that is present. As such, measurement of the fluorescence emission signal can be used to quantitate the amount of target analyte that is present in the composition. The water soluble light harvesting multichromophore is itself fluorescent and is configured to transfer energy to a linked acceptor dye. As such, excitation of the multichromophore donor can lead to energy transfer to the covalently attached acceptor, either the fluorogenic dye or the fluorescent dye product.

When the fluorogenic dye is in its off-state form, the dye is relatively non-fluorescent. Upon conversion of the fluorogenic dye to a fluorescent dye product (i.e., the on-state form of the dye), energy transfer from the donor multichromophore produces a measurable fluorescence emission from the acceptor dye. It is understood that, when the fluorogenic dye is in its off-state form even though the dye may not yet be capable of emitting a strong fluorescent signal, the fluorogenic dye can still accept energy from the donor multichromophore. In some cases, the off-state form of the fluorogenic dye can quench (at least partially) the inherent fluorescence of the multichromophore. In some instances, the fluorogenic dye is capable of quenching 10% or more of the fluorescence of the multichromophore, such as 20% or more, 30% or more, 40% or more, 50% or more, 60% or more, 70% or more, 80% or more, 90% or more or 100% of the multichromophore's inherent fluorescence, e.g., as compared to the fluorescence of a multichromophore control that lacks a linked acceptor moiety.

In some embodiments, the fluorogenic sensor is non-fluorescent in the absence of target analyte when the sensor is irradiated with incident excitation light at the absorption maxima wavelength of the multichromophore. By "incident excitation light" is meant light having a wavelength and intensity suitable for exciting the light harvesting multichromophore. In some embodiments, the fluorescence ratio of fluorescent versus non-fluorescent forms of the sensor is 10 or more, such as 30 or more, 100 or more, 300 or more 1,000 or more, 3,000 or more, 10,000 or more, or even more, e.g., when the sensor forms are irradiated with incident excitation light at the absorption maxima wavelength of the multichromophore.

Mechanisms for energy transfer from the fluorescent water soluble light harvesting multichromophore donor to the linked acceptor include, for example, resonant energy transfer (e.g., Förster (or fluorescence) resonance energy transfer, FRET), quantum charge exchange (Dexter energy transfer) and the like. In some instances, these energy transfer mechanisms are relatively short range; that is, close proximity of the light harvesting multichromophore system to the acceptor dye provides for efficient energy transfer. In some instances, under conditions for efficient energy transfer, amplification of the emission from the acceptor dye occurs when the number of individual dyes in the light harvesting multichromophore system is large; that is, the emission from the luminescent dye (e.g., signaling chromophore) is more intense when the incident light (the "pump light") is at a wavelength which is absorbed by the light harvesting multichromophore than when the dye is directly excited by the pump light.

By "efficient" energy transfer is meant 10% or more, such as 20% or more or 30% or more, of the energy harvested by the donor is transferred to the acceptor. By "amplification" is meant that the signal from the acceptor chromophore is 1.5× or greater when excited by energy transfer from the donor light harvesting multichromophore as compared to direct excitation with incident light of an equivalent intensity. The signal may be measured using any convenient method. In some cases, the 1.5× or greater signal refers to an intensity of emitted light. In certain cases, the 1.5× or greater signal refers to an increased signal to noise ratio. In certain embodiments of the fluorescence sensor, the acceptor chromophore emission is 1.5 fold greater or more when excited by the multichromophore as compared to direct excitation of the acceptor chromophore with incident light. As used herein, the terms "acceptor chromophore", "acceptor dye" and "acceptor fluorescent dye" are used interchangeably.

The linked acceptor dye emission of the sensor in its "on-state" can have a quantum yield of 0.1 or more, such as a quantum yield of 0.15 or more, 0.2 or more, 0.25 or more, 0.3 or more, 0.35 or more, 0.4 or more, 0.45 or more, 0.5 or more or even more. In some instances, the sensor has an extinction coefficient of $5\times10^5$ $cm^{-1}M^{-1}$ or more, such as $6\times10^5$ $cm^{-1}M^{-1}$ or more, $7\times10^5$ $cm^{-1}M^{-1}$ or more, $8\times10^5$ $cm^{-1}M^{-1}$ or more, $9\times10^5$ $cm^{-1}M^{-1}$ or more, such as $1\times10^6$ $cm^{-1}M^{-1}$ or more, $1.5\times10^6$ $cm^{-1}M^{-1}$ or more, $2\times10^6$ $cm^{-1}M^{-1}$ or more, $2.5\times10^6$ $cm^{-1}M^{-1}$ or more, $3\times10^6$ $cm^{-1}M^{-1}$ or more, $4\times10^6$ $cm^{-1}M^{-1}$ or more, $5\times10^6$ $cm^{-1}M^{-1}$ or more, $6 \times 10^6$ cm$^{-1}$M$^{-1}$ or more, $7 \times 10^6$ cm$^{-1}$M$^{-1}$ or more, or $8 \times 10^6$ cm$^{-1}$M$^{-1}$ or more. In some embodiments, the sensor has a molar extinction coefficient of $5 \times 10^5$ M$^{-1}$ cm$^{-1}$ or more. In certain embodiments, the sensor has a molar extinction coefficient of $1 \times 10^6$ M$^{-1}$ cm$^{-1}$ or more.

The subject sensors can provide for fluorescence emissions from the linked fluorescent dye product that are brighter than the emissions which are possible from such fluorescent dyes in isolation. The emission of the subject sensor in its "on-state" can have a brightness of 100 mM$^{-1}$ cm$^{-1}$ or more, 150 mM$^{-1}$ cm$^{-1}$ or more, 200 mM$^{-1}$ cm$^{-1}$ or more, 250 mM$^{-1}$ cm$^{-1}$ or more, 300 mM$^{-1}$ cm$^{-1}$ or more, 400 mM$^{-1}$ cm$^{-1}$ or more, 500 mM$^{-1}$ cm$^{-1}$ or more, 600 mM$^{-1}$ cm$^{-1}$ or more, 700 mM$^{-1}$ cm$^{-1}$ or more, 800 mM$^{-1}$ cm$^{-1}$ or more, 900 mM$^{-1}$ cm$^{-1}$ or more, 1,000 mM$^{-1}$ cm$^{-1}$ or more, or even more. In certain instances, the emission of the sensor in its "on-state" has a brightness that is at least 5-fold greater than the brightness of a directly excited fluorescent dye control, such as at least 10-fold greater, at least 20-fold greater, at least 30-fold greater, at least 50-fold greater, at least 100-fold greater, at least 300-fold greater, or even greater than the brightness of a directly excited fluorescent dye control.

Linked Fluorogenic Dyes

Aspects of the subject fluorogenic sensors include a fluorogenic dye moiety that is linked to the water soluble light harvesting multichromophore. As such, the fluorogenic sensors are referred to interchangeably herein as a polymeric tandem dye. The number of fluorogenic dye moieties that are linked to the donor water soluble light harvesting multichromophore may vary, where in some instances the number ranges from 1 mol % to 50 mol %, such as from 5 mol % to 25 mol % or from 10 mol % to 25 mol %. By transferring energy of a suitable wavelength from the light harvesting multichromophore to the linked fluorogenic dye moiety the brightness of the fluorescence response (directly or indirectly) to the action of a target analyte can be increased relative to a directly excited fluorogenic dye moiety.

Any convenient fluorogenic dye moieties may be adapted for use in the subject fluorogenic sensors. In some instances, the linked fluorogenic dye specifically binds the target analyte. In some embodiments, the linked fluorogenic dye is chemically reactive with the target analyte. It is understood that a variety of fluorogenic dye moieties may be utilized in the sensors, and that the selection of a water soluble light harvesting multichromophore and a fluorogenic dye moiety for linking thereto is dependent on a variety of factors, such as the absorption and emission maxima of the multichromophore, the nature of the target analyte, the chemical and/or physical forms of the fluorogenic response to analyte, the absorption maxima of both the fluorogenic dye moiety and the fluorescent dye product to which it is converted, the emission maxima of the fluorescent dye product, the Stokes shift of a particular combination of multichromophore and fluorescent dye product, etc. It is understood that any of the fluorogenic dye moieties described herein may be selected and adapted for covalent linkage to the multichromophore via any convenient point of attachment.

Any convenient target analytes can be targeted for sensing by the subject fluorogenic sensors. Target analytes of interest include, but are not limited to, hydroxide or hydrogen ion (e.g., pH sensors), metal ions, saccharides (e.g., glucose or fructose), organic anions (e.g., lactate, citrate or pyrophosphate), reactive oxygen species (e.g., hydrogen peroxide, oxygen, etc.), reactive nitrogen species (e.g., nitric oxide), a drug (e.g., a small molecule drug, such as diethylstilbestrol, anticancer drug such as a platinum drug), environmental contaminants or toxic chemicals, polynucleotides, peptides, proteins, and the like.

A variety of fluorogenic dyes that sense directly or indirectly a target analyte of interest can be selected for incorporation into the subject fluorogenic sensors. The linked fluorogenic dye can be a cyanine-based dye. The linked fluorogenic dye can be a xanthene-based dye (e.g., a fluorescein or a rhodamine dye). The linked fluorogenic dye can include a dye group and an analyte reactive group. The linked fluorogenic dye can include a dye group and an analyte binding ligand, such as a specific binding moiety that specifically binds the analyte, or a metal ion chelating ligand. In certain embodiments, the linked fluorogenic dye includes a lactam, a lactone or a spiro-lactone group that is configured to chemically react with the target analyte via ring-opening reaction to produce the fluorescent dye. A variety of fluorescein and rhodamine-based dyes may be adapted for use in the subject sensors, including but not limited to, carbofluorescein lactones, carbofluorescein lactams, carborhodamine lactones, carborhodamine lactams, fluorescein lactones, fluorescein lactams, rhodamine lactones, rhodamine lactams, and 2',7'-dichlorodihydrofluorescein diacetate (H2DCFDA).

Fluorogenic dyes of interest include, but are not limited to, 4-(4-dimethylaminostyryl)-1-hexadecylpyridinium (DSHP) (e.g., a sensor for lysophosphatidic acid (LPA)), pHrodo® Red dye (e.g., a fluorogenic dye that increases in fluorescence as the pH of its surroundings become more acidic), 4-N,N-dimethylamino-1,8-naphthalimide (4-DMN), (1,4-Bis(4-(trifluoromethyl)coumarin-thioureido-etheneamino)anthraquinone) (e.g., citrate ion sensor), Cy-DES (probe for diethylstilbestrol), rhodamine-piperazine conjugate (sensor for mercury(II) ions), peroxyfluor 1 (PF1), peroxyfluor 2 (PF2), peroxy green 1 (PG1), peroxy yellow 1 (PY1), peroxy orange-1 (PO1), peroxyfluor 6 (PF6) or an AM ester thereof, mitochondria peroxy yellow 1 (MitoPY1), nuclear peroxy emerald 1 (NucPE1), Nitirxyte Orange and those fluorogenic dyes described by Grimm et al. ("Carbofluoresceins and Carborhodamines as Scaffolds for High Contrast Fluorogenic Probes", ACS Chem. Biol. 2013, 8, 1303-1310), Zheng et al. in "Fluorogenic and Chromogenic Rhodamine Spirolactam Based Probe for Nitric Oxide by Spiro Ring Opening Reaction" (Org. Lett., 2008, 10 (12), pp 2357-2360); Brandt et al., Analytical Biochemistry, Volume 11, Issue 1, April 1965, Pages 6-9; Wu et al. in "Selective sensing of saccharides using simple boronic acids and their aggregates", Chem. Soc. Rev., 2013, 42, 8032-8048; U.S. Pat. No. 4,861,728, the disclosures of which are herein incorporated by reference.

In certain instances, fluorogenic dyes which may be adapted for use in the subject sensors are described by the formula (I):

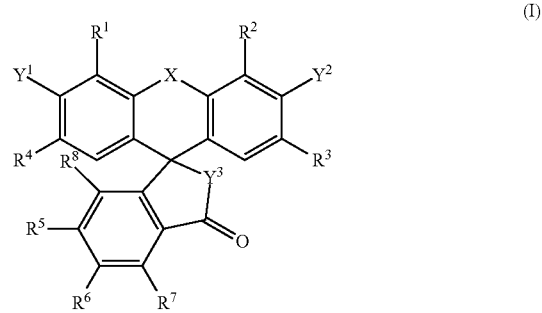

wherein:

$Y^1$ and $Y^2$ are independently OR and $NR_2$, wherein each R is independently selected from H, an alkyl, a substituted alkyl, an acyl and a substituted acyl, and each R can be optionally cyclically linked to $R^1$, $R^2$, $R^3$ or $R^4$ (e.g., to form a 5- or 6-membered ring that is a substituted fused heterocycle);

X is O or $C(R')_2$ wherein each R' is independently an alkyl or a substituted alkyl;

$Y^3$ is O or NR''', wherein R''' is an aryl, a substituted aryl, a heteroaryl, a substituted heteroaryl, an alkyl or a substituted alkyl;

$R^1$-$R^4$ are each independently H, chloro or fluoro; and $R^5$-$R^8$ are each independently H, a linker, a halogen, an alkyl, a substituted alkyl, an aryl, a substituted aryl, a substituted carboxyamido, a substituted alkoxy, a substituted amino, wherein optionally $R^5$ and $R^6$ or $R^6$ and $R^7$ combine to form a metal ion-chelating moiety. In certain instances of formula (I), Y3 is NR'', where R''' is a substituted aryl or heteroaryl. In certain instances, R''' is an amino-substituted phenyl.

In some embodiments, the fluorogenic dye which may be adapted for use in the subject sensors has the following structure:

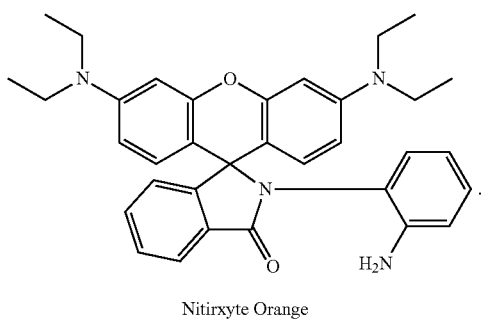 [SMILES: CCN(CC)c1ccc2c(c1)Oc1cc(N(CC)CC)ccc1C21c2ccccc2C(=O)N1c1ccccc1N]

Nitirxyte Orange

In some embodiments, the fluorogenic dye which may be adapted for use in the subject sensors has the following structure:

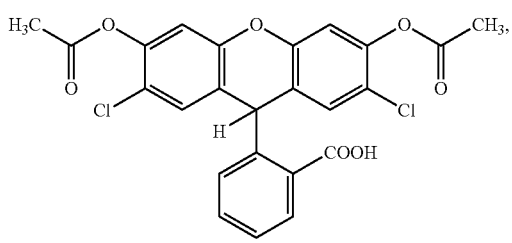 [SMILES: CC(=O)Oc1cc2c(cc1Cl)C(c1ccccc1C(=O)O)c1cc(Cl)c(OC(C)=O)cc1O2]

or a lactone version thereof.

In some embodiments, the linked fluorogenic dye is described by the formula (XI):

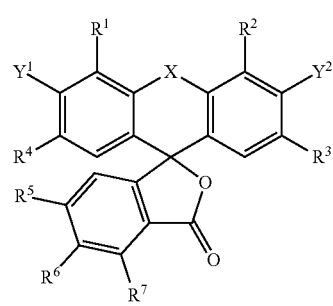

(II)

wherein:

$Y^1$ and $Y^2$ are independently OR and $NR_2$, wherein each R is independently selected from H, an alkyl, a substituted alkyl, an acyl and a substituted acyl;

X is O or $C(R')_2$ wherein each R' is independently an alkyl or a substituted alkyl;

$R^1$-$R^4$ are each independently H, chloro or fluoro;

$R^5$-$R^7$ are each independently H, a linker, a halogen, an alkyl, a substituted alkyl, an aryl, a substituted aryl, a substituted carboxyamido, a substituted alkoxy, a substituted amino, wherein optionally $R^5$ and $R^6$ or $R^6$ and $R^7$ combine to form a metal ion-chelating moiety; wherein at least one of $R^5$-$R^7$ is linked to the multichromophore.

In some embodiments of formula (II), $R^1$ and $R^2$ are H. In some embodiments of formula (II), $R^1$ and $R^2$ are Cl. In some embodiments of formula (II), $R^1$ and $R^2$ are F. In some embodiments of formula (II), $R^3$ and $R^4$ are H. In some embodiments of formula (II), $R^3$ and $R^4$ are Cl. In some embodiments of formula (II), $R^3$ and $R^4$ are F. In some embodiments of formula (II), X is O. In some embodiments of formula (II), X is $C(R')_2$ wherein each R' is independently an alkyl or a substituted alkyl. In some embodiments of formula (II), X is $C(CH_3)_2$. In some embodiments of formula (II), $Y^1$ and $Y^2$ are independently OR, wherein each R is independently selected from H, an alkyl, a substituted alkyl, an acyl and a substituted acyl. In some embodiments of formula (II), $Y^1$ and $Y^2$ are each OH. In some embodiments of formula (II), $Y^1$ and $Y^2$ are each OAc. In some embodiments of formula (II), $Y^1$ and $Y^2$ are independently $NR_2$, wherein each R is independently selected from H, an alkyl, and a substituted alkyl. In some embodiments of formula (II), $Y^1$ and $Y^2$ are each $NH_2$.

In certain instances, the linked fluorogenic dye is described by the formula (III):

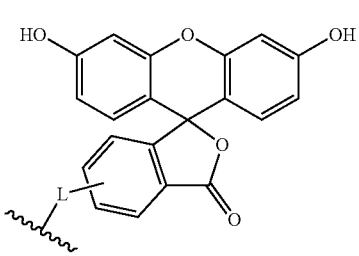

(III)

wherein L is a linker covalently attached to the multichromophore. In certain cases of formula (III), L is attached at the $R^5$ position. In certain cases of formula (III), L is attached at the $R^6$ position. In certain cases of formula (III), L is attached at the $R^7$ position.

The fluorescent dye can include a metal ion-chelating ligand and in proximity thereto a fluorogenic dye group that is configured for a ratiometric fluorescence change upon binding of the metal ion to the ligand. In certain cases, the linked fluorogenic dye is described by the formula (IV):

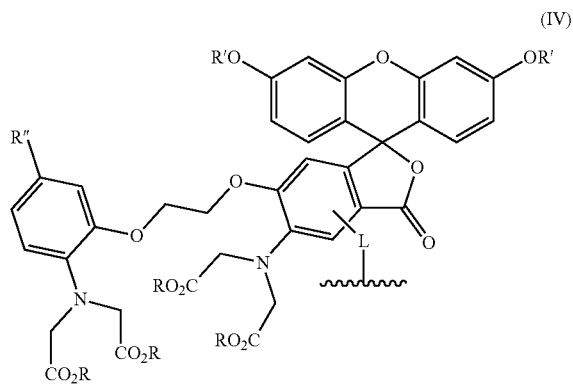

(IV)

wherein: R" is H or alkyl; each R' is H, an alkyl, a substituted alkyl, an acyl or a substituted acyl; each R is H, an alkyl or a substituted alkyl; and L is a linker covalently attached to the multichromophore. In some embodiments of formula (IV), R" is H. In some embodiments of formula (IV), R" is an alkyl. In some embodiments of formula (IV), R" is methyl. In some embodiments of formula (IV), each R is H. In some embodiments of formula (IV), each R is a substituted alkyl. In some embodiments of formula (IV), each R is an acetoxymethyl (AM) group. In some embodiments of formula (IV), each R' is a H. In some embodiments of formula (IV), each R' is an acetoxymethyl (AM) group. In some embodiments of formula (IV), each R' is an acetyl.

In certain cases, the ring-opening reaction is a hydrolysis reaction, e.g., a ring opening reaction of hydroxide ion with the lactone group. In certain instances, the subject sensor may be referred to as a pH sensor. In certain cases, the subject sensor is a sensor for hydroxide anion.

In some embodiments, the target analyte is nitric oxide. The linked fluorogenic dye can include a vicinal diamine that is configured to undergo oxidative cycloaddition with the nitric oxide target analyte. In some instances, the fluorogenic dye that senses nitric oxide is Nitirxyte Orange, as described by
Zheng et al. in "Fluorogenic and Chromogenic Rhodamine Spirolactam Based Probe for Nitric Oxide by Spiro Ring Opening Reaction" (Org. Lett., 2008, 10 (12), pp 2357-2360).

In some instances, the target analyte is a saccharide such as glucose, galactose, mannose or fructose. The linked fluorogenic dye can include any convenient boronic acid-containing dye that senses glucose, directly or indirectly. In some instances, the fluorogenic dye undergoes a reversible covalent intereaction with the cis-1,2- or 1,3-diol of a target saccharide (e.g., glucose) to form a five or six-membered cyclic ester. In certain instances, the fluorogenic sensor includes a monoboronic acid that is selective for fructose. In certain instances, the fluorogenic sensor includes a diboronic acid that is selective for glucose. Boronic acid containing fluorogenic dyes of interest include those described by Wu et al. in "Selective sensing of saccharides using simple boronic acids and their aggregates", Chem. Soc. Rev., 2013, 42, 8032-8048.

In some cases, the target analyte is a reactive oxygen species, such as hydrogen peroxide. The linked fluorogenic dye can include a boronic acid or boronic ester fluorescence-masking group that senses the target analyte. In some cases, the fluorogenic dye includes a boronate oxidation trigger that is sensitive to the analyte, e.g., hydrogen peroxide via the mechanism depicted in Scheme 1. Boronate containing fluorogenic dyes of interest include those described by Lin et al. "Boronate-Based Fluorescent Probes: Imaging Hydrogen Peroxide in Living Systems", Methods Enzymol. 2013; 526:19-43.

Scheme 1 Exemplary boronate fluorogenic dye sensing of hydrogen peroxide.

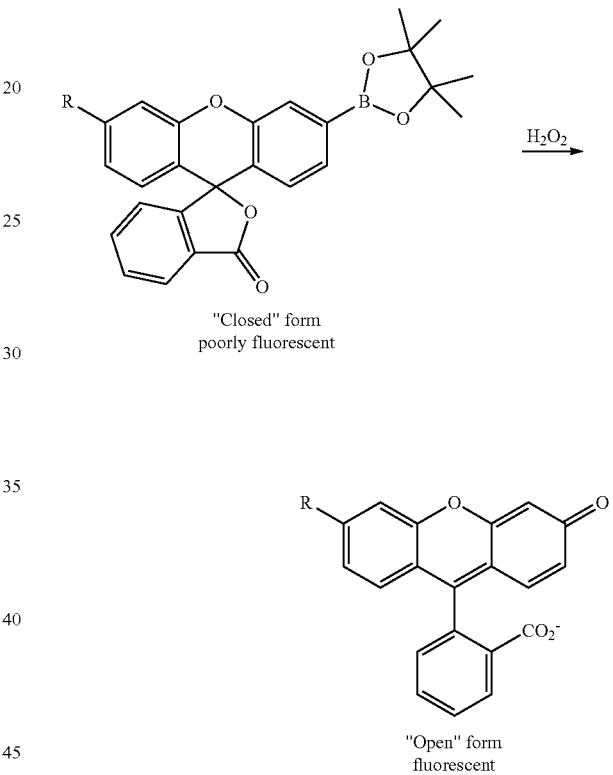

"Closed" form
poorly fluorescent

"Open" form
fluorescent

In some embodiments, the fluorogenic dye of interest which may be adapted for use in the subject sensors has one of the following structures:

PF1

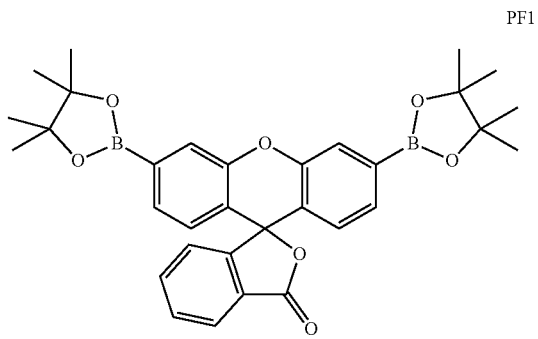

PF2
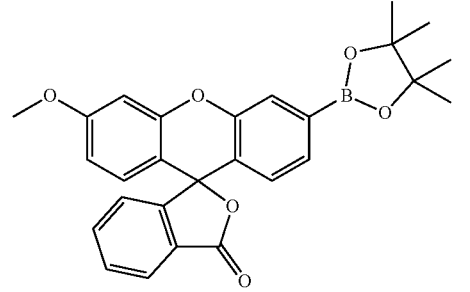

PG1
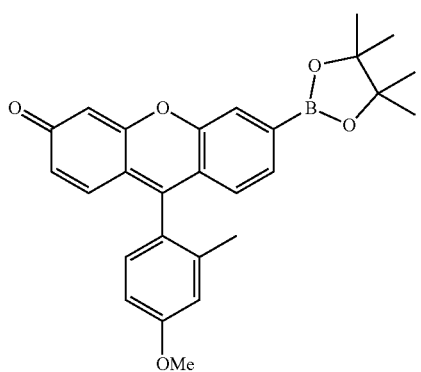

PV1
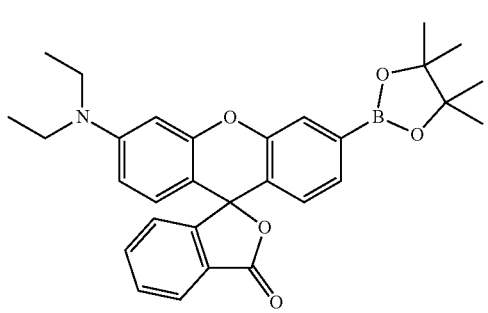

PO1
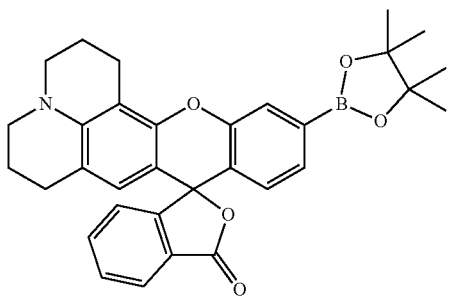

PF6-AM
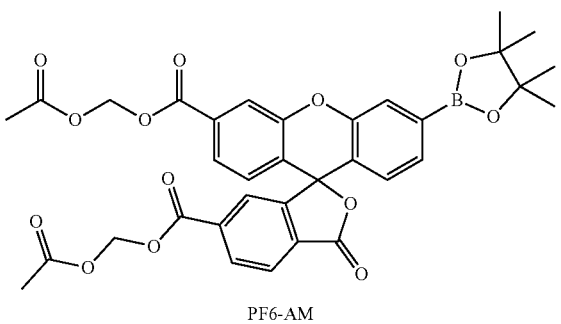

MitoPV1
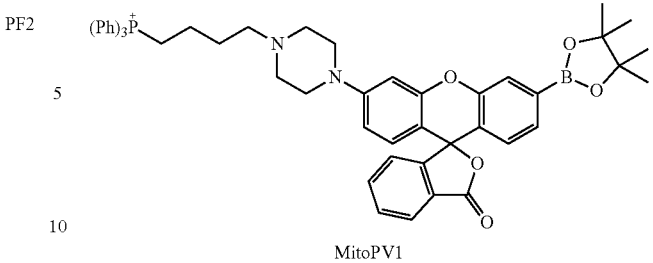

NacPE1
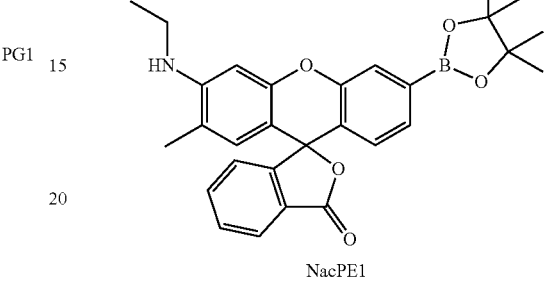

In some cases, the linked fluorogenic dye is a fluorogenic protein. In some cases, the linked fluorogenic dye is a fluorogenic protein conjugate. Fluorogenic protein conjugates include fluorescent proteins conjugated to a dye in energy receiving proximity therewith. In some cases, fluorescence quenching occurs in the unreacted protein or protein conjugate that is abrogated over the course of the reaction or interaction with a target analyte. Any convenient fluorescent proteins and conjugates thereof may be adapted for use in the subject sensors, including but not limited to those described by Chen et al. in "Fluorogenic protein labelling: a review of photophysical quench mechanisms and principles of fluorogen design", Canadian Journal of Chemistry, 2015, 93(4): 389-398, the disclosure of which is herein incorporated by reference.

In certain embodiments, the target analyte is a metal ion, such as a metal ion that is implicated in a biological process, or a toxic metal. Metal ions of interest include, but are not limited to, $Zn^{2+}$, $Fe^{2+}$, $Fe^{3+}$, $Mn^{2+}$, $Ni^{2+}$ and $Co^{2+}$. In certain cases, the metal ion analyte is a toxic metal, such as $Hg^{2+}$, $Cd^{2+}$, $Pb^{2+}$ or the like, which is suspected of being present in a sample of interest. Metal ion analytes of interest and fluorescent sensors that may be adapted for use as a fluorogenic dye in the subject sensors, include but are not limited to those described by Carter et al., "Fluorescent Sensors for Measuring Metal Ions in Living Systems", Chem. Rev., 2014, 114 (8), pp 4564-4601.

Light Harvesting Multichromophores

Aspects of the present disclosure include a light harvesting multichromophore having a conjugated segment comprising a fluorene co-monomer. As used herein, the terms "light harvesting multichromophore", "polymeric dye" and "conjugated polymer" are used interchangeably and refer to a conjugated polymer which has a structure capable of harvesting light with a particular absorption maximum wavelength and converting it to emitted light at a longer emission maximum wavelength. In some cases, the light harvesting multichromophore is itself fluorescent. Conjugated polymers (CPs) are characterized by a delocalized electronic structure and may have an effective conjugation length that is substantially shorter than the length of the polymer chain, because the backbone may contain a large number of conjugated segments in close proximity. In some cases, conjugated polymers are efficient for light harvesting and provide for optical amplification via Forster energy transfer to an acceptor.

As used herein the term "unit" refers to a structural subunit of a polymer. The term unit is meant to include monomers, co-monomers, co-blocks, conjugated segments, repeating units, and the like. A "repeating unit" is a subunit of a polymer that is defined by the minimum number of distinct structural features that are required for the unit to be considered monomeric, such that when the unit is repeated n times, the resulting structure describes the polymer or a block thereof. In some cases, the polymer may include two or more different repeating units, e.g., when the polymer is a multiblock polymer, each block may define a distinct repeating unit. In some cases, a repeating unit of the polymer includes a single monomer group. In certain instances, a repeating unit of the polymer includes two or more monomer groups, i.e., co-monomer groups, such as two, three, four or more co-monomer groups. As used herein, the term "co-monomer" or "co-monomer group" refers to a structural unit of a polymer that may itself be part of a repeating unit of the polymer. In some embodiments, the conjugated polymer includes a block copolymer that is composed of blocks of polymerized monomers. In such cases, the block copolymer may be described as having distinct repeating units each corresponding to a distinct co-block of the polymer. In some cases, the polymer is a diblock copolymer that contains two different co-blocks. In such cases, the polymer may be described as including co-blocks, where each co-block may be composed of co-monomers, such as one, two, three or more co-monomers.

Any convenient light harvesting multichromophores may be adapted to include an absorbance-modifying co-monomer in order to provide a multichromophore having a desirable absorption maximum and a desirable emission maximum for use in transferring energy to a linked dye. Light harvesting multichromophores of interest that may be adapted for use in the subject sensors include, but are not limited to, those multichromophores described by Gaylord et al. in US Publication Nos. 20040142344, 20080293164, 20080064042, 20100136702, 20110256549, 20120028828, 20120252986 and 20130190193 and U.S. Pat. Nos. 8,575, 303 and 8,802,450, the disclosures of which Publications and Patents are herein incorporated by reference in their entirety; and Gaylord et al., J. Am. Chem. Soc., 2001, 123 (26), pp 6417-6418; Feng et al., Chem. Soc. Rev., 2010, 39, 2411-2419; and Traina et al., J. Am. Chem. Soc., 2011, 133 (32), pp 12600-12607, the disclosures of which are herein incorporated by reference in their entirety.

In some embodiments, the multichromophores includes a plurality of first optically active units forming a conjugated system, having an absorption wavelength (e.g., as described herein) at which the first optically active units absorb light to form an excited state. In certain instances, the multichromophore includes a conjugated polymer segment or an oligomeric structure including bandgap-lowering n-conjugated repeating units.

The subject fluorogenic sensors may include a multichromophore that comprises one or more co-monomers selected from a phenylenevinylene co-monomer, a phenyleneethynylene co-monomer, a carbazole co-monomer, a $C_2$-$C_{12}$ alkyne co-monomer, an arylene-ethynylene co-monomer, a heteroarylene-ethynylene co-monomer, an arylene co-monomer and a heteroarylene co-monomer. In some instances, the fluorogenic sensor includes a phenylenevinylene-based multichromophore (e.g., a conjugated polymer including at least 50 mol % of phenylenevinylene co-monomers). In some instances, the fluorogenic sensor includes a phenyleneethynylene-based multichromophore (e.g., a conjugated polymer including at least 50 mol % of phenyleneethynylene co-monomers). In some instances, the fluorogenic sensor includes a carbazole-based multichromophore (e.g., a conjugated polymer including at least 50 mol % of carbazole co-monomers). In some instances, the fluorogenic sensor includes a $C_2$-$C_{12}$ alkyne-based multichromophore (e.g., a conjugated polymer including at least 50 mol % of $C_2$-$C_{12}$ alkyne co-monomers). In some instances, the fluorogenic sensor includes an arylene- or heteroarylene-ethynylene-based multichromophore (e.g., a conjugated polymer including at least 50 mol % of arylene- or heteroarylene-ethynylene co-monomers). In some instances, the fluorogenic sensor includes an arylene- or heteroarylene-based multichromophore (e.g., a conjugated polymer including at least 50 mol % of arylene- or heteroarylene-co-monomers). In certain instances, in addition to the co-monomers described above, the multichromophore includes a linking co-monomer that has a linking group to which may be attached any convenient moieties of interest (e.g., a fluorogenic dye or a specific binding member).

In some instances, the polymeric tandem dye is based on a non-fluorene multichromophore (e.g., a conjugated polymer that does not include fluorene co-monomers). It is understood that any of the co-monomers described above (e.g., a phenylenevinylene co-monomer, a phenyleneethynylene co-monomer, a carbazole co-monomer, a $C_2$-$C_{12}$ alkyne co-monomer, an arylene-ethynylene co-monomer, a heteroarylene-ethynylene co-monomer, an arylene co-monomer or a heteroarylene co-monomer) could be utilized in the multichromophore formulae described herein (e.g., formulae (X), (XVII) and (XIX)-(XXIV) in place of a fluorene co-monomer (e.g., F1).

The subject multichromophores may be water soluble. Any convenient water solubilizing groups may be included in the multichromophore to provide for increased water-solubility. While the increase in solubility may vary, in some instances the increase (as compared to the compound without the WSG(s)) is 2 fold or more, e.g., 5 fold, 10 fold, 25 fold, 50 fold, 100 fold or more. The term "water solubilizing group" (WSG) refers to a group that is well solvated in aqueous environments e.g., under physiological conditions, and that imparts improved water solubility upon the molecules to which it is attached. In some embodiments, a WSG increases the solubility of the multichromophore in a predominantly aqueous solution, as compared to a control multichromophore which lacks the WSG. In some instances, the WSGs of the multichromophore are non-ionic side groups capable of imparting solubility in water in excess of 10 mg/mL. The water solubilizing groups may be any convenient hydrophilic group that is well solvated in aqueous environments. In some cases, the hydrophilic water solubilizing group is charged, e.g., positively or negatively charged. In certain cases, the hydrophilic water solubilizing group is a neutral hydrophilic group. In some embodiments, the WSG is a hydrophilic polymer, e.g., a polyethylene glycol, a cellulose, a chitosan, or a derivative thereof.

Water solubilizing groups of interest include, but are not limited to, carboxylate, phosphonate, phosphate, sulfonate, sulfate, sulfinate, sulfonium, ester, polyethylene glycols (PEG) and modified PEGs, hydroxyl, amine, ammonium, guanidinium, pyridinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —SO$_3$M', —PO$_3$M', —NR$_3{}^+$, Y', (CH$_2$CH$_2$O)$_p$R and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —(CH$_2$CH$_2$O)$_{yy}$CH$_2$CH$_2$XR$^{yy}$, —(CH$_2$CH$_2$O)$_{yy}$CH$_2$CH$_2$X—, —X(CH$_2$CH$_2$O)$_{yy}$CH$_2$CH$_2$—, glycol, and polyethylene glycol, wherein yy is selected from 1 to 1000, X is selected from O, S, and NR$^{ZZ}$, and R$^{ZZ}$ and R$^{YY}$ are independently selected from H and C$_{1-3}$ alkyl. In some cases, a WSG is (CH$_2$)$_x$(OCH$_2$CH$_2$)$_y$OCH$_3$ where each x is independently an integer from 0-20, each y is independently an integer from 0 to 50.

Multiple WSGs may be included at a single location in the subject multichromophores via a branching linker. In certain embodiments, the branching linker is an aralkyl substituent, further di-substituted with water solubilizing groups. As such, in some cases, the branching linker group is a substituent of the multichromophore that connects the multichromophore to two or more water solubilizing groups. In some cases, the incorporation of multiple WSGs via branching linkers imparts a desirable solubility on the multichromophore. In some embodiments, the multichromophore includes one or more substituents selected from an alkyl group, an aralkyl group and a heterocyclic group, where such groups are further substituted with a water solubilizing, hydrophilic polymer group, such as a polyethylglycol (PEG) (e.g., a PEG group of 2-20 units). In some instances, the WSG is a non-ionic sidechain group capable of imparting solubility in water in excess of 10 mg/mL.

In certain embodiments, the multichromophore has an absorption maximum wavelength of 500 nm or less, such as a wavelength of 450 nm or less, 440 nm or less, 430 nm or less, 420 nm or less, 410 nm or less, 400 nm or less, or even less. In certain embodiments, the multichromophore absorbs only UV light. In certain instances, the multichromophore has an absorption maximum wavelength in the range of 300 nm to 400 nm. In certain instances, the multichromophore has an absorption maximum wavelength in the range of 400 nm to 450 nm. In certain instances, the multichromophore has an absorption maximum wavelength in the range of 450 nm to 500 nm. In certain instances, the multichromophore has an absorption maximum wavelength in the range of 500 nm to 550 nm. In some instances, the multichromophore has an emission maximum wavelength in the range of 375 to 900 nm (such as in the range of 380 nm to 900 nm, 390 nm to 900 nm, 400 nm to 900 nm, 450 nm to 900 nm, 500 nm to 900 nm, 550 nm to 900 nm, 550 nm to 900 nm, or 600 nm to 900 nm).

The multichromophore may have any convenient length. In some cases, the particular number of monomeric repeating units or segments of the multichromophore may fall within the range of 2 to 500,000, such as 2 to 100,000, 2 to 30,000, 2 to 10,000, 2 to 3,000 or 2 to 1,000 units or segments, or such as 5 to 100,000, 10 to 100,000, 100 to 100,000, 200 to 100,000, or 500 to 50,000 units or segments. In some instances, the particular number of monomeric repeating units or segments of the multichromophore may fall within the range of 2 to 1,000, such as 2 to 500, 2 to 100, 3 to 100, 4 to 100, 5 to 100, 6 to 100, 7 to 100, 8 to 100, 9 to 100 or 10 to 100 units or segments.

The multichromophore may be of any convenient molecular weight (MW). In some cases, the MW of the multichromophore may be expressed as an average molecular weight. In some instances, the polymeric dye has an average molecular weight in the range of 500 to 500,000, such as from 1,000 to 100,000, from 2,000 to 100,000, from 10,000 to 100,000 or even an average molecular weight in the range of 50,000 to 100,000.

In some embodiments, the absorbance-modifying co-monomer constitutes 5% or more by molarity (e.g., 10 mol %) of the multichromophore, such as 10% or more, 15% or more, 20% or more, 25% or more, 30% or more, 40% or more, 45% or more, 50% or more, 60% or more, 70% or more, or even more by molarity of the multichromophore. In such cases, the multichromophore may include 5 or more repeating units, such as 10 or more, 20 or more, 30 or more, 40 or more, 50 or more, 60 or more, 70 or more, 80 or more, 90 or more, 100 or more, 200 or more, 500 or more, 1000 or more, 3000 or more, 10,000 or more, or even more repeating units. In such cases, the multichromophore may include 5 or more co-monomer units, such as 10 or more, 20 or more, 30 or more, 40 or more, 50 or more, 60 or more, 70 or more, 80 or more, 90 or more, 100 or more, 200 or more, 500 or more, 1000 or more, 3000 or more, 10,000 or more, or even more co-monomer units. In certain embodiments, the absorbance-modifying co-monomer constitutes 25% or more by molarity of the multichromophore, such as 30% or more, 40% or more, 45% or more, 50% or more, or even more by molarity of the multichromophore, which includes 5 or more repeating units, such as 10 or more, 20 or more, 30 or more, 40 or more, 50 or more, 60 or more, 70 or more, 80 or more, 90 or more, 100 or more repeating units.

The subject multichromophore may have one or more desirable spectroscopic properties, such as a particular absorption maximum wavelength, a particular emission maximum wavelength, extinction coefficient, quantum yield, and the like. In some embodiments, the multichromophore has an emission maximum wavelength in the range of 300 to 900 nm, such as 350 to 850 nm, 350 to 600 nm, 360 to 500 nm, 370 to 500 nm, 380 to 500 nm, 390 to 500 nm or 400 to 500 nm, where specific examples of emission maxima of interest include, but are not limited to: 395 nm±5 nm, 460 nm±5 nm, 490 nm±5 nm, 550 nm±5 nm, 560 nm±5 nm, 605 nm±5 nm, 650 nm±5 nm, 680 nm±5 nm, 700 nm±5 nm, 805 nm±5 nm. In certain instances, the multichromophore has an emission maximum wavelength selected from the group consisting of 395 nm, 460 nm, 490 nm, 550 nm, 560 nm, 605 nm, 650 nm, 680 nm, 700 nm and 805 nm. In certain instances, the multichromophore has an emission maximum wavelength of 395 nm±5 nm. A multichromophore having a desirable emission maximum wavelength can be selected to provide for efficient energy transfer to a linked fluorogenic dye or fluoresecent dye product thereof. For example, the linked fluorogenic dye and/or fluoresecent dye product thereof can be selected to have an absorption spectra that is compatible with the emission spectra of the multichromophore to which it is attached.

In some instances, the multichromophore has an extinction coefficient of $5\times10^5$ cm$^{-1}$M$^{-1}$ or more, such as $6\times10^5$ cm$^{-1}$M$^{-1}$ or more, $7\times10^5$ cm$^{-1}$M$^{-1}$ or more, $8\times10^5$ cm$^{-1}$M$^{-1}$ or more, $9\times10^5$ cm$^{-1}$M$^{-1}$ or more, such as $1\times10^6$ cm$^{-1}$M$^{-1}$ or more, $1.5\times10^6$ cm$^{-1}$M$^{-1}$ or more, $2\times10^6$ cm$^{-1}$M$^{-1}$ or more, $2.5\times10^6$ cm$^{-1}$M$^{-1}$ or more, $3\times10^6$ cm$^{-1}$M$^{-1}$ or more, $4\times10^6$ cm$^{-1}$M$^{-1}$ or more, $5\times10^6$ cm$^{-1}$M$^{-1}$ or more, $6\times10^6$ cm$^{-1}$M$^{-1}$ or more, $7\times10^6$ cm$^{-1}$M$^{-1}$ or more, or $8\times10^6$ cm$^{-1}$M$^{-1}$ or more. In such cases, the multichromophore may have 5 or more repeating units, such as 6 or more, 7 or more, 8 or more, 9 or more, 10 or more, or even more repeating units. In some embodiments, the multichromophore has a molar extinction coefficient of $5\times10^5$ M$^{-1}$ cm$^{-1}$ or more. In certain embodiments, the multichromophore has a molar extinction coefficient of $1 \times 10^6$ $M^{-1}$ $cm^{-1}$ or more.

In some instances, the multichromophore has an extinction coefficient of 40,000 $cm^{-1}M^{-1}$ per repeating unit or more, such as 45,000 $cm^{-1}M^{-1}$ per repeating unit or more, 50,000 $cm^{-1}M^{-1}$ per repeating unit or more, 55,000 $cm^{-1}M^{-1}$ per repeating unit or more, 60,000 $cm^{-1}M^{-1}$ per repeating unit or more, 70,000 $cm^{-1}M^{-1}$ per repeating unit or more, 80,000 $cm^{-1}M^{-1}$ per repeating unit or more, 90,000 $cm^{-1}M^{-1}$ per repeating unit or more, 100,000 $cm^{-1}M^{-1}$ per repeating unit or more, or even more. In some instances, the 40,000 $cm^{-1}M^{-1}$ per repeating unit or more described herein is an average extinction coefficient. In certain instances, the repeat unit of the multichromophore may include a single monomer, two co-monomers, or three or more co-monomers. In some instances, the multichromophore has an extinction coefficient of 40,000 $cm^{-1}M^{-1}$ per co-monomer or more, such as 45,000 $cm^{-1}M^{-1}$ per co-monomer or more, 50,000 $cm^{-1}M^{-1}$ per co-monomer or more, 55,000 $cm^{-1}M^{-1}$ per co-monomer or more, 60,000 $cm^{-1}M^{-1}$ per co-monomer or more, 70,000 $cm^{-1}M^{-1}$ per co-monomer or more, 80,000 $cm^{-1}M^{-1}$ per co-monomer or more, 90,000 $cm^{-1}M^{-1}$ per co-monomer or more, 100,000 $cm^{-1}M^{-1}$ per co-monomer or more, or even more. In some instances, the 40,000 $cm^{-1}M^{-1}$ per co-monomer or more is an average extinction coefficient.

It is understood that in some cases the subject multichromophores may include co-blocks (e.g., n and m co-blocks). The subject multichromophores may include any convenient linear arrangements of n and m co-blocks of various lengths within the structure of the overall polymer. In addition, the multichromophores may include any convenient arrangements of co-monomers within such n and/or m co-blocks. A variety of polymer synthesis methods may be utilized to prepare co-monomers and co-blocks of interest in the preparation of the subject multichromophores. It is understood that in some cases, the polymerization methods may produce a composition including a population of conjugated polymers that includes some variation with respect to the particular length and/or terminal groups (i.e., end groups) present in each conjugated polymer of the population. The formulae depicted herein may refer to a single compound or to a population or sub-population of polymeric compounds.

In some instances, the multichromophore is described by formula (X):

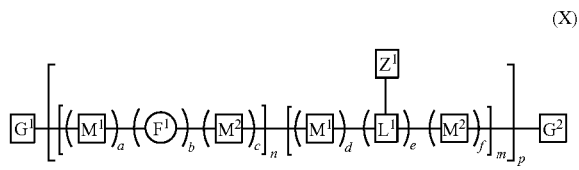

(X)

where:

$F^1$ is a fused 6-5-6 tricyclic co-monomer (e.g., a fluroene co-monomer);

each $M^1$ and $M^2$ are each independently a co-monomer (e.g., an absorbance-modifying co-monomer);

$L^1$ is a linking co-monomer substituted with a linked fluorogenic dye ($Z^1$);

e is 1;

a, b, c, d and f are each independently 0 or 1, wherein a+b+c+d+f≥1;

each n is 0 or an integer from 1 to 100,000;

each m is 0 or an integer from 1 to 10,000;

p is an integer from 1 to 100,000; and $G^1$ and $G^2$ are each independently selected from the group consisting of a terminal group, a π conjugated segment, a linker and a linked specific binding member. In some instances of formula (X), $F^1$ is a fluorene co-monomer. In some instances of formula (X), $F^1$ is a carbazole co-monomer. In certain embodiments of formula (X), $L^1$ is a carbazole co-monomer. In some instances of formula (X), $M^1$ is a fluorene co-monomer. In some cases of formula (X), the linking co-monomer is a fluorene co-monomer. In certain embodiments of formula (X), $L^1$ is an absorbance modifying co-monomer (e.g., as described herein). In certain embodiments of formula (X), $M^1$ is an absorbance modifying co-monomer (e.g., as described herein). In certain embodiments of formula (X), $M^2$ is an absorbance modifying co-monomer (e.g., as described herein).

In some embodiments of formula (X), b is 1. In some instances of formula (X), a is 0. In some cases of formula (X), c is 0. In some instances of formula (X), a is 1. In some cases of formula (X), c is 1. In some instances of formula (X), a+c is ≥1. In certain embodiments of formula (X), d is 0. In certain cases of formula (X), f is 0. In certain embodiments of formula (X), d is 1. In certain cases of formula (X), f is 1. In some instances of formula (X), d+f is ≥1. In some embodiments of formula (X), a+c+d+f=1 (i.e., a is 1, c is 1, d is 1 or f is 1). In some embodiments of formula (X), a+c+d+f=2. In some embodiments of formula (X), a+c+d+f=3. In some embodiments of formula (X), a+c+d+f=4. In certain embodiments of formula (X), e is 1 and d or f is 1, such that d+e+f=2. In certain instances of formula (X), e is 1 and d and f are each 0. In certain instances, e is 1, d+f≤1 and m≥1. In certain instances, e is 1, d and f are each 0 and m≥1. In certain instances, e is 1; d+f=1 and m≥1. In some cases, d is 1 and f is 0. In some cases, d is 0 and f is 1. In some embodiments of formula (X), n, m and p are selected such that the multichromophore includes 2 to 100,000 repeat units (i.e., monomeric repeat units) in total, where the multichromophore may include a variety of distinct monomeric repeat units. In some instances, when m is 0, p is 1 and n is 2 to 100,000. In some embodiments of formula (X), $L^1$ is a fluorene co-monomer. It is understood that the conjugated polymer of formula (X) can also be represented by a formula that provides mol % values for each co-monomer in the polymer.

A fused 6-5-6 tricyclic co-monomer is a co-monomer including a tricyclic aromatic group having three fused rings in the configuration 6-5-6, i.e. two benzo ring fused to a central 5 membered ring. The 5-membered ring can be a carbocycle or a heterocycle and can further include a side-chain substituent at the ring atom that is not fused to a benzo ring (i.e., at $Y^{11}$). In certain instances, the fused 6-5-6 tricyclic co-monomer that finds use in the subject multichromophore is described by the following formula (XI):

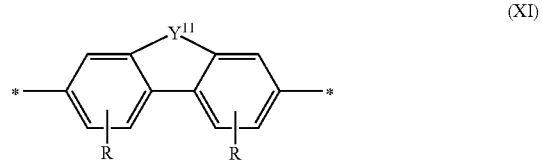

(XI)

where:

$Y^{11}$ is —$C(R^1)_2$— or —$N(R^1)$—;

each R is independently H or one or more aryl substituents (e.g., as described herein); and each $R^1$ is independently selected from the group consisting of an alkyl, a substituted alkyl, an aralkyl, a substituted aralkyl, a PEG moiety and -$L^2$-$Z^2$, where $L^2$ is a linker and $Z^2$ is a chemoselective tag (e.g., a tag including a chemoselective functional group), a WSG or a linked fluorogenic dye. In some embodiments, when $Y^{11}$ is —N($R^1$)—, the fused 6-5-6 tricyclic co-monomer is a carbazole co-monomer. Any convenient carbazole co-monomers may be utilized in the subject multichromophores. In some embodiments, when $Y^{11}$ is —C($R^1$)$_2$—, the fused 6-5-6 tricyclic co-monomer is a fluorene co-monomer. Any convenient fluorene co-monomers may be utilized in the subject multichromophores.

A fluorene co-monomer is a co-monomer including an aromatic group having a 9H-fluorene core structure substituted at the 9 position with any convenient sidechain substituent(s). In some cases, the fluorene co-monomer is a 9,9-disubstituted fluorene. The fluorene co-monomer is conjugated to adjacent polymeric backbone groups via any convenient positions of the fluorene core structure, such as any two positions of positions 1-8 (see numbering scheme below). In some embodiments, the fluorene core structure is linked to adjacent groups of the polymer backbone via the 2 and 7 positions. In certain embodiments, the fluorene co-monomer is described by the following formula (XII):

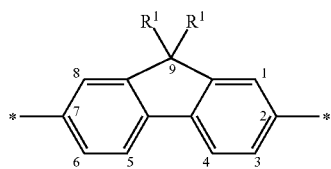

(XII)

where: each $R^1$ is independently selected from the group consisting of an alkyl, a substituted alkyl, an aralkyl, a substituted aralkyl, a PEG moiety and -$L^2$-$Z^2$, where $L^2$ is a linker and $Z^2$ is a chemoselective tag (e.g., a tag including a chemoselective functional group), a WSG or a linked fluorogenic dye. In some cases, $Z^2$ is a chemoselective tag that finds use in covalently linking the multichromophore to an acceptor fluorogenic dye (e.g., as described herein). In certain embodiments, $L^2$ is a branched linker (e.g., a substituted benzyl group) that links to two or more $Z^2$ groups (e.g., WSGs such as PEG groups of 2-20 polyethylene glycol units). As used in the formula herein, * denotes a site for covalent attachment to unsaturated backbone of a conjugated polymer or a terminal group.

In certain instances, the fluorene co-monomer is described by the formula (XIII):

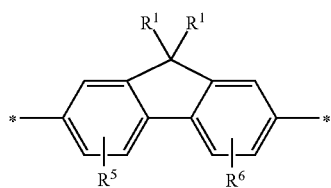

(XIII)

where: each $R^1$ is as defined above; and $R^5$ and $R^6$ are independently selected from the group consisting of H, a water solubilizing group (WSG), or an aryl substituent (e.g., as described herein).

In some instances, the fluorene co-monomer is described by the formula (XIV):

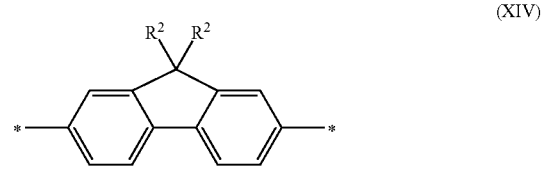

(XIV)

where each $R^2$ is a alkyl substituted with a water solubilizing group or a branched linker connected to two or more water solubilizing groups (e.g., a PEG-disubstituted benzyl or a PEG substituted alkyl). In certain embodiments, the fluorene co-monomer is described by the following formula (XV):

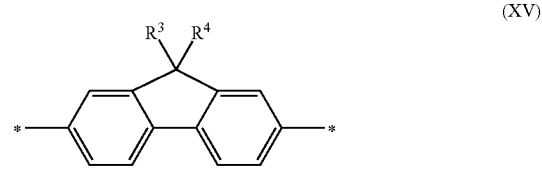

(XV)

where $R^3$ is an alkyl or an aralkyl substituted with a water solubilizing group (e.g., a PEG substituted alkyl or aralkyl), and $R^4$ is $L^2$-$Z^2$ wherein $L^2$ is a linker and $Z^2$ is a chemoselective tag or a linked fluorogenic dye. In some instances, the fluorene co-monomer is described by the formula (XVI):

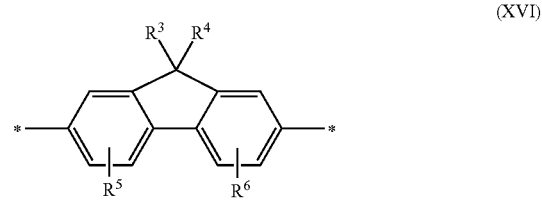

(XVI)

wherein:

$R^3$ is a substituent comprising a water solubilizing group;

$R^4$ is $L^2$-$Z^2$ wherein $L^2$ is a linker and $Z^2$ is a chemoselective tag (e.g., for conjugation to an fluorogenic dye); and $R^5$ and $R^6$ are independently selected from the group consisting of H, a water solubilizing group and an aryl substituent (e.g., an alkyl, a substituted alkyl, an alkoxy, a substituted alkoxy, a halogen or a nitro).

In some embodiments of formula (X), a, c, d and f are each 0 and b and e are each 1. In certain embodiments of formula (X), $F^1$ is a fluorene co-monomer of formula (XIV) as described herein, where each $R^2$ is independently an alkyl substituted with a water solubilizing group, such as each $R^2$ is —(CH$_2$)x(OCH$_2$CH$_2$)yOCH$_3$ where each x is independently 0 or an integer from 1-20, each y is independently 0 or an integer from 1 to 50. In certain embodiments of formula (X), $L^1$ is a fluorene co-monomer of formula (XV) as described herein. In some embodiments of formula (X), at least one of $G^1$ and $G^2$ is a substituted aryl group, e.g., an aryl group substituted with a linker (e.g., a C1-C6 alkyl linker) terminated with a carboxylic acid functional group.

In some instances of formula (X):

a, c, d and f are each 0 and b and e are each 1;

$F^1$ is a fluorene co-monomer of formula (XIV) where each $R^2$ is independently an alkyl substituted with a water solubilizing group, such as each $R^2$ is $-(CH_2)x(OCH_2CH_2)yOCH_3$ where each x is independently 0 or an integer from 1-20, each y is independently 0 or an integer from 1 to 50;

$L^1$ is a fluorene co-monomer of formula (XV) where $R^3$ is an alkyl or an aralkyl substituted with a water solubilizing group (e.g., a PEG substituted alkyl or aralkyl), and $R^4$ is $L^2-Z^2$ wherein $L^2$ is a linker and $Z^2$ is a chemoselective tag (e.g., an amino group, $-NH_2$) or a linked metal complex;

at least one of $G^1$ and $G^2$ is a substituted aryl group, e.g., an aryl group substituted with a linker (e.g., a C1-C6 alkyl linker) terminated with a carboxylic acid functional group or a linked specific binding member (e.g., as described herein).

In some cases, the multichromophores include, as part of the polymeric backbone, the following formula (XVII):

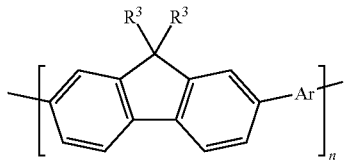

(XVII)

where each $R^3$ is independently a water solubilizing group connected via an optional linker, or an optionally substituted alkyl, aralkyl or aryl group; Ar is an optionally substituted aryl or heteroaryl group; and n is an integer from 1 to 100,000. In certain embodiments, each $R^3$ is independently a substituted alkyl group. In certain embodiments, each $R^3$ is independently a substituted aralkyl group. In some cases, each $R^3$ and each Ar are independently substituted (via an optional linker) with a water solubilizing group, an acceptor chromophore (e.g., a fluorogenic dye), a chemoselective functional group or a specific binding moiety.

In some embodiments of formulae (XI)-(XVII), one or more of $R^1$, $R^2$, $R^3$ and/or $R^4$ is independently selected from $(CH_2)_x(OCH_2CH_2)_yOCH_3$ where each x is independently an integer from 0-20, each y is independently an integer from 0 to 50; and a benzyl optionally substituted with one or more halogen, hydroxyl, $C_1$-$C_{12}$ alkoxy, or $(OCH_2CH_2)_zOCH_3$ where each z is independently an integer from 0 to 50. In some instances, each one or more of $R^1$, $R^2$, $R^3$ and/or $R^4$ is $(CH_2)_3(OCH_2CH_2)_{11}OCH_3$. In some embodiments of formulae (XI)-(XVII), one or more of $R^1$, $R^2$, $R^3$ and/or $R^4$ is a benzyl substituted with at least one WSG groups (e.g., one or two WSG groups) selected from $(CH_2)_x(OCH_2CH_2)_yOCH_3$ where each x is independently an integer from 0-20 and each y is independently an integer from 0 to 50.

As used herein, the terms "chemoselective functional group" and "chemoselective tag" are used interchangeably and refer to a functional group that can selectively react with another compatible functional group to form a covalent bond, in some cases, after optional activation of one of the functional groups. Chemoselective functional groups of interest include, but are not limited to, thiols and maleimide or iodoacetamide, amines and carboxylic acids or active esters thereof, as well as groups that can react with one another via Click chemistry, e.g., azide and alkyne groups (e.g., cyclooctyne groups), as well as hydroxyl, hydrazido, hydrazino, aldehyde, ketone, azido, alkyne, phosphine, epoxide, and the like.

Any convenient linking co-monomers ($L^1$) may be incorporated into the subject multichromophores to provide for a linking group to which may be attached any convenient moieties of interest (e.g., a linked fluorogenic dye). Linking co-monomers of interest include, but are not limited to, a fluorene co-monomer (e.g., as described herein), a phenylenevinylene co-monomer, a phenyleneethynylene co-monomer, a carbazole co-monomer, a $C_2$-$C_{12}$ alkyne co-monomer, an arylene-ethynylene co-monomer, a heteroarylene-ethynylene co-monomer, an arylene co-monomer and a heteroarylene co-monomer.

Any convenient chemoselective functional groups may be included in the subject multichromophores (e.g., at the $-Z^2$ and/or in the $G^1$ or $G^2$ terminal groups), including, but are not limited to, carboxylic acid, active ester (e.g., NHS or sulfo-NHS ester), amino, hydroxyl, thiol, maleimide, iodoacetyl, hydrazido, hydrazino, aldehyde, ketone, azido, alkyne, phosphine and epoxide. It is understood that in the polymeric tandem dye structures described herein, in some cases, the groups $Z^1$ and $Z^2$ appear at an equivalent position in the structure where these groups can be used interchangeably to refer to either a linked fluorogenic dye or a chemoselective functional group that is capable of subsequent conjugation to a dye.

In certain cases, the linking co-monomer is a substituted aryl co-monomer. In certain cases, the linking co-monomer is a substituted heteroaryl co-monomer. In certain cases, the linking co-monomer is a substituted or unsubstituted 1,4-phenyl, a substituted or unsubstituted 1,3-phenyl, a substituted or unsubstituted 4,4'-biphenyl, a substituted or unsubstituted 2,5-pyridyl, and a substituted or unsubstituted 2,6-pyridyl. In some instances, the linking co-monomer is a fluorene co-monomer. In certain instances, the linking co-monomer is an absorbance-modifying co-monomer (e.g., as described herein).

Any convenient end groups (e.g., $G^1$ and $G^2$) may be utilized at the terminals of the subject multichromophores. As used herein, the terms "end group" and "terminal group" are used interchangeably to refer to the groups located at the terminals of the polymeric structure of the multichromophore, e.g., as described herein. $G^1$ and $G^2$ groups of interest include, but are not limited to a terminal capping group, a π conjugated segment, a linker and a linked specific binding member. In some embodiments, a terminal capping groups is a monovalent group which is conjugated to the backbone of the multichromophore after polymerization. In certain instances, the terminal capping group is an aryl, a substituted aryl, a heteroaryl, a substituted heteroaryl, an alkyl or a substituted alkyl. In certain cases, the terminal capping group is derived from a monomer used in the method of polymerization, e.g., a terminal group such as a halogen (e.g., Br), a boronic acid or a boronic ester, which is capable of undergoing further conjugation. In some instances, $G^1$ and/or $G^2$ is a π conjugated segment. As used herein, a π conjugated segment refers to any convenient segment of a conjugated polymer to which the multichromophore may be conjugated, i.e., allowing delocalization of pi electron across adjacent units. In certain embodiments, $G^1$ and/or $G^2$ is a linker, such as a linker including a functional group suitable for conjugation to a specific binding moiety. It is understood that linkers located at the $G^1$ and/or $G^2$ positions of the multichromophore may be selected so as to be orthogonal to any other linkers including chemoselective tags that may be present at a sidechain of the multichromophore (e.g., at $Z^2$). In certain embodiments, an amino functional group or derivative thereof is included at $G^1$ and/or $G^2$ and a carboxylic acid functional group or derivative thereof is included at $Z^2$. In certain embodiments, a carboxylic acid functional group or derivative thereof is included at $G^1$ and/or $G^2$ and an amino functional group or derivative thereof is included at $Z^2$.

In some embodiments, the absorbance-modifying co-monomer is an optionally substituted aryl or heteroaryl co-monomer. Any convenient aryl or heteroaryl co-monomers may be utilized in the subject multichromophores as absorbance-modifying co-monomers. The absorbance-modifying co-monomer or band gap modifying unit may be evenly or randomly distributed along the conjugated polymer. In certain embodiments, the absorbance-modifying co-monomer is an optionally substituted co-monomer selected from 2,1,3-benzothiadiazole, 2,1,3-benzoxadiazole, benzoxidazole, benzoselenadiazole, benzotellurodiazole, naphthoselenadiazole, 4,7-di(thien-2-yl)-2,1,3-benzothiadiazole, squaraine dyes, quinoxalines, perylene, perylene diimides, diketopyrrolopyrrole, thienopyrazine low bandgap commercial dyes, olefins, and cyano-substituted olefins and isomers thereof.

In some instances, aryl and heteroaryl co-monomers which find use in the subject multichromophores are selected from a'-k' having the structure:

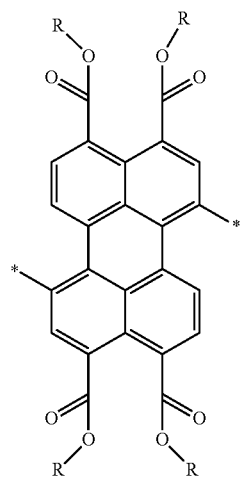

a'

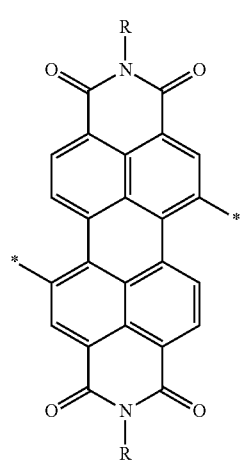

b'

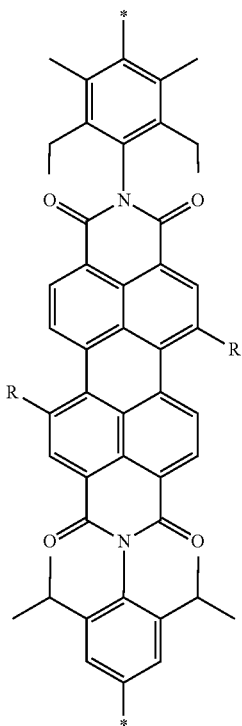

c'

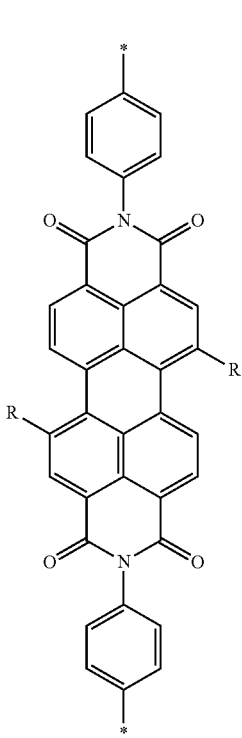

d'

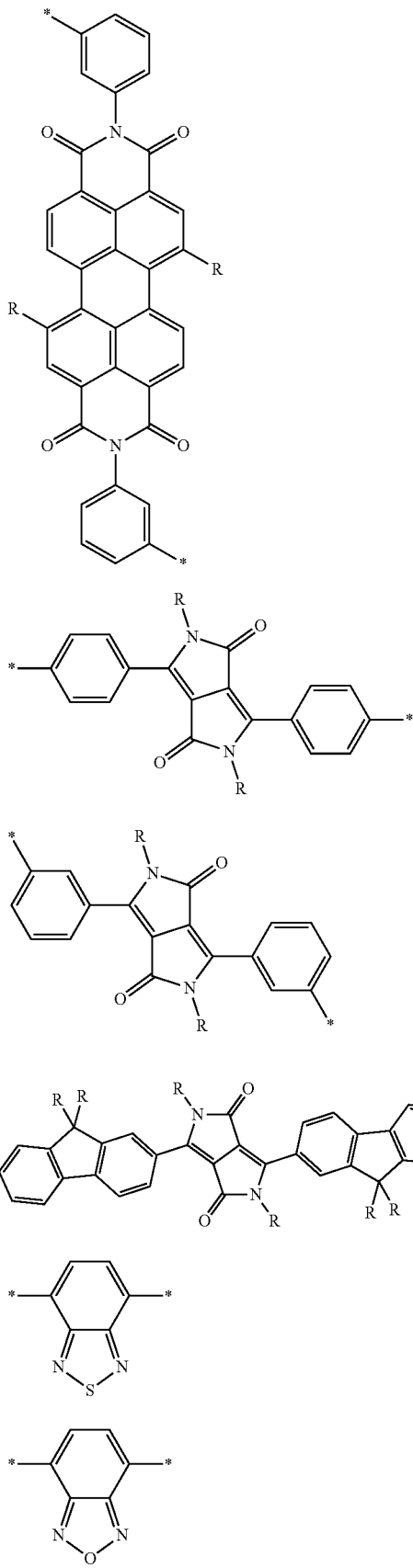

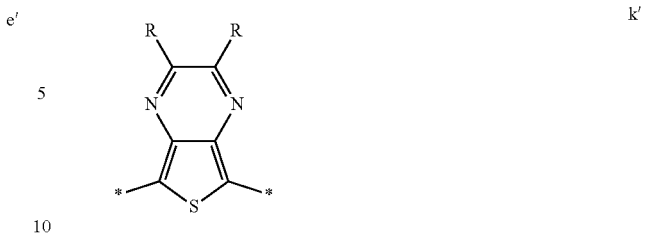

wherein *=a site for covalent attachment to unsaturated backbone and each R is independently H, a non-ionic side group capable of imparting solubility in water (e.g., a WSG), or $-L^2-Z^2$, where $L^2$ is a linker and $Z^2$ is a chemoselective tag or a linked dye. In certain instances of a'-k', each R is an alkyl or a benzyl substituted with one or more $(CH_2)_x(OCH_2CH_2)_yOCH_3$ where each x is independently an integer from 0-20, each y is independently an integer from 0 to 50. In certain instances of a'-k', each R is $(CH_2)_3(OCH_2CH_2)_{11}OCH_3$.

In certain embodiments, the multichromophore of formula (X) includes an absorbance-modifying co-monomer having the structure of one of co-monomers a'-k', as described herein. In some embodiments, the multichromophore of formula (X) includes an absorbance-modifying co-monomer having the formula (XVIII):

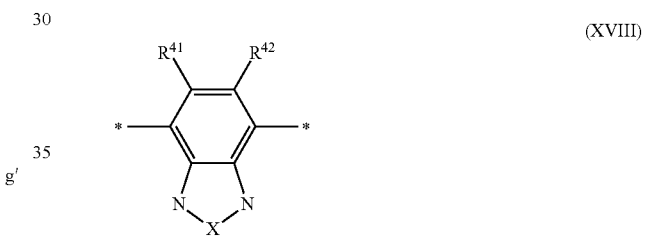

(XVIII)

where X is O or S, $R^{41}$ and $R^{42}$ are each independently, H, halogen, a WSG, an alkyl, a substituted alkyl, an alkoxy and a substituted alkoxy. In certain instances, X is O. In some instances, X is S. In certain embodiments, the absorbance-modifying co-monomer is selected from one of the following:

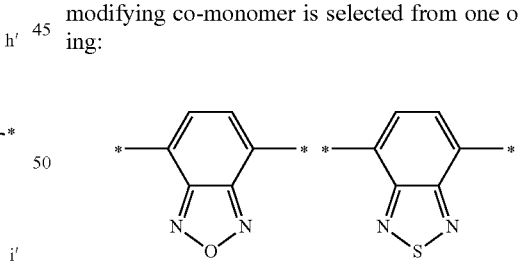

wherein *=site for covalent attachment to unsaturated backbone.

In some instances, the absorbance-modifying co-monomer is a substituted or unsubstituted phenyl, biphenyl or pyridyl co-monomer. In certain embodiments, the absorbance-modifying co-monomer is an optionally substituted aryl or heteroaryl co-monomer selected from the group consisting of substituted or unsubstituted 1,4-phenyl, a substituted or unsubstituted 1,3-phenyl, a substituted or unsubstituted 4,4'-biphenyl, a substituted or unsubstituted 2,5-pyridyl, and a substituted or unsubstituted 2,6-pyridyl. In certain instances, the absorbance-modifying co-monomer is an optionally substituted aryl or heteroaryl co-monomer selected from one of the following structures:

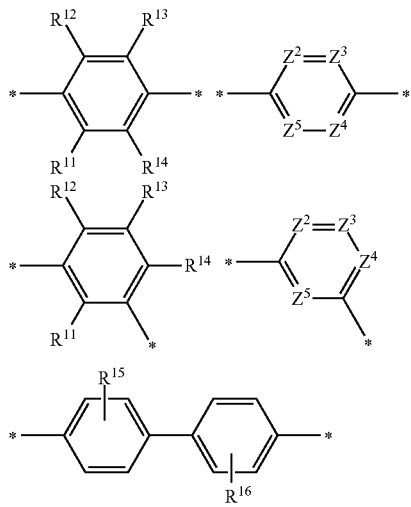

where $Z^2$-$Z^5$ are each independently CR or N, where at least one $Z^2$-$Z^5$ is N; and each R and each $R^{11}$-$R^{16}$ are independently selected from the group consisting of hydrogen, water solubilizing group, halogen, cyano, alkoxy, substituted alkoxy, alkyl and substituted alkyl. In certain embodiments, one and only one of $Z^2$-$Z^5$ is N. In certain embodiments, two and only two of $Z^2$-$Z^5$ is N. In certain instances, $R^{11}$, $R^{12}$ and $R^{14}$ are each H. In some instances, $R^{12}$ and $R^{14}$ are each H. In some instances, $R^{11}$ and $R^{13}$ are each H. In some cases, $R^{15}$ and $R^{16}$ are each H. In some instances, the halogen is fluoro.

In some cases, the absorbance-modifying co-monomer is an optionally substituted aryl or heteroaryl co-monomer selected from one of the following:

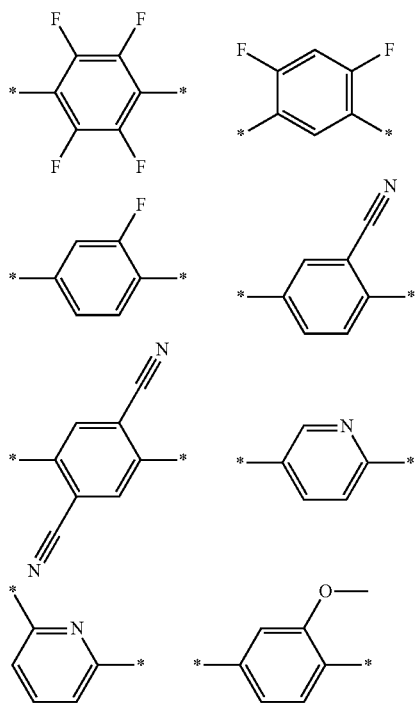

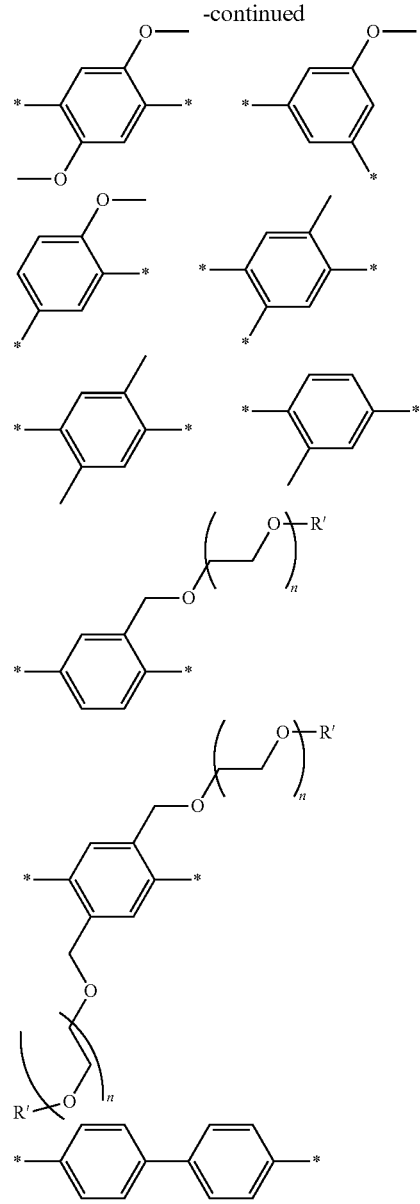

where n is 1-20 and R' is H or lower alkyl. In some embodiments of the substituted aryl or heteroaryl co-monomer structures, n is an integer from 3 to 20.

In some embodiments, the multichromophore includes a substituted aryl co-monomer described by the following structure:

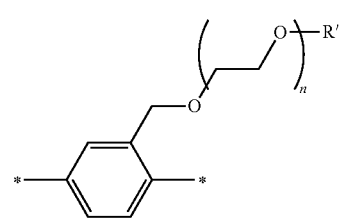

where n is 1-20 and R' is H or lower alkyl. In certain instances, n is 3 to 12.

In some embodiments, the multichromophore includes a substituted aryl co-monomer described by the following structure:

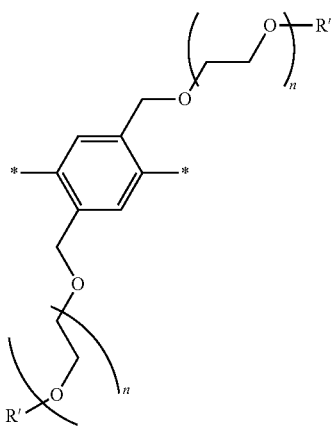

where each n is independently 1-20 and each R' is independently H or lower alkyl. In certain embodiments of the substituted aryl or heteroaryl co-monomer structures shown above, n is 3. In certain instances, R' is methyl. In certain instances, R' is hydrogen. In some embodiments, the multichromophore includes a substituted aryl co-monomer described by the following structure:

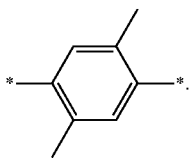

In some embodiments, the multichromophore includes a substituted aryl co-monomer described by the following structure:

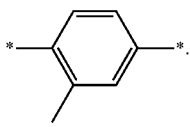

Any of the absorbance-modifying co-monomers described above may be utilized in the subject multichromophores, e.g., multichromophores of formulae (X) and (XIX)-(XX).

In some embodiments, the fluorogenic sensor is described by formula (XIX):

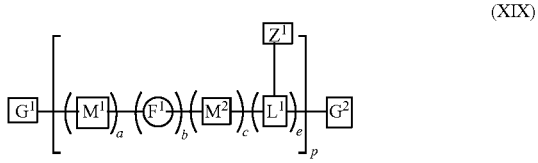

where $F^1$, $M^1$, $M^2$, a, b, c, e, $Z^1$, p, $G^1$ and $G^2$ are as described for formula (X). In some instances of formula (XIX), $F^1$ is a fluorene co-monomer. In certain instances of formula (XIX), $F^1$ is a carbazole co-monomer. In some embodiments of formula (XIX), $L^1$ is a fluorene co-monomer. In certain embodiments of formula (XIX), $L^1$ is a carbazole co-monomer. In some embodiments of formula (XIX), $L^1$ is a substituted aryl or heteroaryl co-monomer. In some embodiments of formula (XIX), $M^1$ and $M^2$ are each in dependently an absorbance modifying co-monomer (e.g., as described herein).

In some instances of formula (XIX), a and c are each 0 and b and e are each 1. In some instances of formula (XIX), b is 1 and a+c≥1. In certain instances of formula (XIX), a+c=1 (e.g., a is 1 and c is 0, or a is 0 and c is 1). In certain embodiments of formula (XIX), a+c=2. In some cases of formula (XIX), $F^1$ is a fluorene co-monomer and $L^1$ is a substituted aryl or heteraryl co-monomer. In some cases of formula (XIX), $F^1$ and $L^1$ are independently a fluorene co-monomer. In some instances of formula (XIX), $G^1$ is a terminal group; and $G^2$ is a terminal group, a linker or a linked specific binding member. In certain cases, $G^2$ is a linked specific binding member. In some cases, $G^2$ is a linker, where the linker may include a chemoselective tag.

In some instances of formula (XIX):
a and c are each 0 and b and e are each 1;
$F^1$ is a fluorene co-monomer of formula (XIV) where each $R^2$ is independently an alkyl substituted with a water solubilizing group, such as each $R^2$ is —$(CH_2)$x$(OCH_2CH_2)$y$OCH_3$ where each x is independently 0 or an integer from 1-20, each y is independently 0 or an integer from 1 to 50;
$L^1$ is a fluorene co-monomer of formula (XV) where $R^3$ is an alkyl or an aralkyl substituted with a water solubilizing group (e.g., a PEG substituted alkyl or aralkyl), and $R^4$ is $L^2$-$Z^2$ wherein $L^2$ is a linker and $Z^2$ is a chemoselective tag (e.g., an amino group, —$NH_2$) or a linked fluorogenic dye ($Z^1$);
at least one of $G^1$ and $G^2$ is a substituted aryl group, e.g., an aryl group substituted with a linker (e.g., a C1-C6 alkyl linker) terminated with a carboxylic acid functional group or a linked specific binding member (e.g., as described herein).

In some instances, the multichromophore is described by formula (XX):

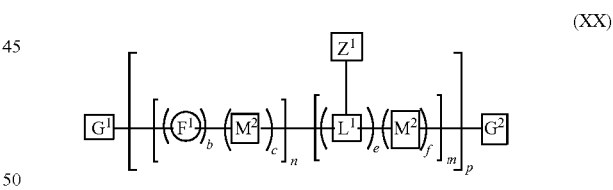

where $F^1$, $M^2$, b, c, e, f, $L^1$, $Z^1$, n, m, p, $G^1$ and $G^2$ are as described for formula (X). In some instances of formula (XX), $F^1$ is a fluorene co-monomer. In certain instances of formula (XX), $F^1$ is a carbazole co-monomer. In some embodiments of formula (XIX), $L^1$ is a fluorene co-monomer. In some embodiments of formula (XX), $L^1$ is a substituted aryl or heteroaryl co-monomer. In some embodiments of formula (XX), $M^1$ and $M^2$ are each in dependently an absorbance modifying co-monomer (e.g., as described herein).

In some embodiments of formula (XX), b is 1; c is 0 or 1; e is 1; f is 0 or 1; $G^1$ is a terminal group; and $G^2$ is a terminal group, a linker or a linked specific binding member. In certain instances of formula (XX), c is 1. In certain cases of formula (XX), c is 0. In certain instances of formula (XX), f is 1. In certain cases of formula (XX), f is 0. In certain cases, $G^2$ is a linked specific binding member. In some cases, $G^2$ is a linker, where the linker may include a chemoselective tag.

In some instances of formula (XX):

c and f are each 0 and b and e are each 1;

$F^1$ is a fluorene co-monomer of formula (XIV) where each $R^2$ is independently an alkyl substituted with a water solubilizing group, such as each $R^2$ is —(CH$_2$)x(OCH$_2$CH$_2$)yOCH$_3$ where each x is independently 0 or an integer from 1-20, each y is independently 0 or an integer from 1 to 50;

$L^1$ is a fluorene co-monomer of formula (XV) where $R^3$ is an alkyl or an aralkyl substituted with a water solubilizing group (e.g., a PEG substituted alkyl or aralkyl), and $R^4$ is $L^2$-$Z^2$ wherein $L^2$ is a linker and $Z^2$ is a chemoselective tag (e.g., an amino group, —NH$_2$) or a linked fluorogenic dye ($Z^1$);

at least one of $G^1$ and $G^2$ is a substituted aryl group, e.g., an aryl group substituted with a linker (e.g., a C1-C6 alkyl linker) terminated with a carboxylic acid functional group or a linked specific binding member (e.g., as described herein).

In some instances of formulae (X) and (XIX) to (XX), $L^1$ is described by the structure:

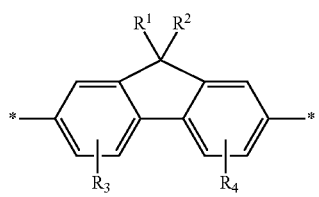

wherein:

$R^1$ is a substituent including a water solubilizing group (e.g., a PEG substituted alkyl);

$R^2$ is $L^2$-$Z^2$ wherein $L^2$ is a linker and $Z^2$ is the acceptor linked fluorogenic dye; and $R^3$ and $R^4$ are independently selected from the group consisting of H, a water solubilizing group, an alkyl, a substituted alkyl, an alkoxy, a substituted alkoxy, a halogen and a nitro. In certain instances, $R^3$ and $R^4$ are each hydrogen.

In some embodiments of formulae (X) and (XIX) to (XX), at least one of $G^1$ and $G^2$ is -$L^3$-$Z^3$ where $L^3$ is a linker (e.g., as described herein) and $Z^3$ is a specific binding member (e.g., as described herein). In some embodiments of formulae (X) and (XIX) to (XX), at least one of $G^1$ and $G^2$ is -$L^3$-$Z^3$ where $L^3$ is a linker (e.g., as described herein) and $Z^3$ is a chemoselective tag (e.g., as described herein). In some instances, $Z^3$ is selected from the group consisting of carboxylic acid, active ester (e.g., N-hydroxy succinimidyl ester (NHS) or sulfo-NHS), amino, maleimide, iodoacetyl and thiol. In certain embodiments of formulae (X) and (XIX) to (XX), at least one of $G^1$ and $G^2$ is described by the following structure:

\*-Ar-L-Z where Ar is a π-conjugated aryl group, L is a linker and Z is a chemoselective tag or a specific binding member. In certain embodiments of formulae (X) and (XIX) to (XX), at least one of $G^1$ and $G^2$ is described by the following structure:

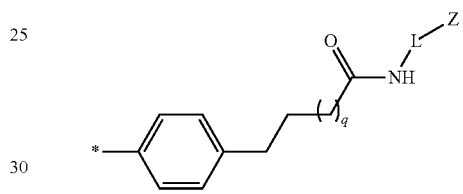

wherein:

q is 0 or an integer from 1-12;

L is an optional linker; and

Z is a chemoselective tag or a specific binding member. In certain embodiments, Z is a specific binding member that is a biomolecule. Biomolecules of interest include, but are not limited to, polypeptides, polynucleotides, carbohydrates, fatty acids, steroids, purines, pyrimidines, derivatives, structural analogs thereof and combinations thereof. In certain instances, Z is an antibody. In some instances, Z is an antibody fragment or binding derivative thereof. In some cases, the antibody fragment or binding derivative thereof is selected from the group consisting of a Fab fragment, a F(ab')$_2$ fragment, a scFv, a diabody and a triabody.

In some embodiments, the fluorogenic sensor is described by formula (XXI):

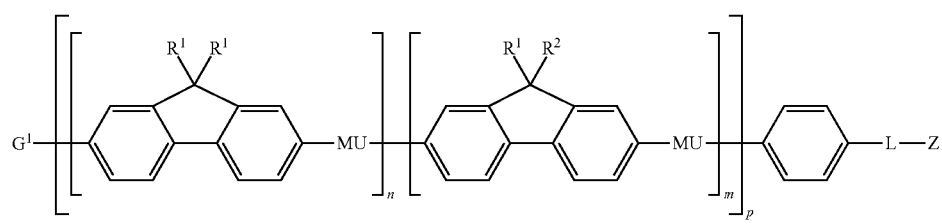

where: each $R^1$ is independently an alkyl or aralkyl substituted with one or more WSG, or a branching group further substituted with two or more WSGs; MU is an absorbance modifying co-monomer (e.g., as described herein); $R^2$ is $L^2$-$Z^2$ wherein $L^2$ is a linker and $Z^2$ is the acceptor fluorogenic dye; L is a linker and Z is a chemoselective tag or a linked specific binding member; $G^1$ is an end group; and n, m and p are each independently an integer from 1 to 100,000. In some instances, $G^1$ is an aryl end group. In some cases, $G^1$ is a phenyl. In certain embodiments, Z is selected from a carboxylic acid, an amino or a maleimide. In certain instances, Z is a linked specific binding member. In some instances, L is an alkyl-carboxylic acid, such as —$(CH_2)_3$COOH. In certain embodiments, one or more of the $R^1$ groups is a branching group further substituted with two or more WSGs. In certain instances, the branching group is a substituted aralkyl, such as a substituted benzyl group, which is disubstituted with two PEG groups.

In some embodiments, the fluorogenic sensor is described by formula (XXIII):

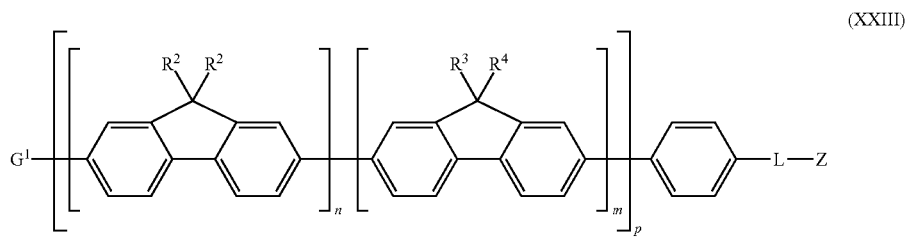
(XXIII)

where: each $R^2$ is independently an alkyl or aralkyl substituted with one or more WSG, or a branching group further substituted with two or more WSGs; $R^3$ is an alkyl or a substituted alkyl (e.g., as described herein); $R^4$ is $L^2$-$Z^2$ wherein $L^2$ is a linker and $Z^2$ is the acceptor fluorogenic dye; L is a linker and Z is a chemoselective tag or a linked specific binding member; $G^1$ is an end group; and n, m and p are each independently an integer from 1 to 100,000. In some instances, $G^1$ is an aryl end group. In some cases, $G^1$ is a phenyl. In certain embodiments, Z is selected from a carboxylic acid, an amino or a maleimide. In certain instances, Z is a linked specific binding member, L-Z is an alkyl-carboxylic acid, such as —$(CH_2)_3$COOH. In certain embodiments, one or more of the $R^2$ groups is a branching group further substituted with two or more WSGs. In certain instances, the branching group is a substituted aralkyl, such as a substituted benzyl group, which is disubstituted with two PEG groups. In some instances of formula (XXIII): each $R^2$ is independently an alkyl substituted with a water solubilizing group, such as each $R^2$ is —$(CH_2)x(OCH_2CH_2)yOCH_3$ where each x is independently 0 or an integer from 1-20, each y is independently 0 or an integer from 1 to 50; $R^3$ is an alkyl or an aralkyl substituted with a water solubilizing group (e.g., a PEG substituted alkyl or aralkyl), and $R^4$ is $L^2$-$Z^2$ wherein $L^2$ is a linker and $Z^2$ is a chemoselective tag (e.g., an amino group, —$NH_2$) or a linked fluorogenic dye ($Z^1$). In some embodiments, the fluorogenic sensor is described by formula (XXIV):

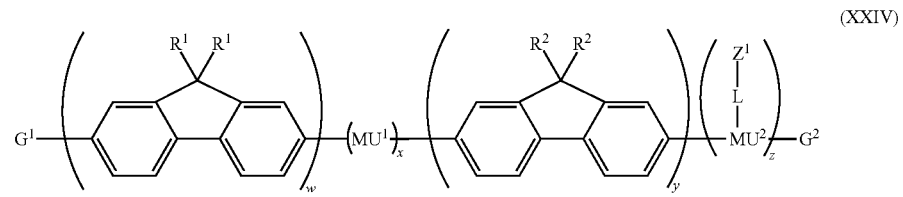
(XXIV)

where: each $R^1$ and each $R^2$ is independently an alkyl substituted with a WSG (e.g., as described herein), or a branching group further substituted with two or more WSGs (e.g., as described herein); $MU^1$ and $MU^2$ are independently an absorbance modifying co-monomer (e.g., as described herein); L is a linker and $Z^1$ is a linked metal complex; $G^1$ and $G^2$ are each independently an end group; and w, x, y and z are the mol % values of the co-monomers in the conjugated polymer.

In some embodiments, the fluorogenic sensor is described by formula (XXII):

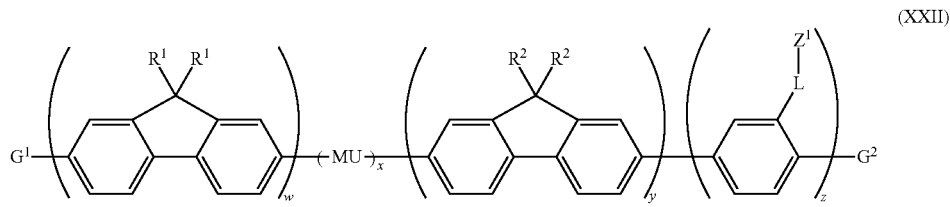

(XXII)

where: each $R^1$ and each $R^2$ is independently an alkyl substituted with a WSG, or a branching group further substituted with two or more WSGs (e.g., as described herein); MU is an absorbance modifying co-monomer (e.g., as described herein); L is a linker and $Z^1$ is a linked fluorogenic dye; $G^1$ and $G^2$ are each independently an end group; and w, x, y and z are the mol % values of the co-monomers in the conjugated polymer. In some instances, $G^1$ is an aryl end group. In some cases, $G^1$ is a substituted phenyl. In certain instances, $G^1$ or $G^2$ comprise a linked specific binding member. In some instances, L comprises an alkyl-amido, such as —$(CH_2)_3CONH$—. In certain embodiments, each $R^1$ group is a branching group further substituted with two or more WSGs. In certain instances, the branching group is a substituted aralkyl, such as a substituted benzyl group, which is substituted with two PEG groups.

In some instances of formula (XXII), w is 10 mol % or more, such as 15 mol % or more, 20 mol % or more, 25 mol % or more, or even more. In some instances of formula (XXII), x is 0. In some instances of formula (XXII), x is 10 mol % or more, such as 15 mol % or more, 20 mol % or more, 25 mol % or more, or even more. In some instances of formula (XXII), y is 0. In some instances of formula (XXII), y is 10 mol % or more, such as 15 mol % or more, 20 mol % or more, 25 mol % or more, or even more. In some instances of formula (XXII), z is 10 mol % or more, such as 15 mol % or more, 20 mol % or more, 25 mol % or more, or even more.

In some instances of the multichromophores of any one of formulae (X), (XVII) and (XIX)-(XXIV), the mol % of the luminescent metal complex acceptor units in the multichromophore (e.g., the mol % of linking co-monomers to which luminescent metal complexes are linked in the donor water soluble light harvesting) ranges from 1 mol % to 50 mol %, such as from 5 mol % to 25 mol % or from 10 mol % to 25 mol %; or such as from 5 mol % to 25 mol % or from 10 mol % to 25 mol %; or such as from 1 mol % to 25 mol %, from 1 mol % to 10 mol %, or from 1 mol % to 5 mol %.

It is understood that for any of the structures and formula depicted herein that in some cases of the subject multichromophore the end groups depicted may be located at the opposite ends to those shown, e.g., the end groups $G^1$ and -Ph-L-Z may be switched. In some embodiments of the multichromophores described herein (e.g., formulae (X), (XVII) and (XIX)-(XXIV), at least one of $G^1$ and $G^2$ is selected from one of the following structures 1-33:

1

\*—H

2

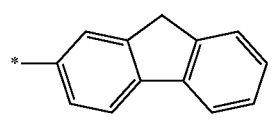

3

\*—Br

4

\*—Cl

5

\*—I

6

\*—SH

7

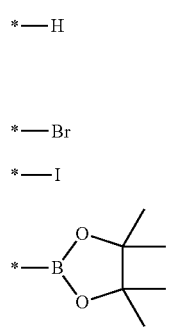

8

\*—B(OH)$_2$

9

10

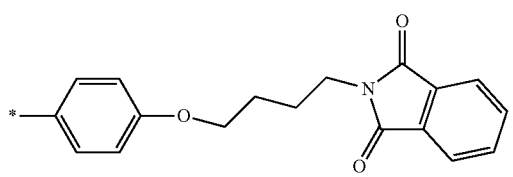

-continued
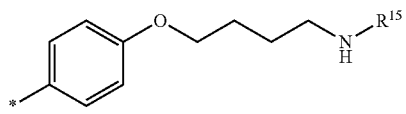
11
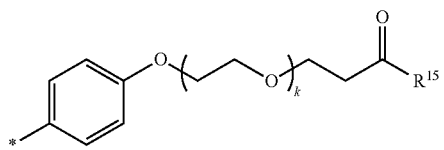
12
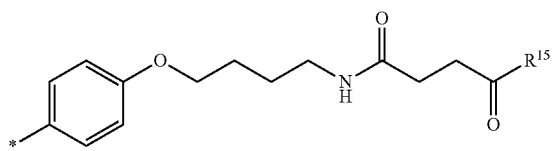
13
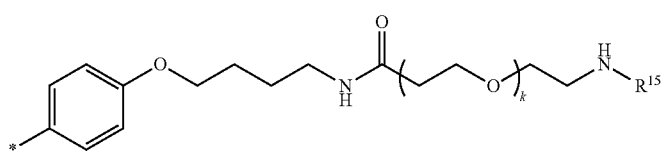
14
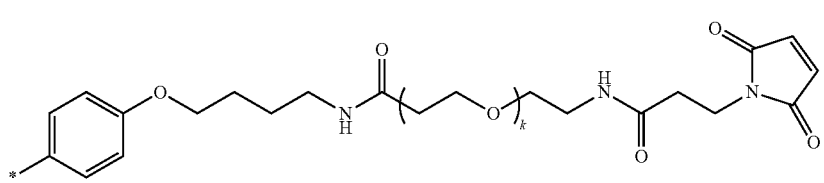
15
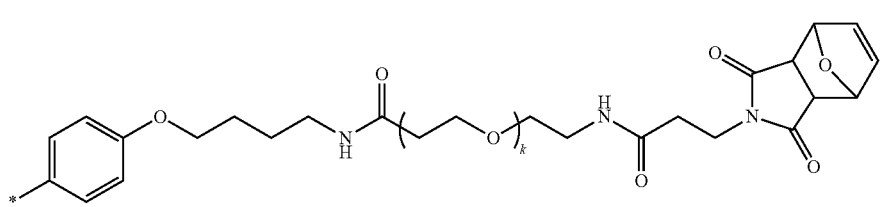
16
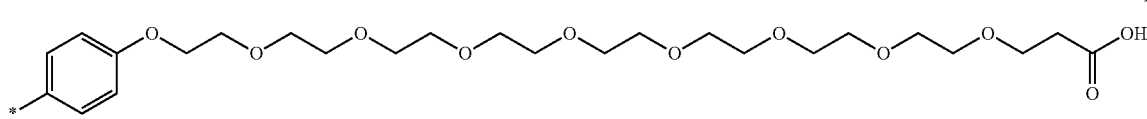
17
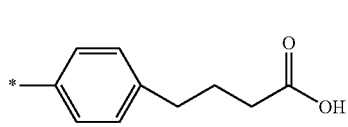
18
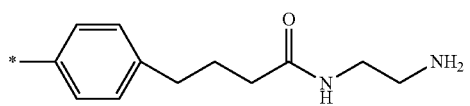
19
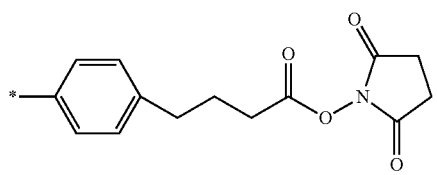
20
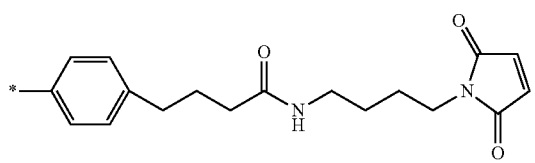
22
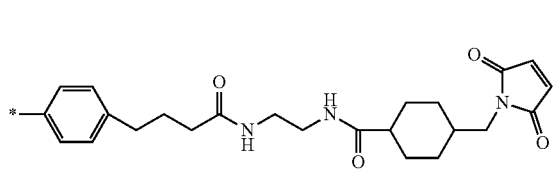
23
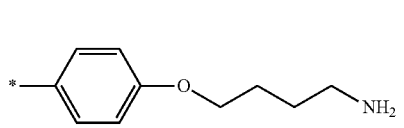
24

-continued
25
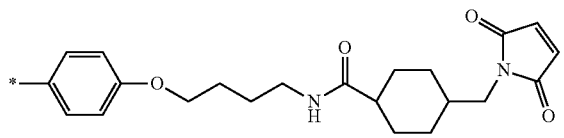
26
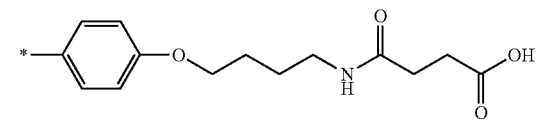
27
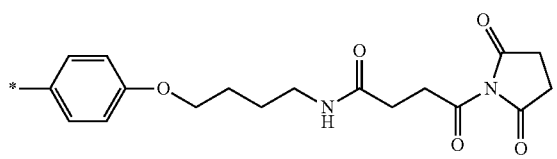
28
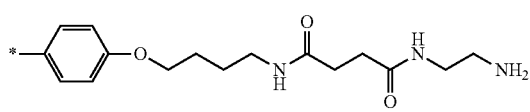
29
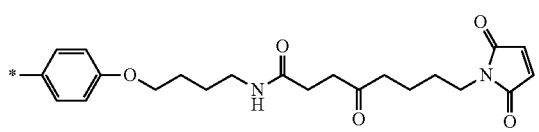
30
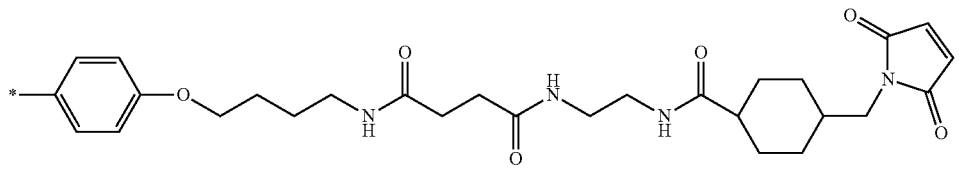
31
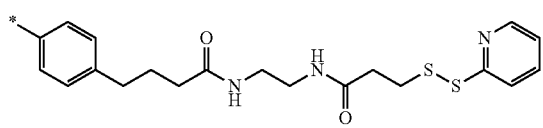
32
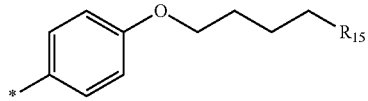
33
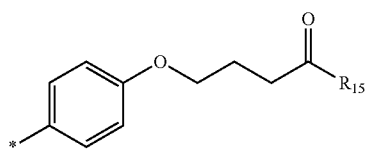
* = site for covalent attachment to unsaturated backbone;

wherein R' is independently H, halogen, $C_1$-$C_{12}$ alkyl, ($C_1$-$C_{12}$ alkyl)$NH_2$, $C_2$-$C_{12}$ alkene, $C_2$-$C_{12}$ alkyne, $C_3$-$C_{12}$cycloalkyl, $C_1$-$C_{12}$ haloalkyl, $C_2$-$C_{18}$(hetero)aryl, $C_2$-$C_{18}$(hetero)arylamino, —[$CH_2$—$CH_2$]$_{r'}$—$Z^1$, or ($C_1$-$C_{12}$)alkoxy-$X^1$; and wherein $Z^1$ is —OH or —COOH; $X^1$ is —$NH_2$, —NHCOOH, —NHCOOC($CH_3$)$_3$, —NHCO(C3-C12)cycloalkyl(C1-C4)alkyl-N-maleimide; or —NHCO[$CH_2$—$CH_2$—O]$_{s'}$($CH_2$)$_{s'}$$NH_2$; r' is an integer from 1 to 20; and each s' is independently an integer from 1 to 20, ($CH_2$)$_3$($OCH_2CH_2$)$_{x''}$$OCH_3$ where x'' is independently an integer from 0 to 50, or a benzyl optionally substituted with one or more halogen, hydroxyl, $C_1$-$C_{12}$ alkoxy, or ($OCH_2CH_2$)$_{y''}$$CH_3$ where each y'' is independently an integer from 0 to 50 and R' is different from R;

wherein k is 2, 4, 8, 12 or 24;

wherein $R^{15}$ is selected from the group consisting of I-u having the structure:

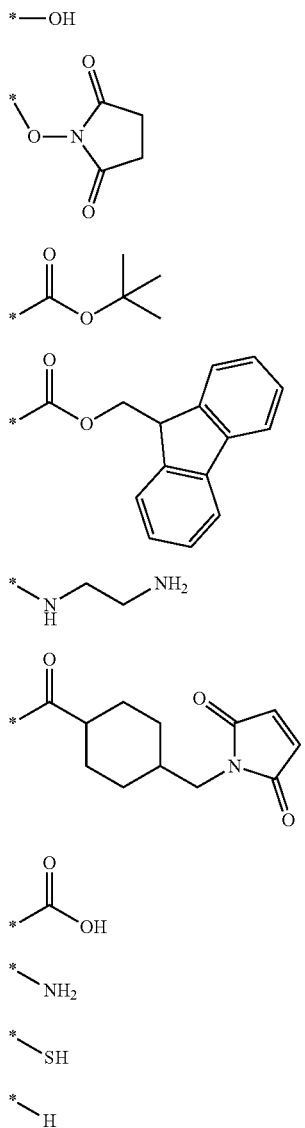

* = site for covalent attachment to backbone.

Labelled Specific Binding Members

Aspects of the present disclosure include labelled specific binding members. A labelled specific binding member is a conjugate of a subject fluorogenic sensor (e.g., as described herein) and a specific binding member. Any of the fluorogenic sensors described herein may be conjugated to a specific binding member. The specific binding member and the fluorogenic sensor can be conjugated (e.g., covalently linked) to each other at any convenient locations of the two molecules, via an optional linker.

As used herein, the term "specific binding member" refers to one member of a pair of molecules which have binding specificity for one another. One member of the pair of molecules may have an area on its surface, or a cavity, which specifically binds to an area on the surface of, or a cavity in, the other member of the pair of molecules. Thus the members of the pair have the property of binding specifically to each other to produce a binding complex. In some embodiments, the affinity between specific binding members in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. In some embodiments, the specific binding members specifically bind with high avidity. By high avidity is meant that the binding member specifically binds with an apparent affinity characterized by an apparent $K_d$ of $10\times10^{-9}$ M or less, such as $1\times10^{-9}$ M or less, $3\times10^{-10}$ M or less, $1\times10^{-10}$ M or less, $3\times10^{-11}$ M or less, $1\times10^{-11}$ M or less, $3\times10^{-12}$ M or less or $1\times10^{-12}$ M or less.

The specific binding member can be proteinaceous. As used herein, the term "proteinaceous" refers to a moiety that is composed of amino acid residues. A proteinaceous moiety can be a polypeptide. In certain cases, the proteinaceous specific binding member is an antibody. In certain embodiments, the proteinaceous specific binding member is an antibody fragment, e.g., a binding fragment of an antibody that specific binds to a polymeric dye. As used herein, the terms "antibody" and "antibody molecule" are used interchangeably and refer to a protein consisting of one or more polypeptides substantially encoded by all or part of the recognized immunoglobulin genes. The recognized immunoglobulin genes, for example in humans, include the kappa (k), lambda (l), and heavy chain genetic loci, which together comprise the myriad variable region genes, and the constant region genes mu (u), delta (d), gamma (g), sigma (e), and alpha (a) which encode the IgM, IgD, IgG, IgE, and IgA isotypes respectively. An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen. The term antibody is meant to include full length antibodies and may refer to a natural antibody from any organism, an engineered antibody, or an antibody generated recombinantly for experimental, therapeutic, or other purposes as further defined below.

Antibody fragments of interest include, but are not limited to, Fab, Fab', F(ab')2, Fv, scFv, or other antigen-binding subsequences of antibodies, either produced by the modification of whole antibodies or those synthesized de novo using recombinant DNA technologies. Antibodies may be monoclonal or polyclonal and may have other specific activities on cells (e.g., antagonists, agonists, neutralizing, inhibitory, or stimulatory antibodies). It is understood that the antibodies may have additional conservative amino acid substitutions which have substantially no effect on antigen binding or other antibody functions.

In certain embodiments, the specific binding member is a Fab fragment, a F(ab')$_2$ fragment, a scFv, a diabody or a triabody. In certain embodiments, the specific binding member is an antibody. In some cases, the specific binding member is a murine antibody or binding fragment thereof. In certain instances, the specific binding member is a recombinant antibody or binding fragment thereof. In some embodiments, the labelled specific binding member includes: a water soluble light harvesting multichromophore (e.g., as described herein) comprising a conjugated segment including: a fused 6-5-6 tricyclic co-monomer (e.g., a fluorene co-monomer, as described herein); and a fluorogenic dye covalently linked to the multichromophore in energy-receiving proximity therewith (e.g., as described herein); and a specific binding member covalently linked to the multichromophore. In some instances of the labelled specific binding member, the multichromophore is described by any one of formulae (X) and (XIX)-(XII) (e.g., as described herein), wherein: $G^1$ and $G^2$ are each independently selected from the group consisting of a terminal group (e.g., end group), a π conjugated segment, a linker and a linked specific binding member, wherein at least one of $G^1$ and $G^2$ is a linked specific binding member. In some instances, $F^1$ is a fluorene co-monomer.

Methods

As summarized above, aspects of the present disclosure include methods of evaluating a sample for the presence of a target analyte. Aspects of the subject methods include contacting the sample with a fluorogenic sensor for a target analyte to produce a sensor-contacted sample. As used herein, the terms "polymeric dye conjugate" and "fluorogenic sensor" are used interchangeably. The fluorogenic sensor can include: (i) a water soluble light harvesting multichromophore (e.g., as described herein) including a conjugated segment including: a fused 6-5-6 tricyclic co-monomer (e.g., a fluorene co-monomer, as described herein); and a fluorogenic dye covalently linked to the multichromophore in energy-receiving proximity therewith (e.g., as described herein). In certain instances, the fluorogenic sensor is a labeled specific binding member that further comprises a linked specific binding member (e.g., as described herein).

Any convenient method may be used to contact the sample with a fluorogenic sensor for a target analyte to produce the sensor-contacted sample. In some instances, the sample is contacted with the fluorogenic sensor under conditions in which the sensor specifically binds to the target analyte, if present. In some instances, the sample is contacted with the fluorogenic sensor under conditions in which the sensor chemically reacts with the target analyte, if present. Conditions in which the sensor chemically selectively reacts with the target analyte include conditions where the sensor is chemically stable and does not react in the absence of analyte. Any convenient target analyte of interest (e.g., as described herein) may be targeted in the subject methods for sensing by a subject fluorogenic sensor. In some instances, the sample is suspected of containing the target analyte of the fluorogenic sensor.

In certain instances, the method includes contacting the sample with a labeled specific binding member that includes a fluorogenic sensor for a first target analyte and a linked specific binding member that is capable of specifically binding a second target analyte. For specific binding of the specific binding member of the conjugate with the target analyte, an appropriate solution may be used that maintains the biological activity of the components of the sample and the specific binding member. The solution may be a balanced salt solution, e.g., normal saline, PBS, Hank's balanced salt solution, etc., conveniently supplemented with fetal calf serum, human platelet lysate or other factors, in conjunction with an acceptable buffer at low concentration, such as from 5-25 mM. Convenient buffers include HEPES, phosphate buffers, lactate buffers, etc. Various media are commercially available and may be used according to the nature of the target analyte, including dMEM, HBSS, dPBS, RPMI, Iscove's medium, etc., in some cases supplemented with fetal calf serum or human platelet lysate. The final components of the solution may be selected depending on the components of the sample which are included.

The temperature at which specific binding of the specific binding member of the conjugate to the second target analyte takes place may vary, and in some instances may range from 5° C. to 50° C., such as from 10° C. to 40° C., 15° C. to 40° C., 20° C. to 40° C., e.g., 20° C., 25° C., 30° C., 35° C. or 37° C. (e.g., as described above). In some instances, the temperature at which specific binding takes place is selected to be compatible with the biological activity of the specific binding member and/or the second target analyte. In certain instances, the temperature is 25° C., 30° C., 35° C. or 37° C. In certain cases, the specific binding member is an antibody or fragment thereof and the temperature at which specific binding takes place is room temperature (e.g., 25° C.), 30° C., 35° C. or 37° C. Any convenient incubation time for specific binding may be selected to allow for the formation of a desirable amount of binding complex, and in some instances, may be 1 minute (min) or more, such as 2 min or more, 10 min or more, 30 min or more, 1 hour or more, 2 hours or more, or even 6 hours or more.

Any convenient specific binding members may be utilized in the conjugate. Specific binding members of interest include, but are not limited to, those agents that specifically bind cell surface proteins of a variety of cell types, including but not limited to, stem cells, e.g., pluripotent stem cells, hematopoietic stem cells, T cells, T regulator cells, dendritic cells, B Cells, e.g., memory B cells, antigen specific B cells, granulocytes, leukemia cells, lymphoma cells, virus cells (e.g., HIV cells) NK cells, macrophages, monocytes, fibroblasts, epithelial cells, endothelial cells, and erythroid cells. Target cells of interest include cells that have a convenient cell surface marker or antigen that may be captured by a convenient specific binding member conjugate. In some embodiments, the target cell is selected from HIV containing cell, a Treg cell, an antigen-specific T-cell populations, tumor cells or hematopoetic progenitor cells (CD34+) from whole blood, bone marrow or cord blood. Any convenient cell surface proteins or cell markers may be targeted for specific binding to polymeric dye conjugates in the subject methods. In some embodiments, the target cell includes a cell surface marker selected from a cell receptor and a cell surface antigen. In some cases, the target cell may include a cell surface antigen such as CD11b, CD123, CD14, CD15, CD16, CD19, CD193, CD2, CD25, CD27, CD3, CD335, CD36, CD4, CD43, CD45RO, CD56, CD61, CD7, CD8, CD34, CD1c, CD23, CD304, CD235a, T cell receptor alpha/beta, T cell receptor gamma/delta, CD253, CD95, CD20, CD105, CD117, CD120b, Notch4, Lgr5 (N-Terminal), SSEA-3, TRA-1-60 Antigen, Disialoganglioside GD2 and CD71.

Any convenient targets may be selected for evaluation utilizing the subject methods. Targets of interest include, but are not limited to, a nucleic acid, such as an RNA, DNA, PNA, CNA, HNA, LNA or ANA molecule, a protein, such as a fusion protein, a modified protein, such as a phosphorylated, glycosylated, ubiquitinated, SUMOylated, or acetylated protein, or an antibody, a peptide, an aggregated biomolecule, a cell, a small molecule, a vitamin and a drug molecule. As used herein, the term "a target protein" refers to all members of the target family, and fragments thereof. The target protein may be any protein of interest, such as a therapeutic or diagnostic target, including but not limited to: hormones, growth factors, receptors, enzymes, cytokines, osteoinductive factors, colony stimulating factors and immunoglobulins. The term "target protein" is intended to include recombinant and synthetic molecules, which can be prepared using any convenient recombinant expression methods or using any convenient synthetic methods, or purchased commercially. In some embodiments, the polymeric dye conjugates include an antibody or antibody fragment. Any convenient target analyte that specifically binds an antibody or antibody fragment of interest may be targeted in the subject methods for specific binding to a specific binding moiety.

In some embodiments, the second target analyte is associated with a cell. In certain instances, the target analyte is a cell surface marker of the cell. In certain cases, the cell surface marker is selected from the group consisting of a cell receptor and a cell surface antigen. In some instances, the target analyte is an intracellular target, and the method further includes lysing the cell.

In some embodiments, the sample may include a heterogeneous cell population from which target cells are isolated. In some instances, the sample includes peripheral whole blood, peripheral whole blood in which erythrocytes have been lysed prior to cell isolation, cord blood, bone marrow, density gradient-purified peripheral blood mononuclear cells or homogenized tissue. In some cases, the sample includes hematopoetic progenitor cells (e.g., CD34+ cells) in whole blood, bone marrow or cord blood. In certain embodiments, the sample includes tumor cells in peripheral blood. In certain instances, the sample is a sample including (or suspected of including) viral cells (e.g., HIV).

The labelled specific binding members find use in the subject methods, e.g., for labeling a target cell, particle, target or analyte with a polymeric dye or fluorogenic sensor. For example, labelled specific binding members find use in labeling cells to be processed (e.g., detected, analyzed, and/or sorted) in a flow cytometer. The labelled specific binding members may include antibodies that specifically bind to, e.g., cell surface proteins of a variety of cell types (e.g., as described herein). The labelled specific binding members may be used to investigate a variety of biological (e.g., cellular) properties or processes such as cell cycle, cell proliferation, cell differentiation, DNA repair, T cell signaling, apoptosis, cell surface protein expression and/or presentation, and so forth. Labelled specific binding members may be used in any application that includes (or may include) antibody-mediated labeling of a cell, particle or analyte.

In some instances of the method, the labelled specific binding member includes a multichromophore according to any one of formulae (X) and (XIX)-(XII) (e.g., as described herein), wherein: $G^1$ and $G^2$ are each independently selected from the group consisting of a terminal group, a π conjugated segment, a linker and a linked specific binding member, wherein at least one of $G^1$ and $G^2$ is a linked specific binding member.

Aspects of the subject methods include evaluating the sensor-contacted sample for fluorescence emission from the fluorogenic sensor to evaluate whether the target analyte is present in the sample. Once the sample has been contacted with the fluorogenic sensor, any convenient methods may be utilized in assaying the sensor-contacted sample that is produced for a ratiometric change in fluorescence. Evaluating the sensor-contacted sample can include detecting a fluorescent signal from the sample, if present, and comparing the signal to a control solution of sensor that contains no sample. Any convenient ratiometric methods that find use in detecting and quantitating fluorescence emissions from fluorogenic dyes can be utilized in the subject methods, such as those ratiometric methods described by, US Publication No. 20050090014.

In certain cases, the subject methods include evaluating the sensor-contacted sample over a period of time. The evaluating may be performed continuously or at discrete time points to produce a temporal evaluation of the sample over any convenient time frame. In some cases, the evaluating is performed over a period of 1 minute or more, such as 10 minutes or more, 30 minutes or more, 60 minutes or more, 3 hours or more, 6 hours or more, 12 hours or more, 24 hours or more, 1 week or more, 1 month or more, or even more. In some instances, the subject methods include evaluating a spatial distribution of fluorescence emissions from a sensor-contacted sample. Any convenient methods of evaluating a sample for spatial distribution of fluorescence emissions can be utilized, including but not limited to fluorescence microscopy methods.

In some cases, a sensor that is a labeled specific binding member can be used to specifically bind the sensor to a desired target location in a sample. In certain instances, in the sensor-contacted sample, the labeled specific binding member is localized at a target location via specific binding of the specific binding member to a second target analyte. The presence of a first target analyte that is sensed by the linked fluorogenic sensor can then be evaluated, e.g., spatially and/or temporally evaluated, e.g., using fluorescence microscopy.

In some cases, the assaying includes a separating step where the target analyte, if present, is separated from the sample. A variety of methods can be utilized to separate a target analyte from a sample, e.g., via immobilization on a support. Assay methods of interest include, but are not limited to, any convenient methods and assay formats where pairs of specific binding members such as avidin-biotin or hapten-anti-hapten antibodies find use, are of interest. Methods and assay formats of interest that may be adapted for use with the subject compositions include, but are not limited to, flow cytometry methods, in-situ hybridization methods, enzyme-linked immunosorbent assays (ELISAs), western blot analysis, magnetic cell separation assays and fluorochrome purification chromatography.

In certain embodiments, the method further includes contacting the sample with a second specific binding member that specifically binds an analyte of interest. In certain instances, the second specific binding member is support bound. Any convenient supports may be utilized to immobilize a component of the subject methods (e.g., a second specific binding member). In certain instances, the support is a particle, such as a magnetic particle. In some instances, the second specific binding member and the labeled specific binding member produce a sandwich complex that may be isolated and detected, if present, using any convenient methods. In some embodiments, the method further includes flow cytometrically analyzing the sample for a fluorescent emission from the sensor. Assaying for the presence of a fluorescent emission from the sensor may provide assay results (e.g., qualitative or quantitative assay data) which can be used to evaluate whether the target analyte is present in the sample.

Any convenient supports may be utilized in the subject methods to immobilize any convenient component of the methods, e.g., sensor, labelled specific binding member, first or second target analytes, secondary specific binding member, etc. Supports of interest include, but are not limited to: solid substrates, where the substrate can have a variety of configurations, e.g., a sheet, bead, or other structure, such as a plate with wells; beads, polymers, particle, a fibrous mesh, hydrogels, porous matrix, a pin, a microarray surface, a chromatography support, and the like. In some instances, the support is selected from the group consisting of a particle, a planar solid substrate, a fibrous mesh, a hydrogel, a porous matrix, a pin, a microarray surface and a chromatography support. The support may be incorporated into a system that it provides for cell isolation assisted by any convenient methods, such as a manually-operated syringe, a centrifuge or an automated liquid handling system. In some cases, the support finds use in an automated liquid handling system for the high throughput isolation of cells, such as a flow cytometer.

In some embodiments of the method, the separating step includes applying an external magnetic field to immobilize a magnetic particle. Any convenient magnet may be used as a source of the external magnetic field (e.g., magnetic field gradient). In some cases, the external magnetic field is generated by a magnetic source, e.g. by a permanent magnet or electromagnet. In some cases, immobilizing the magnetic particles means the magnetic particles accumulate near the surface closest to the magnetic field gradient source, i.e. the magnet.

The separating may further include one or more optional washing steps to remove unbound material of the sample from the support. Any convenient washing methods may be used, e.g., washing the immobilized support with a biocompatible buffer which preserves the specific binding interaction of the polymeric dye and the specific binding member. Separation and optional washing of unbound material of the sample from the support provides for an enriched population of target cells where undesired cells and material may be removed.

In certain embodiments, the method further includes detecting fluorescence from the sensor. Detecting may include exciting the multichromophore with one or more lasers and subsequently detecting fluorescence emission from the product of the fluorogenic sensor using one or more optical detectors. Detection of the fluorescence can be performed using any convenient instruments and methods, including but not limited to, flow cytometry, FACS systems, fluorescence microscopy; fluorescence, luminescence, ultraviolet, and/or visible light detection using a plate reader; high performance liquid chromatography (HPLC); and mass spectrometry. When using fluorescently labeled components in the methods and compositions of the present disclosure, it is recognized that different types of fluorescence detection systems can be used to practice the subject methods. In some cases, high throughput screening can be performed, e.g., systems that use 96 well or greater microtiter plates. A variety of methods of performing assays on fluorescent materials can be utilized, such as those methods described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361.

Fluorescence in a sample can be measured using a fluorimeter. In some cases, excitation radiation, from an excitation source having a first wavelength, passes through excitation optics. The excitation optics cause the excitation radiation to excite the sample. In response, fluorescent dye products of the sensor in the sample emit radiation which has a wavelength that is different from the excitation wavelength. Collection optics then collect the emission from the sample. The device can include a temperature controller to maintain the sample at a specific temperature while it is being scanned. In certain instances, a multi-axis translation stage moves a microtiter plate holding a plurality of samples in order to position different wells to be exposed. The multi-axis translation stage, temperature controller, autofocusing feature, and electronics associated with imaging and data collection can be managed by an appropriately programmed digital computer. The computer also can transform the data collected during the assay into another format for presentation.

In some embodiments, the method of evaluating a sample for the presence of a target analyte further includes detecting fluorescence in a flow cytometer. In some embodiments, the method of evaluating a sample for the presence of a target analyte further includes imaging the sensor-contacted sample using fluorescence microscopy. Fluorescence microscopy imaging can be used to identify the presence and/or location of a target analyte in the contacted sample to evaluate whether the target analyte is present and whether the analyte changes over time. Microscopy methods of interest that find use in the subject methods include laser scanning confocal microscopy.

Also provided are methods of labelled a target molecule. The subject fluorogenic sensors, find use in a variety of methods of labelling, separation, detection and/or analysis. In some embodiments, the method includes: contacting the target molecule with a fluorogenic sensor to produce a labelled target molecule, wherein the polymeric dye includes: a water soluble light harvesting multichromophore comprising a conjugated segment comprising: a fluorene co-monomer; and a fluorogenic dye covalently linked to the multichromophore in energy-receiving proximity therewith; and a conjugation tag that covalently links to the target molecule. In some instances of the method, the labelled specific binding member includes a multichromophore according to any one of formulae (X) and (XIX)-(XII) (e.g., as described herein), where one of $G^1$ and $G^2$ is a terminal group and the other of $G^1$ and $G^2$ is the conjugation tag. In some instances, $F^1$ is a fluorene co-monomer.

As used herein the term "conjugation tag" refers to a group that includes a chemoselective functional group (e.g., as described herein) that can covalently link with a compatible functional group of a target molecule, after optional activation and/or deprotection. Any convenient conjugation tags may be utilized in the subject polymeric dyes in order to conjugate the dye to a target molecule of interest. In some embodiments, the conjugation tag includes a terminal functional group selected from an amino, a carboxylic acid or a derivative thereof, a thiol, a hydroxyl, a hydrazine, a hydrazide, a azide, an alkyne and a protein reactive group (e.g. amino-reactive, thiol-reactive, hydroxyl-reactive, imidazolyl-reactive or guanidinyl-reactive).

Any convenient methods and reagent may be adapted for use in the subject labelling methods in order to covalently link the conjugation tag to the target molecule. Methods of interest for labelling a target, include but are not limited to, those methods and reagents described by Hermanson, Bioconjugate Techniques, Third edition, Academic Press, 2013. The contacting step may be performed in an aqueous solution. In some instances, the conjugation tag includes an amino functional group and the target molecule includes an activated ester functional group, such as a NHS ester or sulfo-NHS ester, or vice versa. In certain instances, the conjugation tag includes a maleimide functional group and the target molecule includes a thiol functional group, or vice versa.

Any convenient target molecules may be selected for labelling utilizing the subject methods. Target molecules of interest include, but are not limited to, a nucleic acid, such as an RNA, DNA, PNA, CNA, HNA, LNA or ANA molecule, a protein, such as a fusion protein, a modified protein, such as a phosphorylated, glycosylated, ubiquitinated, SUMOylated, or acetylated protein, or an antibody, a peptide, an aggregated biomolecule, a cell, a small molecule, a vitamin and a drug molecule. As used herein, the term "a target protein" refers to all members of the target family, and fragments thereof. The target protein may be any protein of interest, such as a therapeutic or diagnostic target, including but not limited to: hormones, growth factors, receptors, enzymes, cytokines, osteoinductive factors, colony stimulating factors and immunoglobulins. The term "target protein" is intended to include recombinant and synthetic molecules, which can be prepared using any convenient recombinant expression methods or using any convenient synthetic methods, or purchased commercially. In some embodiments, the target molecule is a specific binding member (e.g., as described herein). In certain instances, the specific binding member is an antibody. In some instances, the specific binding member is an antibody fragment or binding derivative thereof. In some case, the antibody fragment or binding derivative thereof is selected from the group consisting of a Fab fragment, a F(ab')$_2$ fragment, a scFv, a diabody and a triabody.

In some cases, the method includes a separating step where the labelled target molecule is separated from the reaction mixture, e.g., excess reagents or unlabeled target. A variety of methods may be utilized to separate a target from a sample, e.g., via immobilization on a support, precipitation, chromatography, and the like. In some instances, the method further includes detecting and/or analyzing the labelled target molecule. In some instances, the method further includes fluorescently detecting the labelled target molecule. Any convenient methods may be utilized to detect and/or analyze the labelled target molecule in conjunction with the subject methods and compositions. Methods of analyzing a target of interest that find use in the subject methods, include but are not limited to, flow cytometry, fluorescence microscopy, in-situ hybridization, enzyme-linked immunosorbent assays (ELISAs), western blot analysis, magnetic cell separation assays and fluorochrome purification chromatography. Detection methods of interest include but are not limited to fluorescence spectroscopy, fluorescence microscopy, nucleic acid sequencing, fluorescence in-situ hybridization (FISH), protein mass spectroscopy, flow cytometry, and the like.

Detection may be achieved directly via the fluorogenic sensor, or indirectly by a secondary detection system. The latter may be based on any one or a combination of several different principles including, but not limited to, antibody labelled anti-species antibody and other forms of immunological or non-immunological bridging and signal amplification systems (e.g., biotin-streptavidin technology, protein-A and protein-G mediated technology, or nucleic acid probe/anti-nucleic acid probes, and the like). Suitable reporter molecules may be those known in the field of immunocytochemistry, molecular biology, light, fluorescence, and electron microscopy, cell immunophenotyping, cell sorting, flow cytometry, cell visualization, detection, enumeration, and/or signal output quantification. More than one antibody of specific and/or non-specific nature might be labelled and used simultaneously or sequentially to enhance target detection, identification, and/or analysis.

Systems and Devices

Aspects of the invention further include systems for use in practicing the subject methods and compositions. A sample analysis system can include sample field of view or a flow channel loaded with a sample and a fluorogenic sensor or a labelled specific binding member. In some embodiments, the system is a flow cytometric system including: a flow cytometer including a flow path; a composition in the flow path, wherein the composition includes: a sample; and a fluorogenic sensor (e.g., as described herein) or a labelled specific binding member (e.g., as described herein).

In some embodiments, the system for analyzing a sample is a fluorescence microscopy system, including: a fluorescence microscope comprising a sample field of view; and a composition disposed in the sample field of view, wherein the composition comprises a sample; and fluorogenic sensor (e.g., as described herein) a labelled specific binding member (e.g., as described herein). In some instances of the systems, the labelled specific binding member includes: a water soluble light harvesting multichromophore (e.g., as described herein) comprising a conjugated segment including: a fused 6-5-6 tricyclic co-monomer (e.g., a fluorene co-monomer, as described herein); and a fluorogenic dye covalently linked to the multichromophore in energy-receiving proximity therewith (e.g., as described herein). In certain cases, the fluorogenic sensor further includes a specific binding member covalently linked to the multichromophore. In some instances of the subject systems, the fluorogenic sensor or labelled specific binding member includes the multichromophore that is described by any one of formulae (X) and (XIX)-(XII) (e.g., as described herein), wherein: $G^1$ and $G^2$ are each independently selected from the group consisting of a terminal group, a π conjugated segment, a linker and a linked specific binding member. In some cases, at least one of $G^1$ and $G^2$ is a linked specific binding member. In some instances, $F^1$ is a fluorene co-monomer.

In certain embodiments of the systems, the composition further includes a second specific binding member that is support bound and specifically binds the target analyte. In some cases, the support includes a magnetic particle. As such, in certain instances, the system may also include a controllable external paramagnetic field configured for application to an assay region of the flow channel.

The sample may include a cell. In some instances, the sample is a cell-containing biological sample. In some instances, the sample includes a labelled specific binding member specifically bound to a target cell. In certain instances, the target analyte that is specifically bound by the specific binding member is a cell surface marker of the cell. In certain cases, the cell surface marker is selected from the group consisting of a cell receptor and a cell surface antigen.

In certain aspects, the system may also include a light source configured to direct light to an assay region of the flow channel or sample field of view. The system may include a detector configured to receive a signal from an assay region of the flow channel or a sample field of view, wherein the signal is provided by the fluorescent composition. Optionally further, the sample analysis system may include one or more additional detectors and/or light sources for the detection of one or more additional signals.

In certain aspects, the system may further include computer-based systems configured to detect the presence of the fluorescent signal. A "computer-based system" refers to the hardware means, software means, and data storage means used to analyze the information of the present invention. The minimum hardware of the computer-based systems of the present invention includes a central processing unit (CPU), input means, output means, and data storage means. A skilled artisan can readily appreciate that any one of the currently available computer-based system are suitable for use in the subject systems. The data storage means may include any manufacture including a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g., word processing text file, database format, etc.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

In addition to the sensor device and signal processing module, e.g., as described above, systems of the invention may include a number of additional components, such as data output devices, e.g., monitors and/or speakers, data input devices, e.g., interface ports, keyboards, etc., fluid handling components, power sources, etc.

In certain aspects, the system includes a flow cytometer. Flow cytometers of interest include, but are not limited to, those devices described in U.S. Pat. Nos. 4,704,891; 4,727,029; 4,745,285; 4,867,908; 5,342,790; 5,620,842; 5,627,037; 5,701,012; 5,895,922; and 6,287,791; the disclosures of which are herein incorporated by reference.

Aspects of the present disclosure include devices for monitoring a target analyte in a subject. The subject devices can include a fluorogenic sensor for the target analyte (e.g., as described herein); and a means for fluorescently detecting the fluorescent dye product of the sensor that is configured for excitation by the multichromophore. Any convenient light source, such as a laser, a UV light source, with an optional filter for an excitation wavelength of interest can be utilized to excite the fluorogenic sensor. Any convenient detector, fluorimeter, microscope, optical electronic sensor, collimated laser diode, miniature spectrometer can be utilized to collect a fluorescence emission in the subject device, e.g., at a single wavelength. The device can also include means for obtaining a biological sample (e.g., a blood sample) from the subject. A blood sample may be obtained from the subject via a syringe, a needle, a cutting or incising blade, via a dialysis chamber or the like. In some instances, the device includes a glucose sensor. Glucose sensing devices and components thereof which can be adapted for use in the subject devices include, but are not limited to those described by Pickup, J. C., et al., "Fluorescence-based glucose sensors." Biosens Bioelectron, 2005. 20(12): p. 2555-65; and Ballerstadt et al., "Fiber-Coupled Fluorescence Affinity Sensor for 3-Day in Vivo Glucose Sensing", Diabetes Sci Technol. 2007 May; 1(3): 384-393.

In certain embodiments, the device is an optical system for determining blood glucose concentration, and comprises: an excitation light source that emits an excitation light signal; a fiber optic sensor sized to be positioned within a blood vessel, the sensor being operably coupled to the excitation light source and comprising an indicator system comprising a fluorogenic sensor (e.g., as described herein), wherein upon absorption of at least a portion of the excitation light signal, the indicator system emits an emission light signal having an intensity related to the blood glucose concentration; at least one optical module configured to deliver the excitation light signal to the fiber optic sensor and the emission light signal from the fiber optic sensor to a detector system, wherein the detector system comprises a means for detecting the emission light signal and at least a second light signal, wherein the second light signal is derived from the excitation light source or an optional reference light source; and a computer system configured to receive data from the detector system, wherein the computer system is configured to perform ratiometric calculations on the data to substantially eliminate optical artifacts unrelated to glucose concentrations, wherein the computer system comprises a monitor for outputting data to a user, an input device for allowing the user to input additional data into the computer system, a processor for performing the ratiometric calculations, a storage device for storing data, and a memory.

Other systems and devices may find use in practicing the subject methods. In certain aspects, the system may be a fluorimeter or microscope loaded with a sample having a fluorescent composition of any of the embodiments discussed herein. The fluorimeter or microscope may include a light source configured to direct light to the assay region of the flow channel or sample field of view. The fluorimeter or microscope may also include a detector configured to receive a signal from an assay region of the flow channel or field of view, wherein the signal is provided by the fluorescent composition.

Kits

Aspects of the invention further include kits for use in practicing the subject methods and compositions. The compositions of the invention can be included as reagents in kits either as starting materials or provided for use in, for example, the methodologies described above.

A kit can include a fluorogenic sensor (e.g., as described herein) including a water soluble light harvesting multichromophore including a conjugated segment including: a fused 6-5-6 tricyclic co-monomer; and a fluorogenic dye covalently linked to the multichromophore in energy-receiving proximity therewith (e.g., as described herein); and one or more components selected from the group consisting of a polymeric dye, a fluorophore, a specific binding member, a specific binding member conjugate, a support bound specific binding member, a cell, a support, a biocompatible aqueous elution buffer, and instructions for use. In some embodiments of the kit, the multichromophore is covalently linked to a specific binding member. In some instances, the specific binding member is an antibody. In certain instances, the specific binding member is an antibody fragment or binding derivative thereof. In certain cases, the antibody fragment or binding derivative thereof is selected from the group consisting of a Fab fragment, a F(ab')2 fragment, a scFv, a diabody and a triabody.

In certain embodiments, the kit finds use in evaluating a sample for the presence of a target analyte, such as an intracellular target. As such, in some instances, the kit includes one or more components suitable for lysing cells. The one or more additional components of the kit may be provided in separate containers (e.g., separate tubes, bottles, or wells in a multi-well strip or plate).

In certain aspects, the kit further includes reagents for performing a flow cytometric assay. Reagents of interest include, but are not limited to, buffers for reconstitution and dilution, buffers for contacting a cell sample the multichromophore, wash buffers, control cells, control beads, fluorescent beads for flow cytometer calibration and combinations thereof. The kit may also include one or more cell fixing reagents such as paraformaldehyde, glutaraldehyde, methanol, acetone, formalin, or any combinations or buffers thereof. Further, the kit may include a cell permeabilizing reagent, such as methanol, acetone or a detergent (e.g., triton, NP-40, saponin, tween 20, digitonin, leucoperm, or any combinations or buffers thereof. Other protein transport inhibitors, cell fixing reagents and cell permeabilizing reagents familiar to the skilled artisan are within the scope of the subject kits.

The compositions of the kit may be provided in a liquid composition, such as any suitable buffer. Alternatively, the compositions of the kit may be provided in a dry composition (e.g., may be lyophilized), and the kit may optionally include one or more buffers for reconstituting the dry composition. In certain aspects, the kit may include aliquots of the compositions provided in separate containers (e.g., separate tubes, bottles, or wells in a multi-well strip or plate).

In addition, one or more components may be combined into a single container, e.g., a glass or plastic vial, tube or bottle. In certain instances, the kit may further include a container (e.g., such as a box, a bag, an insulated container, a bottle, tube, etc.) in which all of the components (and their separate containers) are present. The kit may further include packaging that is separate from or attached to the kit container and upon which is printed information about the kit, the components of the and/or instructions for use of the kit.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, portable flash drive, etc., on which the information has been recorded. Yet another means that may be present is a website address which may be used via the Internet to access the information at a removed site. Any convenient means may be present in the kits.

Utility

The fluorogenic sensors, compositions, methods and systems as described herein may find use in a variety of applications, including diagnostic and research applications, in which the labeling, detection and/or analysis of a target analyte of interest is desirable. Such applications include methodologies such as cytometry, microscopy, immunoassays (e.g. competitive or non-competitive), assessment of a free analyte, assessment of receptor bound ligand, and so forth. In some instances, the subject sensors find use in evaluating the spatial and temporal distribution of a target analyte of interest in a sample. Such applications include research applications involving the elucidation of biological processes, e.g., in a cellular sample, where the action of a target analyte is implicated.

The compositions, system and methods described herein may be useful in analysis of any of a number of samples, including but not limited to, biological fluids, cell culture samples, and tissue samples. In certain aspects, the compositions, system and methods described herein may find use in methods where analytes are detected in a sample, if present, using fluorescent labels, such as in fluorescent activated cell sorting or analysis, immunoassays, immunostaining, and the like. In certain instances, the compositions, methods and systems find use in applications where the evaluation of a sample for the presence of a target analyte is of interest. In certain cases, the sample is in vivo, and the fluorogenic sensors find use in a device that monitors a biologically relevant analyte, such as glucose in a subject.

In some cases, the methods and compositions find use in any assay format where the detection and/or analysis of a target from a sample is of interest, including but not limited to, flow cytometry, fluorescence microscopy, in-situ hybridization, enzyme-linked immunosorbent assays (ELISAs), western blot analysis, magnetic cell separation assays and fluorochrome purification chromatography. In certain instances, the methods and compositions find use in any application where the fluorescent labelling of a target molecule is of interest. The subject compositions may be adapted for use in any convenient applications where pairs of specific binding members find use, such as biotin-streptavidin and hapten-anti-hapten antibody.

EXAMPLES

Example 1: Synthesis of Fluorogenic Sensor MC-FL

A fluorogenic sensor (MC-FL) that features a fluorescein lactone fluorogenic dye conjugated to a multichromophore (MC) core polymer (FIG. 2) is prepared.

Materials:

Multichromophore including fluorene linking co-monomer having sidechain amino functional groups (—$NH_2$) (MC core):

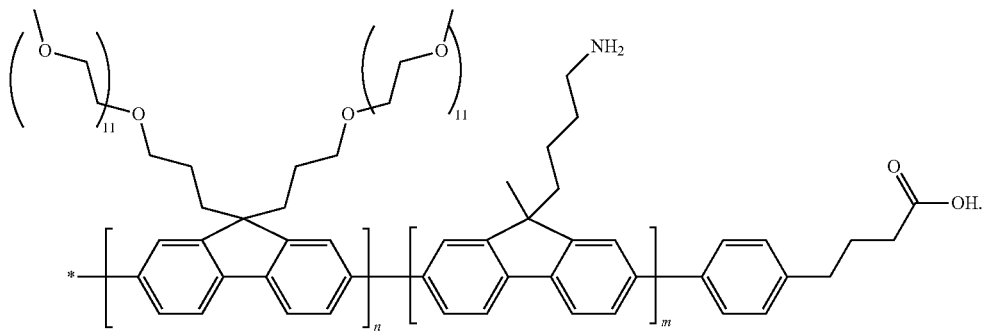

Lactone fluorescein-5(6)-carboxamidocaproic acid N-succinimidyl ester (FL-NHS)
Procedure:
1. Make an 80 mg·mL$^{-1}$ stock solution of MC core in 20% (v/v) EtOH in DMSO. By dissolving 25.9 mg of MC CORE in 323 µL of the EtOH/DMSO solution. Assuming a MW of 60 kDa for MC CORE, 25.9 mg is 0.43 µmols. 80 mg/mL MC CORE=1.33 mM
2. Dissolve 4.9 umols of lactone fluorescein-5(6)-carboxamidocaproic acid N-succinimidyl ester (FL-NHS) in 500 µL of DMSO to make a 9.8 mM solution.
3. In a 1.5 mL Eppendorf tube, place:
   a. 37.7 µL of 1.33 mM MC CORE
   b. 862 µL of PBS, pH=8
   c. FL-NHS, added in 4 equal portions with mixing in between each portion.
4. Mix the solution, which contained ca. 50 µM MC CORE and FL-NHS, in the dark at RT using a rotating Eppendorf tube rack.
5. After 4 hours, remove unreacted FL-NHS using a Zeba spin column with a 7 kDa MW cut-off, according to manufacturer's specifications.

Example 2: Properties of Fluorogenic Sensor MC-FL

Figure 2:
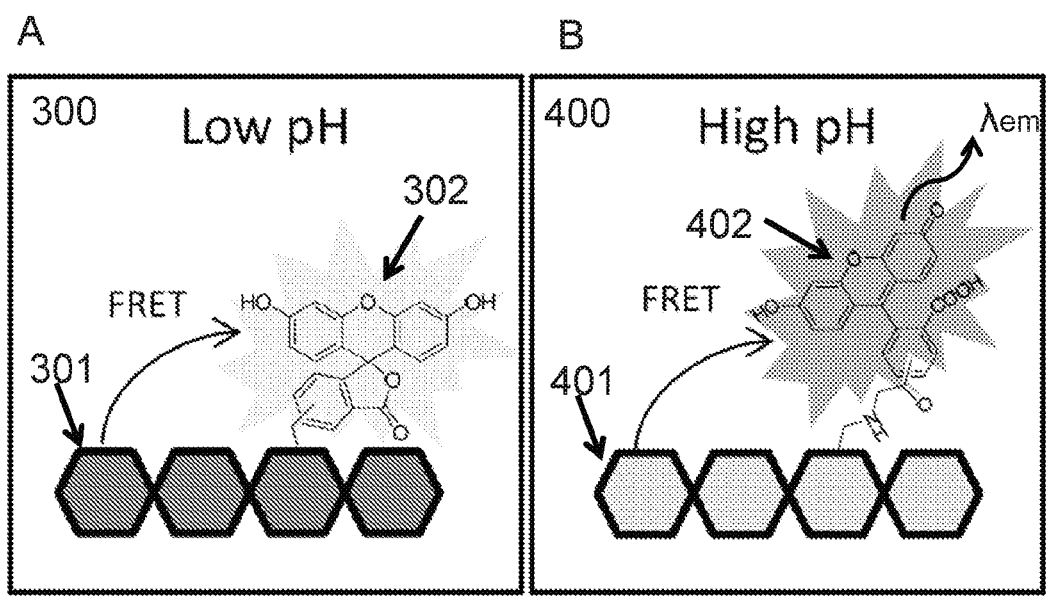
FIG. 2 illustrates a schematic of an exemplary fluorogenic sensor (e.g., MC-FL) that is sensitive to pH. Excitation of the fluorescent water soluble light harvesting multichromophore (301) results in fluorescence resonance energy transfer (FRET) to the linked fluorogenic dye (302) including a lactone form of fluorescein (e.g., in an "off state"). In the presence of a target analyte (e.g., hydroxide ions) the lactone of the fluorogenic dye is hydrolyzed to produce a more fluorescent fluorescein dye (402) with increased fluorescent emission ($\lambda_{em}$) following FRET from the donor multichromophore (401). The change in fluorescence intensity is ratiometric providing for quantification of the analyte concentration.

FIG. 2 illustrates a schematic of the fluorogenic sensor MC-FL that is sensitive to pH. Excitation of the fluorescent water soluble light harvesting multichromophore (301) results in fluorescence resonance energy transfer (FRET) to the linked fluorogenic dye (302) including a non-fluorescent lactone form of fluorescein. In the presence of hydroxide ions (i.e., increasing pH) the lactone of the fluorogenic dye is hydrolyzed to produce the more fluorescent fluorescein form of the dye (402) with increased fluorescent emission ($\lambda_{em}$) following FRET from the donor multichromophore (401). The change in fluorescence intensity is ratiometric providing for measurement of the pH in a sample containing the sensor.

Figure 3:
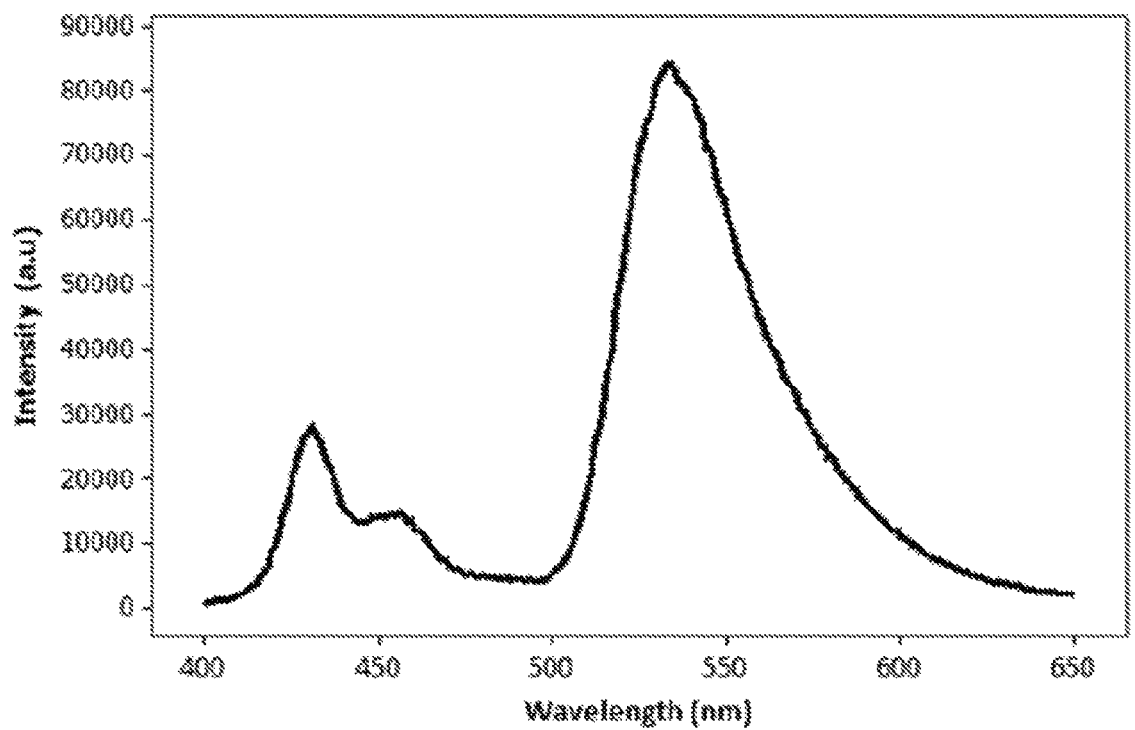
FIG. 3 shows a fluorescence emission spectrum ($\lambda_{ex}$=390 nm) of a 31 nM solution of the exemplary fluorogenic sensor MC-FL in PBS buffer.
Figure 4:
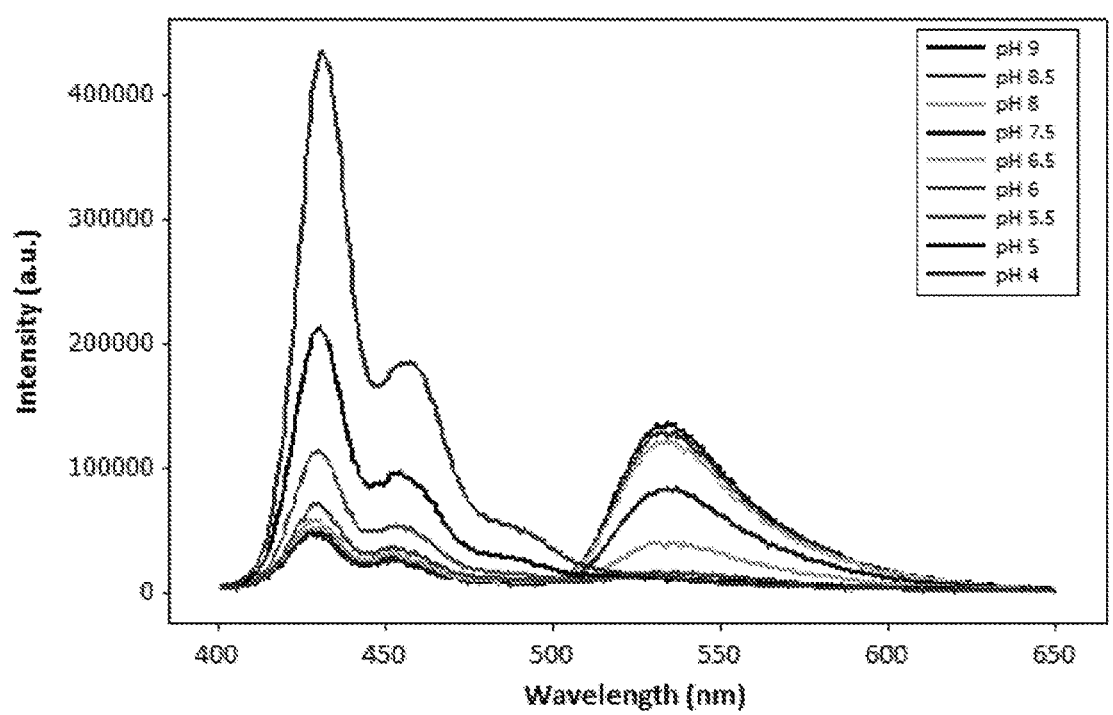
FIG. 4 shows fluorescence emission spectrum ($\lambda_{ex}$=390 nm) of the exemplary fluorogenic sensor MC-FL in 25 mM citrate buffer solutions at various pH values.

To characterize the photophysical properties of MC-FL, the absorbance and emission spectra (FIG. 3) of the sensor were obtained. FIG. 3 shows a fluorescence emission spectrum ($\lambda_{ex}$=390 nm) of a 31 nM solution of MC-FL in PBS buffer. The emission spectra of MC-FL in buffered solutions at a variety of pH values were obtained (FIG. 4). FIG. 4 shows fluorescence emission spectrum ($\lambda_{ex}$=390 nm) of the fluorogenic sensor MC-FL in 25 mM citrate buffer solutions at various pH values.

Figure 5:
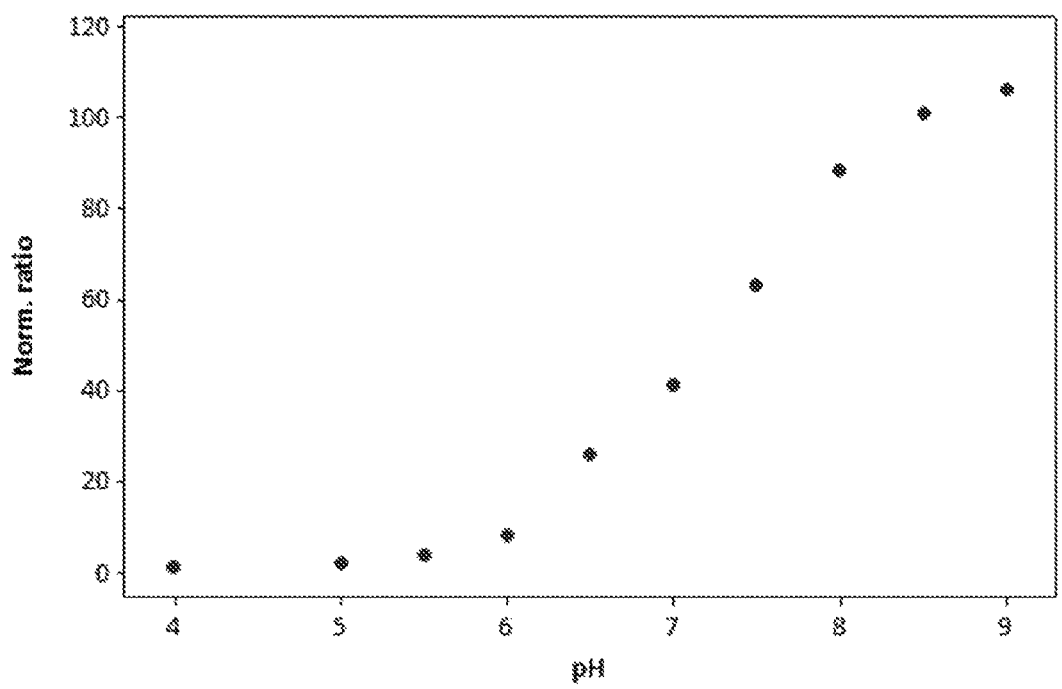
FIG. 5 shows a plot of the change in normalized fluorescence ratio (Norm. ratio=Intensity$_{(530nm)}$/Intensity$_{(430nm)}$) of the exemplary fluorogenic sensor MC-FL in 25 mM citrate buffer solutions as a function of pH.

The fluorescence spectrum of MC-FL in PBS (FIG. 3) shows two small emission bands at 430 and 453 nm, which are associated with the MC polymer, and a larger emission band at 530 nm, which is assigned to the fluorescein dye moiety. When the pH of the solution is changed from 4 to 9, a ratiometric change is observed in the emission spectra (FIG. 4). At low pH values, the emission spectrum of MC-FL is dominated by the MC polymer and almost no emission is observed from the fluorescein dye moiety (FIG. 4, pH 4 line). In contrast, at pH 9, the signal from the MC polymer decreases dramatically with concomitant increase in the fluorescein dye moiety emission ($\lambda$em=530 nm; FIG. 4, pH 9 line). When the ratio (R) defined as R=$I_{530}/I_{430}$ (with arbitrarily $R_{pH}4$=1 normalization), is plotted as a function of pH, a sigmoidal curve is obtained with the inflection point of ~7.3 (FIG. 5). FIG. 5 shows a plot of the change in normalized fluorescence ratio (Norm. ratio=Intensity$_{(530nm)}$/Intensity$_{(430nm)}$) of the exemplary fluorogenic sensor MC-FL in 25 mM citrate buffer solutions as a function of pH.

At lower pH values, the fluorescein dye moiety adopts a non-fluorescent lactone configuration. Because this "off-state" form of the fluorescein moiety is non-fluorescent, any energy transfer from the MC polymeric multichromophore is fails to result in fluorescence from the fluorescein moiety. The resulting emission spectrum for the sensor is thus dominated by the MC conjugated polymer. As the pH value increases, the lactone ring opens and FRET (energy transfer to the fluorescent fluorescein moiety) with concomitant fluorescence emission is established.

Notwithstanding the appended clauses, the disclosure set forth herein is also defined by the following clauses:
1. A fluorogenic sensor for a target analyte, the sensor comprising a water soluble light harvesting multichromophore and a linked fluorogenic dye in energy-receiving proximity therewith, wherein the sensor is described by formula (X):

(X)

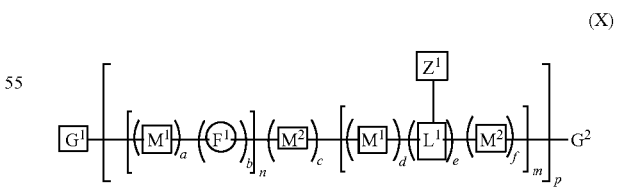

wherein:
$Z^1$ is the linked fluorogenic dye in energy receiving proximity to the multichromophore;
$F^1$ is a fluorene co-monomer;
each $M^1$ and each $M^2$ is independently a co-monomer;
$L^1$ is a fluorene co-monomer substituted with the linked fluorogenic dye ($Z^1$);

e is 1;

a, b, c, d and f are each independently 0 or 1, wherein a+b+c+d+f≥1;

n is 0 or an integer from 1 to 10,000;

m is an integer from 1 to 10,000;

p is an integer from 1 to 100,000; and $G^1$ and $G^2$ are each independently selected from a terminal group, a π conjugated segment, a linker and a linked specific binding member;

wherein the fluorogenic dye is configured to sense the target analyte to produce a fluorescent dye configured for excitation by the multichromophore.

2. The fluorogenic sensor according to Clause 1, wherein the linked fluorogenic dye is non-fluorescent in the absence of target analyte when the sensor is irradiated with incident excitation light at the absorption maxima wavelength of the multichromophore.

3. The fluorogenic sensor according to Clause 1, wherein the linked fluorogenic dye quenches 10% or more of the fluorescence of the multichromophore.

4. The fluorogenic sensor according to Clause 1, wherein the fluorescence ratio of the fluorescent versus non-fluorescent forms of the sensor is 10 or more.

5. The fluorogenic sensor according to any of Clauses 1 to 4, wherein the linked fluorogenic dye is chemically reactive with the target analyte.

6. The fluorogenic sensor according to any of Clauses 1 to 4, wherein the linked fluorogenic dye specifically binds the target analyte.

7. The fluorogenic sensor according to any of Clauses 1 to 4, wherein the linked fluorogenic dye is a fluorogenic protein.

8. The fluorogenic sensor according to any of Clauses 1 to 5, wherein the linked fluorogenic dye comprises a lactone or spiro-lactone group that is configured to chemically react with the target analyte via ring-opening reaction to produce the fluorescent dye.

9. The fluorogenic sensor according to any of Clauses 1 to 5, wherein the target analyte is nitric oxide and the linked fluorogenic dye comprises a vicinal diamine that is configured to undergo oxidative cycloaddition with the nitric oxide.

10. The fluorogenic sensor according to any of Clauses 1 to 5, wherein the target analyte is glucose and the linked fluorogenic dye is a boronic acid-containing dye.

11. The fluorogenic sensor according to any of Clauses 1 to 5, wherein the target analyte is hydrogen peroxide and the linked fluorogenic dye comprises a boronic acid or boronic ester fluorescence-masking group.

12. The fluorogenic sensor according to any of Clauses 1 to 11, wherein the target analyte is selected from hydroxide, nitric oxide, a metal ion, glucose, lactate, hydrogen peroxide, oxygen and a reactive oxygen species.

13. The fluorogenic sensor according to any of Clauses 1 to 12, wherein the fluorescent dye emission has a quantum yield of 0.1 or more.

14. The fluorogenic sensor according to any of Clauses 1 to 13, wherein the fluorescent dye product emission has a brightness of 100 $mM^{-1}$ $cm^{-1}$ or more.

15. The fluorogenic sensor according to any of Clauses 1 to 14, wherein the fluorene co-monomer is substituted with at least one non-ionic side group capable of imparting solubility in water in excess of 10 mg/m L.

16. The fluorogenic sensor according to Clause 15, wherein the at least one non-ionic side group is selected from $(CH_2)_x(OCH_2CH_2)_yOCH_3$, wherein each x is independently an integer from 0-20 and each y is independently an integer from 0 to 50, and a benzyl substituted with at least one $(OCH_2CH_2)_zOCH_3$ group wherein each z is independently an integer from 0 to 50.

17. The fluorogenic sensor according to any of Clauses 1 to 16, wherein:

b is 1;

a+c≥1;

d+f≥1; and n is an integer from 1 to 10,000.

18. The fluorogenic sensor according to any of Clauses 1 to 17, described by formula (II):

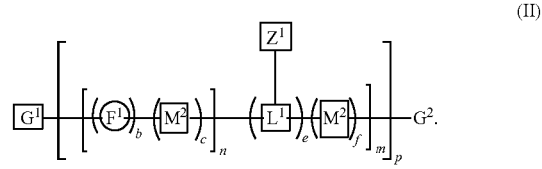

(II)

19. The fluorogenic sensor according to Clause 18, wherein:

b is 1;

c is 0 or 1;

e and f are each 1;

$G^1$ is a terminal group; and $G^2$ is a terminal group, a linker or a linked specific binding member.

20. The fluorogenic sensor according to any of Clauses 18 to 19, wherein c is 1.

21. The fluorogenic sensor according to any of Clauses 1 to 17, described by formula (III):

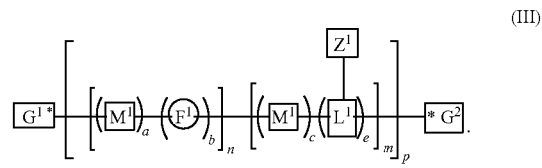

(III)

22. The fluorogenic sensor according to any of Clauses 1 to 21, wherein:

$G^1$ is a terminal group; and $G^2$ is a terminal group, a linker or a linked specific binding member.

23. The fluorogenic sensor according to any of Clauses 21 to 22, wherein a+c=1.

24. The fluorogenic sensor according to any of Clauses 1 to 23, wherein the $M^1$ and $M^2$ co-monomers are independently an optionally substituted aryl or heteroaryl co-monomer.

25. The fluorogenic sensor according to Clause 24, wherein the $M^1$ and $M^2$ co-monomers are independently a substituted or unsubstituted co-monomer selected from 2,1,3-benzothiadiazole, 2,1,3-benzoxadiazole, benzoselenadiazole, benzotellurodiazole, naphthoselenadiazole, 4,7-di(thien-2-yl)-2,1,3-benzothiadiazole, squaraine dyes, quinoxalines, perylene, perylene diimides, diketopyrrolopyrrole, thienopyrazine low bandgap commercial dyes, olefin, cyano-substituted olefin, phenyl, biphenyl and pyridyl.

26. The fluorogenic sensor according to Clause 24, wherein the optionally substituted aryl or heteroaryl co-monomer is selected from the group consisting of substituted or unsubstituted 1,4-phenyl, a substituted or unsubstituted 1,3-phenyl, a substituted or unsubstituted 4,4'-biphenyl, a substituted or unsubstituted 2,5-pyridyl, and a substituted or unsubstituted 2,6-pyridyl.

27. The fluorogenic sensor according to Clause 24, wherein the optionally substituted aryl or heteroaryl co-monomer is selected from one of the following:

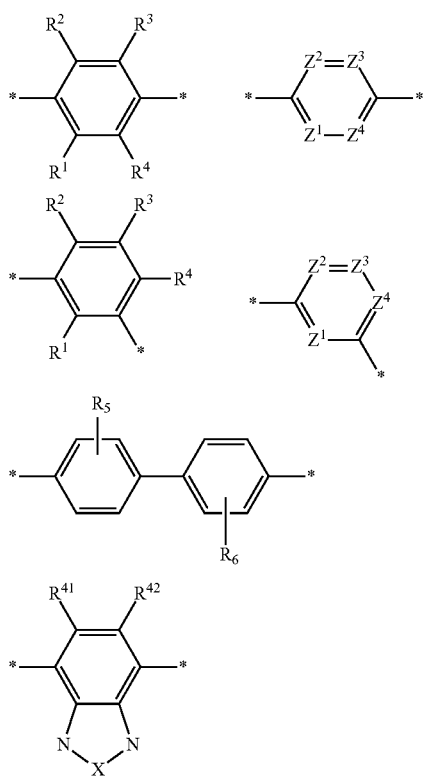

wherein:

$Z^1$-$Z^4$ are each independently CR or N, wherein at least one $Z^1$-$Z^4$ is N;

each R and $R^1$-$R^6$ are independently selected from the group consisting of hydrogen, halogen, cyano, alkoxy, substituted alkoxy, alkyl and substituted alkyl;

X is O or S; and $R^{41}$ and $R^{42}$ are each independently, H, halogen, a WSG, an alkyl, a substituted alkyl, an alkoxy and a substituted alkoxy.

28. The fluorogenic sensor according to Clause 27, wherein the optionally substituted aryl or heteroaryl co-monomer is selected from one of the following:

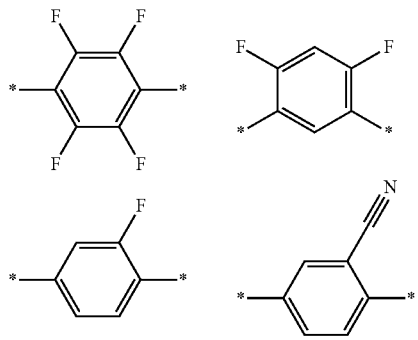

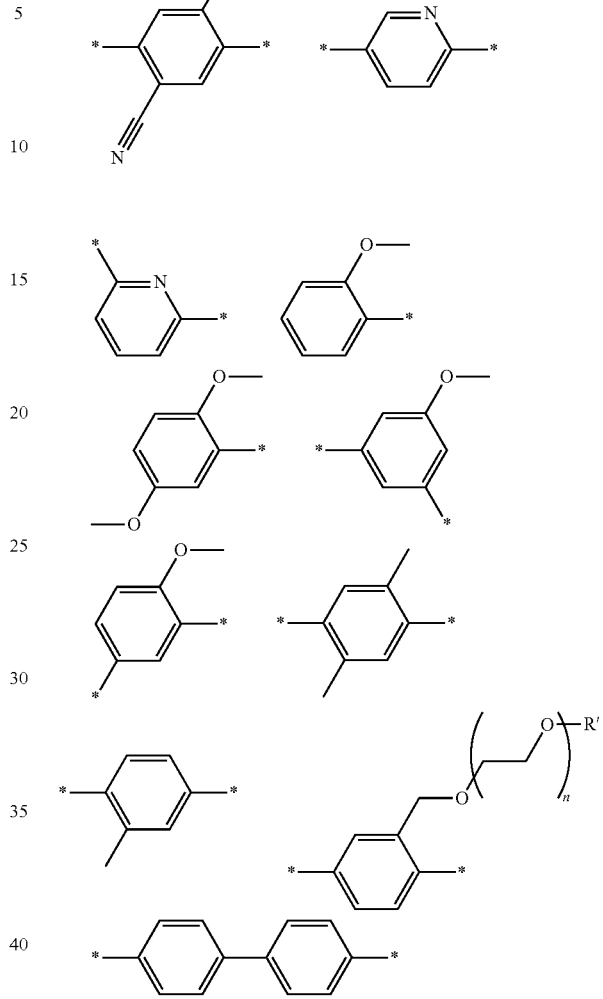

wherein n is 1-20 (e.g., n is 3) and R' is H or lower alkyl (e.g., methyl).

29. The fluorogenic sensor according to any of Clauses 1 to 28, wherein $F^1$ is described by the structure:

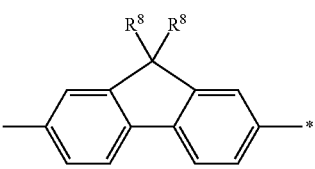

wherein:

each $R^8$ is a substituted alkyl comprising a water soluble group or a substituted aralkyl comprising a water soluble group.

30. The fluorogenic sensor according to any of Clauses 1 to 29, wherein $L^1$ is a fluorene co-monomer.

31. The fluorogenic sensor according to any of Clauses 1 to 30, wherein $L^1$ is described by the structure:

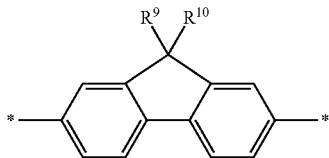

wherein:

$R^9$ is an substituted alkyl comprising a water soluble group I);

$R^{10}$ is $L^2$-$Z^2$ wherein $L^2$ is a linker and $Z^2$ is a linked fluorogenic dye.

32. A fluorogenic sensor for a target analyte, the sensor comprising:

a water soluble light harvesting multichromophore comprising a conjugated segment comprising a fluorene co-monomer; and a fluorogenic dye covalently linked to the multichromophore in energy-receiving proximity therewith;

wherein the fluorogenic dye comprises a lactone or spirolactone group that is configured to chemically react with a target analyte via lactone ring-opening to produce a fluorescent dye configured for excitation by the multichromophore.

33. The fluorogenic sensor according to Clause 32, wherein the linked fluorogenic dye is non-fluorescent in the absence of target analyte when the sensor is irradiated with light at the absorption maxima wavelength of the multichromophore.

34. The fluorogenic sensor according to Clause 32, wherein the linked fluorogenic dye quenches 10% or more of the fluorescence of the multichromophore.

35. The fluorogenic sensor according to Clause 32, wherein the ratiometric fluorescence change of the fluorescent dye from the absence of target analyte to the presence of target analyte is 1000 fold or more.

36. The fluorogenic sensor according to any of Clauses 32 to 34, wherein the linked fluorogenic dye is a pH sensor.

37. The fluorogenic sensor according to any of Clauses 32 to 34, wherein the target analyte is hydroxide.

38. The fluorogenic sensor according to any of Clauses 32 to 37, wherein the linked fluorogenic dye is described by the formula:

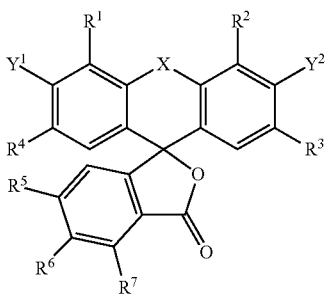

wherein:

$Y^1$ and $Y^2$ are independently OR and $NR_2$, wherein each R is independently H, an alkyl or a substituted alkyl;

X is O or $C(R')_2$ wherein each R' is independently an alkyl or a substituted alkyl;

$R^1$-$R^4$ are each independently H, chloro or fluoro;

$R^5$-$R^7$ are each independently H, a linker, a halogen, an alkyl, a substituted alkyl, an aryl, a substituted aryl, a substituted carboxyamido, a substituted alkoxy, a substituted amino, wherein optionally $R^5$ and $R^6$ or $R^6$ and $R^7$ combine to form a metal ion-chelating moiety;

wherein at least one of $R^5$-$R^7$ is linked to the multichromophore.

39. The fluorogenic sensor according to Clause 38, wherein the linked fluorogenic dye is described by the structure:

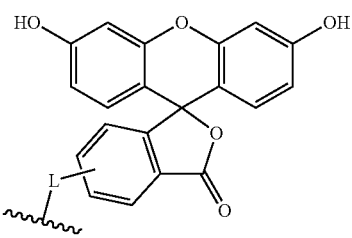

wherein L is a linker covalently attached to the multichromophore.

40. The fluorogenic sensor according to any of Clauses 32 to 38, wherein the fluorescent dye comprises a metal ion-chelating ligand and is configured for a ratiometric fluorescence change upon binding of the metal ion.

41. The fluorogenic sensor according to Clause 40, wherein the linked fluorogenic dye is described by the structure:

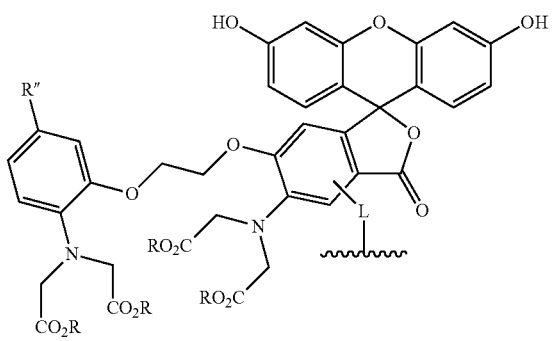

wherein:

R" is H or alkyl;

each R is H or a substituted alkyl; and

L is a linker covalently attached to the multichromophore.

42. The fluorogenic sensor according to Clause 41, wherein each R is H.

43. The fluorogenic sensor according to any of Clauses 32 to 42, wherein the sensor is described by formula (X):

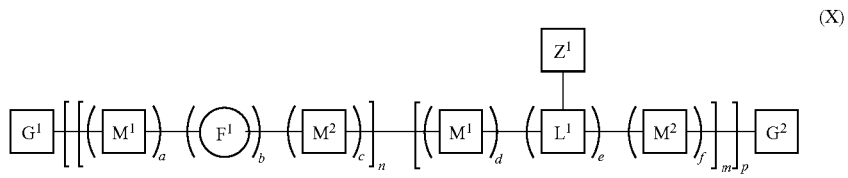

wherein:

F¹ is the fluorene co-monomer;

each M¹ and M² are independently a modifying co-monomer;

L¹ is a linking co-monomer substituted with the fluorogenic dye Z¹;

e is 1;

a, b, c, d and f are each independently 0 or 1, wherein a+b+c+d+f≥1;

n is 0 or an integer from 1 to 10,000;

m is 0 or an integer from 1 to 10,000;

p is an integer from 1 to 100,000; and

G¹ and G² are each independently selected from a terminal group, a □ conjugated segment, a linker and a linked specific binding member.

44. The fluorogenic sensor according to Clause 43, wherein:

b is 1;

a+c≥1;

d+f≥1;

n is an integer from 1 to 10,000; and m is an integer from 1 to 10,000.

45. The fluorogenic sensor according to Clause 43, described by formula (II):

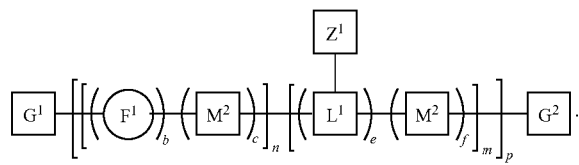

46. The fluorogenic sensor according to Clause 45, wherein:

b is 1;

c is 0 or 1;

e and f are each 1;

G¹ is a terminal group; and

G² is a terminal group, a linker or a linked specific binding member.

47. The fluorogenic sensor according to any of Clauses 45 to 46, wherein c is 1.

48. The fluorogenic sensor according to Clause 43, described by formula (III):

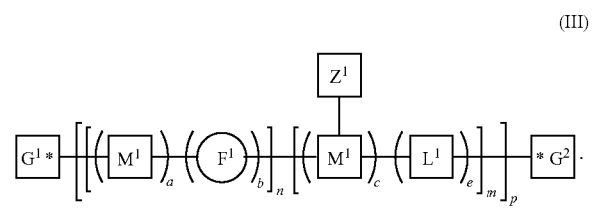

49. The fluorogenic sensor according to any of Clauses 43 to 48, wherein:

G¹ is a terminal group; and

G² is a terminal group, a linker or a linked specific binding member.

50. The fluorogenic sensor according to any of Clauses 43 to 49, wherein a+c=1.

51. The fluorogenic sensor according to any of Clauses 43 to 50, wherein the M¹ and M² co-monomers are independently an optionally substituted aryl or heteroaryl co-monomer.

52. The fluorogenic sensor according to any of Clauses 43 to 51, wherein F¹ is described by the structure:

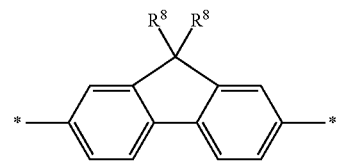

wherein:

each R⁸ is a substituted alkyl comprising a water soluble group or a substituted aralkyl comprising a water soluble group.

53. The fluorogenic sensor according to any of Clauses 43 to 52, wherein L¹ is a fluorene co-monomer.

54. The fluorogenic sensor according to Clause 53, wherein L¹ is described by the structure:

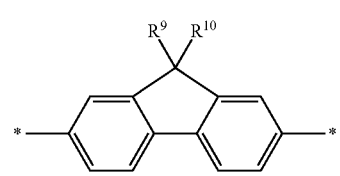

wherein:

R⁹ is an substituted alkyl comprising a water soluble group I);

$R^{10}$ is $L^2$-$Z^2$ wherein $L^2$ is a linker and $Z^2$ is a linked fluorogenic dye.

55. A method of evaluating a sample for the presence of a target analyte, the method comprising:
(a) contacting the sample with a fluorogenic sensor for a target analyte according to any of Clauses 1 and 54 to produce a sensor-contacted sample;
(b) evaluating the sensor-contacted sample for fluorescence emission from the fluorogenic sensor to evaluate whether the target analyte is present in the sample.

56. The method according to Clause 55, wherein the fluorogenic sensor is support bound.

57. The method according to Clause 56, wherein the support comprises a magnetic particle.

58. The method according to Clause 55, wherein the sample is in vitro.

59. The method according to Clause 55, wherein the sample is in vivo.

60. The method according to any of Clauses 55 to 59, wherein the evaluating comprises measuring a ratiometric change in fluorescence of the sensor relative to a control.

61. The method according to any of Clauses 55 to 60, wherein the target analyte is selected from hydroxide, nitric oxide, glucose, lactate, hydrogen peroxide, oxygen, reactive nitrogen species and reactive oxygen species.

62. A labelled specific binding member comprising:
a fluorogenic sensor for a target analyte according to any of Clauses 1 to 54; and
a specific binding member covalently linked to the multichromophore of the fluorogenic sensor, wherein the specific binding member specifically binds to a target biomolecule.

63. The labelled specific binding member according to Clause 62, wherein the specific binding member is an antibody.

64. The labelled specific binding member according to Clause 62, wherein the specific binding member is an antibody fragment or binding derivative thereof.

65. The labelled specific binding member according to Clause 64, wherein the antibody fragment or binding derivative thereof is selected from the group consisting of a Fab fragment, a F(ab')$_2$ fragment, a scFv, a diabody and a triabody.

66. The labelled specific binding member according to any of Clauses 62 to 65, wherein the target biomolecule is associated with a cell.

67. The labelled specific binding member according to Clause 66, wherein the target biomolecule is a cell surface marker of the cell.

68. The labelled specific binding member according to Clause 67, wherein the cell surface marker is selected from a cell receptor and a cell surface antigen.

69. The labelled specific binding member according to Clause 66, wherein the target biomolecule is an intracellular target.

70. The labelled specific binding member according to any of Clauses 62 to 69, wherein the target analyte is selected from hydroxide, nitric oxide, glucose, lactate, hydrogen peroxide, oxygen, reactive nitrogen species and reactive oxygen species.

71. A method of labelling a target molecule, the method comprising:
contacting the target molecule with a fluorogenic sensor for an analyte to produce a labelled target molecule;
wherein the fluorogenic sensor comprises a water soluble light harvesting multichromophore and a linked fluorogenic dye, wherein the sensor is described by formula (X):

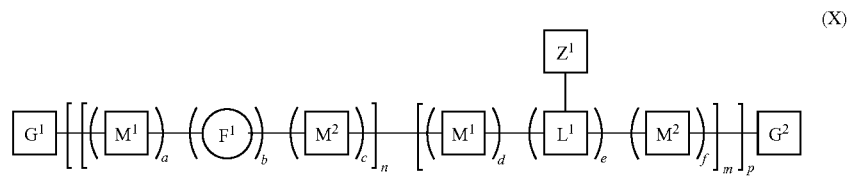

(X)

wherein:
$F^1$ is a fluorene co-monomer;
each $M^1$ and $M^2$ are independently a modifying co-monomer;
$L^1$ is a linking co-monomer substituted with the linked fluorogenic dye $Z^1$ in energy-receiving proximity to the multichromophore;
e is 1;
a, b, c, d and f are each independently 0 or 1, wherein a+b+c+d+f≥1;
n is 0 or an integer from 1 to 10,000;
m is 0 or an integer from 1 to 10,000;
p is an integer from 1 to 100,000; and
$G^1$ and $G^2$ are each independently selected from a terminal group, a □ conjugated segment, a linker and a conjugation tag that covalently links to the target molecule, wherein at least one of $G^1$ and $G^2$ comprises the conjugation tag;
wherein the fluorogenic dye is configured to sense the analyte to produce a fluorescent dye configured for excitation by the multichromophore.

72. The method according to Clause 71, further comprising contacting a sample with the labelled target molecule to evaluate the sample for the presence of the analyte.

73. The method according to Clause 71, wherein the conjugation tag comprises a terminal functional group selected from an amino, a thiol, a hydroxyl, a hydrazine, a hydrazide, a azide, an alkyne and a protein reactive group.

74. The method according to any of Clauses 71 to 73, wherein the target molecule is a specific binding member.

75. The method according to Clause 74, wherein the specific binding member is an antibody.

76. The method according to Clause 74, wherein the specific binding member is an antibody fragment or binding derivative thereof.

77. The method according to Clause 76, wherein the antibody fragment or binding derivative thereof is selected from the group consisting of a Fab fragment, a F(ab')$_2$ fragment, a scFv, a diabody and a triabody.

78. The method according to any of Clauses 71 to 77, wherein the analyte is selected from hydroxide, nitric oxide, glucose, lactate, hydrogen peroxide, oxygen, reactive nitrogen species and reactive oxygen species.

79. A flow cytometric system, the system comprising:
a flow cytometer comprising a flow path;
a composition in the flow path, wherein the composition comprises:
a sample; and
a fluorogenic sensor for a target analyte according to any of Clauses 1 to 54.
80. The system according to Clause 79, wherein the multichromophore of the fluorogenic sensor is covalently linked to a specific binding member that specifically binds a target biomolecule.
81. The system according to Clause 79, wherein the composition further comprises a second specific binding member that is support bound and specifically binds the target biomolecule.
82. The system according to Clause 80, wherein the support comprises a magnetic particle.
83. The system according to any of Clauses 79 to 82, wherein the sample comprises a cell.
84. The system according to Clause 83, wherein the target biomolecule is a cell surface marker of the cell.
85. The system according to Clause 84, wherein the cell surface marker is selected from the group consisting of a cell receptor and a cell surface antigen.
86 The system according to any of Clauses 79 to 85, wherein the target analyte is selected from hydroxide, nitric oxide, glucose, lactate, hydrogen peroxide, oxygen, reactive oxygen species and reactive oxygen species.
87. A kit comprising:
a fluorogenic sensor for a target analyte of any of Clauses 1 to 54; and
one or more components selected from the group consisting of a polymeric tandem dye, a fluorophore, a specific binding member, a specific binding member conjugate, a cell, a support, a biocompatible aqueous elution buffer, and instructions for use.
88. The kit according to Clause 87, wherein the multichromophore of the fluorogenic sensor is covalently linked to a specific binding member.
89. The kit according to Clause 88, wherein the specific binding member is an antibody.
90. The kit according to Clause 88, wherein the specific binding member is an antibody fragment or binding derivative thereof.
91. The kit according to Clause 90, wherein the antibody fragment or binding derivative thereof is selected from the group consisting of a Fab fragment, a F(ab')$_2$ fragment, a scFv, a diabody and a triabody.
92. The kit according to any of Clauses 87 to 91, wherein the target analyte is selected from hydroxide, nitric oxide, glucose, lactate, hydrogen peroxide, oxygen, reactive nitrogen species and reactive oxygen species.
93. A device for monitoring a target analyte in a subject, the device comprising:
a fluorogenic sensor for a target analyte according to any of Clauses 1 to 54; and
a means for fluorescently detecting the fluorescent dye configured for excitation by the multichromophore.
94. The device according to Clause 93, further comprising a means for obtaining a biological sample from the subject.
95. The device according to Clause 93, further comprising a means for evaluating a ratiometric change in fluorescence of the fluorogenic sensor.
96. The device according to any of Clauses 93 to 95, wherein the target analyte is glucose.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the following.

What is claimed is:

1. A fluorogenic sensor for hydroxide, the sensor comprising a water soluble light harvesting multichromophore and a linked fluorogenic dye in energy-receiving proximity therewith, wherein the sensor is described by formula (X):

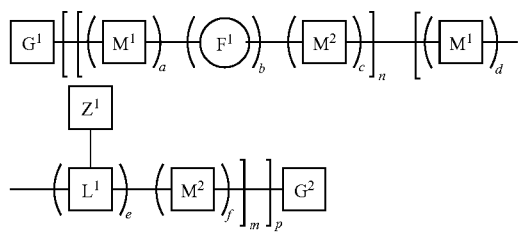

wherein:

$Z^1$ is the linked fluorogenic dye in energy receiving proximity to the multichromophore;

$F^1$ is a fluorene co-monomer;

each $M^1$ and each $M^2$ is independently a co-monomer;

$L^1$ is a fluorene co-monomer substituted with the linked fluorogenic dye ($Z^1$);

e is 1;

a, b, c, d and f are each independently 0 or 1, wherein $a+b+c+d+f \geq 1$;

n is 0 or an integer from 1 to 10,000;

m is an integer from 1 to 10,000;

p is an integer from 1 to 100,000; and $G^1$ and $G^2$ are each independently selected from a terminal group, a π conjugated segment, a linker and a linked specific binding member;

wherein the fluorogenic dye has the structure

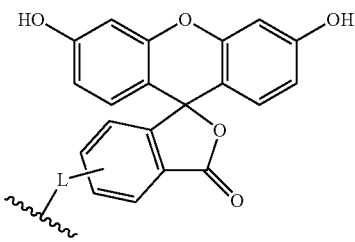

wherein L is a linker covalently attached to the multichromophore.

2. The fluorogenic sensor according to claim 1, wherein the linked fluorogenic dye is non-fluorescent in the absence of target analyte when the sensor is irradiated with incident excitation light at the absorption maxima wavelength of the multichromophore.

3. The fluorogenic sensor according to claim 1, wherein the linked fluorogenic dye quenches 10% or more of the fluorescence of the multichromophore.

4. The fluorogenic sensor according to claim 1, wherein the fluorescence ratio of the fluorescent versus non-fluorescent forms of the sensor is 10 or more.

5. The fluorogenic sensor according to claim 1, described by formula (II):

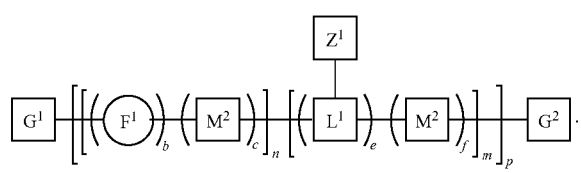

(II)

6. The fluorogenic sensor according to claim 1, described by formula (III):

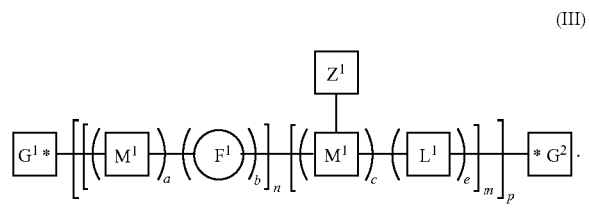

(III)

7. A method of evaluating a sample for the presence of hydroxide, the method comprising:
(a) contacting the sample with the fluorogenic sensor according to claim 1 to produce a sensor-contacted sample;
(b) evaluating the sensor-contacted sample for fluorescence emission from the fluorogenic sensor to evaluate whether hydroxide is present in the sample.

8. The method according to claim 7, wherein the fluorogenic sensor is support bound.

9. The method according to claim 8, wherein the support comprises a magnetic particle.

10. The method according to claim 7, wherein said contacting is carried out in vitro.

11. The method according to claim 7, wherein said contacting is carried out in vivo.

12. The method according claim 7, wherein the evaluating comprises measuring a ratiometric change in fluorescence of the sensor relative to a control.

* * * * *